United States Patent
Liu et al.

(10) Patent No.: US 11,673,957 B2
(45) Date of Patent: Jun. 13, 2023

(54) ANTI-ROR2 ANTIBODIES

(71) Applicants: EUREKA THERAPEUTICS, INC., Emeryville, CA (US); MEMORIAL SLOAN-KETTERING CANCER CENTER, New York, NY (US)

(72) Inventors: Cheng Liu, Oakland, CA (US); Su Yan, State College, PA (US); Pei Wang, Union City, CA (US); Nai-Kong Cheung, Purchase, NY (US); Hongfen Guo, Forest Hills, NY (US); Ming Cheng, Roosevelt Island, NY (US)

(73) Assignee: Eureka Therapeutics, Inc., Emeryville, CA (US)

( * ) Notice: Subject to any disclaimer, the term of this patent is extended or adjusted under 35 U.S.C. 154(b) by 287 days.

(21) Appl. No.: 15/555,036

(22) PCT Filed: Mar. 10, 2016

(86) PCT No.: PCT/IB2016/000255
§ 371 (c)(1),
(2) Date: Dec. 27, 2017

(87) PCT Pub. No.: WO2016/142768
PCT Pub. Date: Sep. 15, 2016

(65) Prior Publication Data
US 2018/0127503 A1    May 10, 2018

Related U.S. Application Data

(60) Provisional application No. 62/219,587, filed on Sep. 16, 2015, provisional application No. 62/131,128, filed on Mar. 10, 2015.

(51) Int. Cl.
| | | |
|---|---|---|
| *C07K 16/18* | (2006.01) | |
| *C07K 16/28* | (2006.01) | |
| *A61K 47/68* | (2017.01) | |
| *C07K 16/22* | (2006.01) | |
| *A61K 39/00* | (2006.01) | |

(52) U.S. Cl.
CPC ...... *C07K 16/2857* (2013.01); *A61K 47/6891* (2017.08); *C07K 16/22* (2013.01); *C07K 16/2803* (2013.01); *A61K 2039/505* (2013.01); *C07K 2317/21* (2013.01); *C07K 2317/31* (2013.01); *C07K 2317/34* (2013.01); *C07K 2317/622* (2013.01); *C07K 2317/732* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

WO    2013/103637 A1    7/2013

OTHER PUBLICATIONS

Oishi et al., The receptor tyrosine kinase Ror2 is involved in non-canonical Wnt5a/JNK signalling pathway. Genes to Cells 8:645-654, 2003.*
Masiakowski et al., A novel family of cell surface receptors with tyrosine kinase-like domain. J Biol Chem. 267(36):26181-26190, 1992.*
Gura (1997) Science 278: 1041-1042.*
Choi et al., "Bispecific antibodies engage T cells for antitumor immunotherapy", Expert Opinion on Biological Therapy, vol. 11, No. 7, Mar. 30, 2011, pp. 1-11.
International Search Report and Written Opinion for international application No. PCT/IB2016/000255 dated Jul. 6, 2016, 11 pages.

* cited by examiner

*Primary Examiner* — Michael D Pak
(74) *Attorney, Agent, or Firm* — Kilpatrick Townsend & Stockton LLP

(57) ABSTRACT

The invention relates to antibodies, and in particular, to antibodies exhibiting specificity for Receptor tyrosine kinase-like Orphan Receptors (ROR), and to uses thereof for example in the treatment of cancer. The invention extends to polynucleotide and polypeptide sequences encoding the antibodies, and therapeutic uses thereof, and to diagnostic kits comprising these molecules. The invention also extends to antibody-drug conjugates and to uses thereof in therapy.

14 Claims, 22 Drawing Sheets
Specification includes a Sequence Listing.

Figure: 1
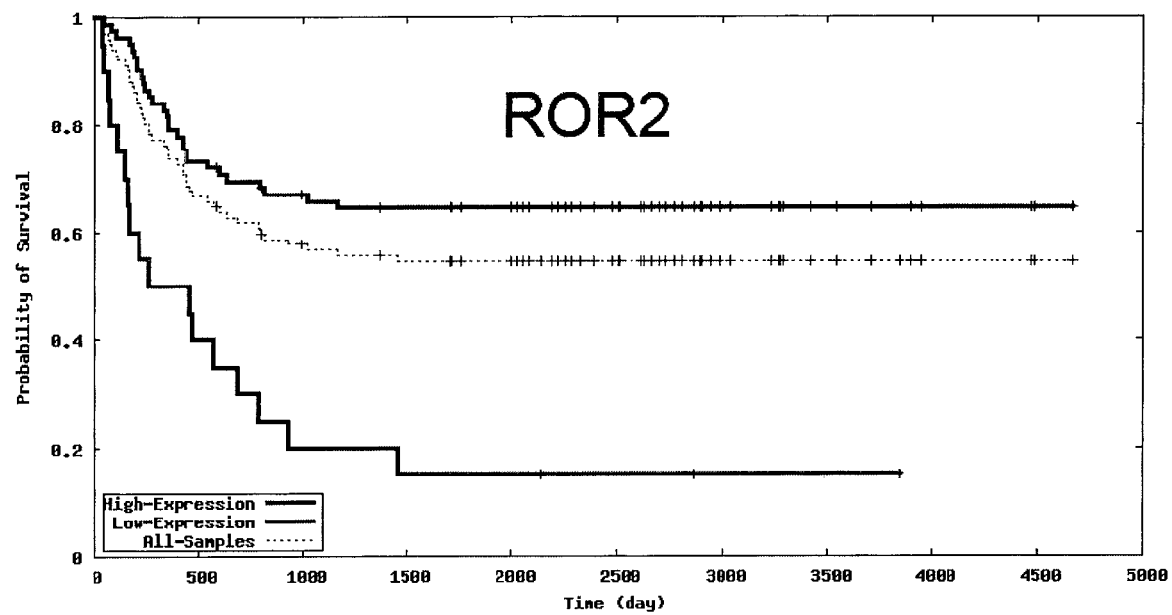

Figure: 2
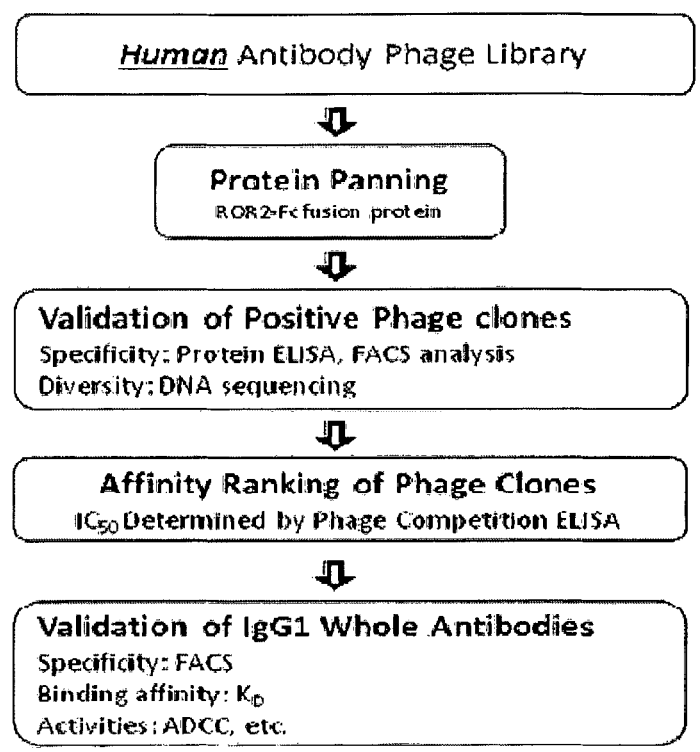

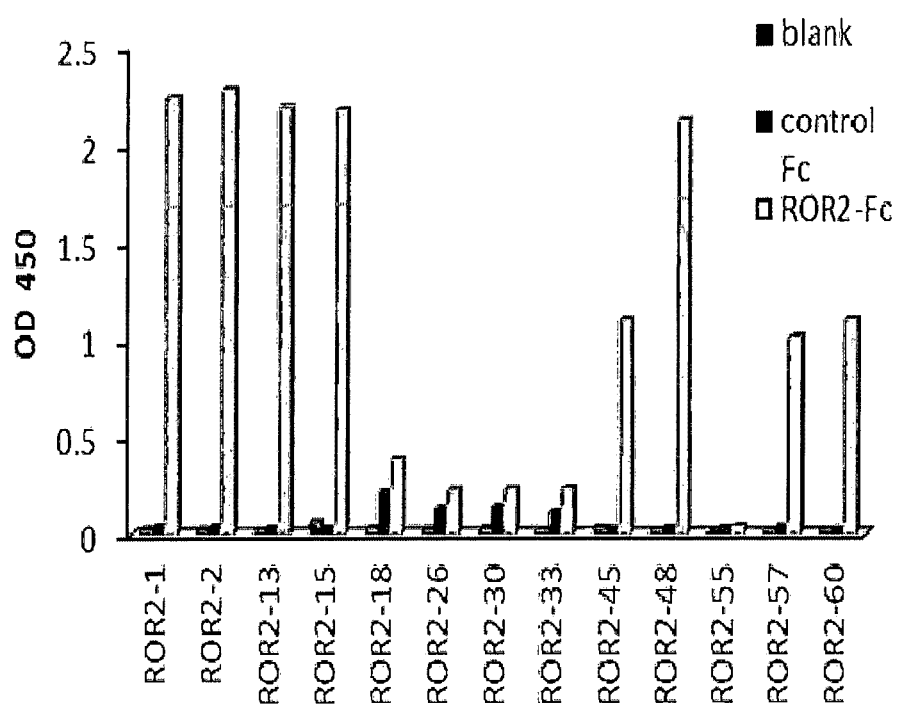
Figure: 3

Figure: 4
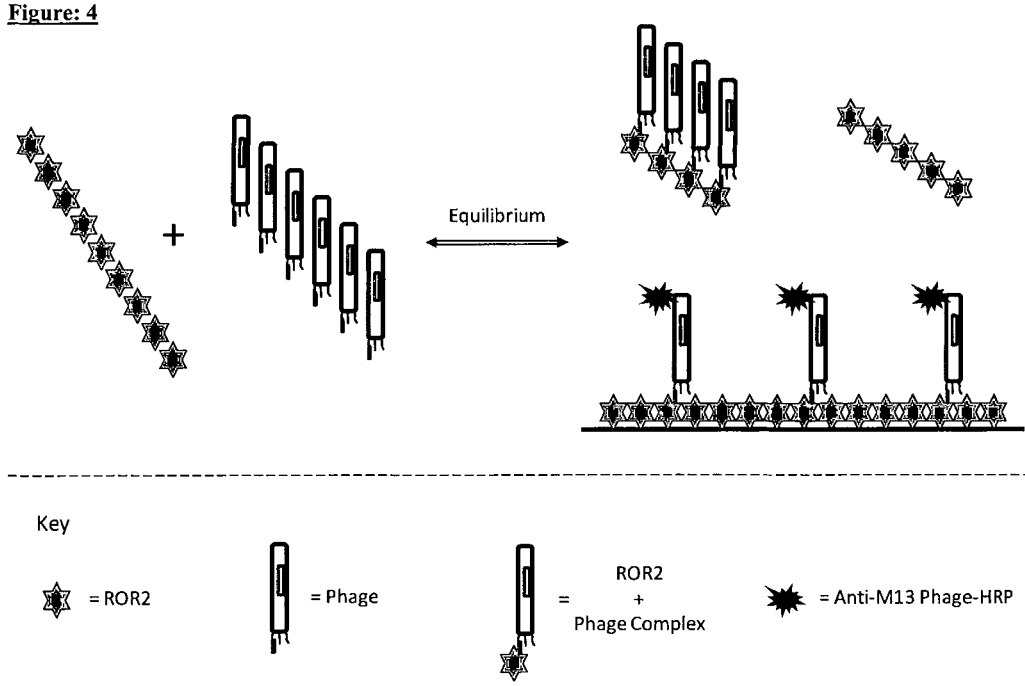

Figure: 5
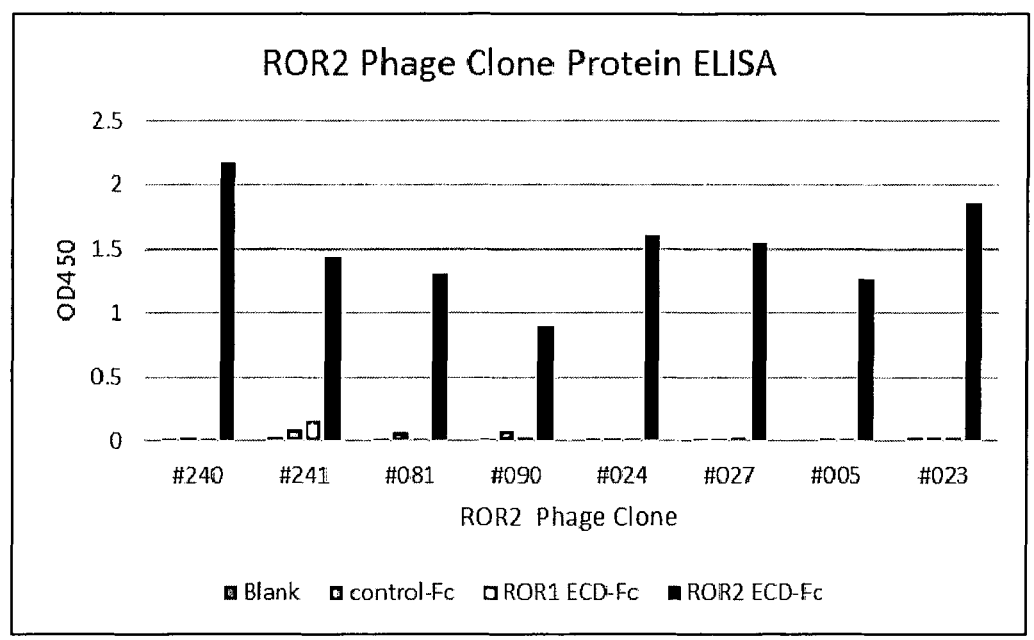

Figure: 6
A) *HCT-116 Cell*
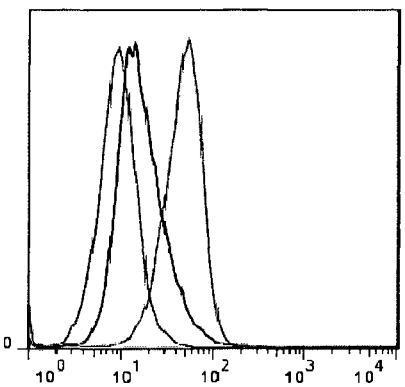
Figure: 7
B) *Jurkat Cell*
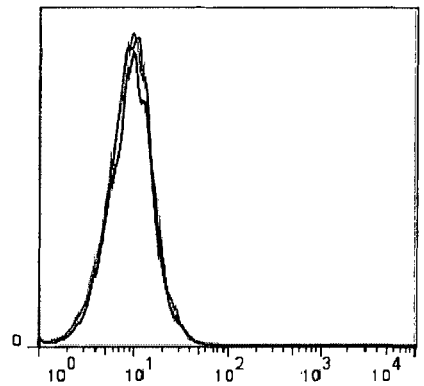

Figure: 8
A) HCT-116 Cell
B) Jurkat Cell
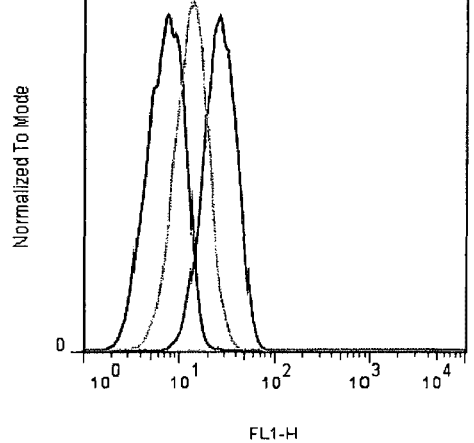
| | Sample Name | Geom. Mean FL1-H |
|---|---|---|
| | HCT116 Positive Ab Control2 | 13.0 |
| | HCT116 Positive Ab Control1 | 26.1 |
| | HCT116 Cell only | 7.09 |
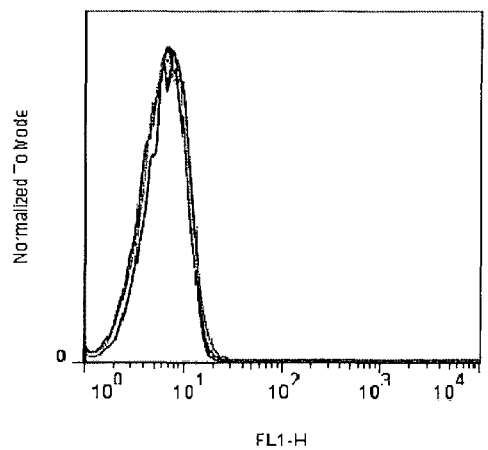
| | Sample Name | Geom. Mean FL1-H |
|---|---|---|
| | jurkat positive Ab control2 | 6.15 |
| | jurkat positive Ab control1 | 6.49 |
| | jurkat cell | 5.81 |

Figure: 9a
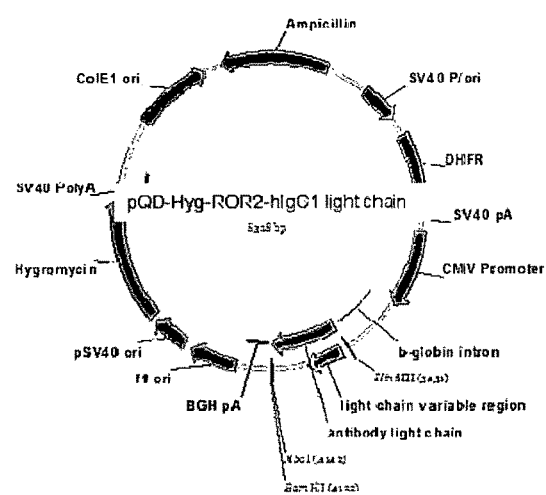
Figure: 9b
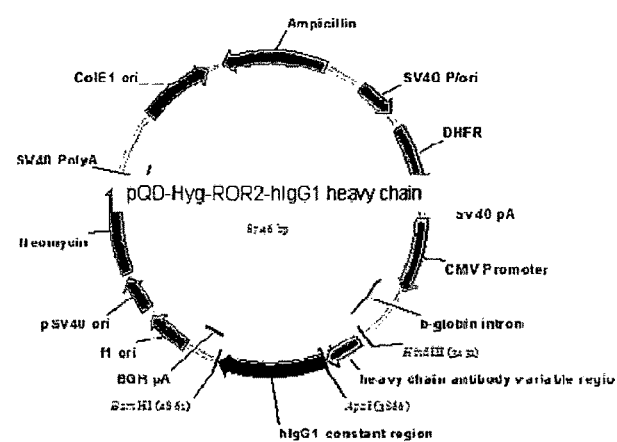

Figure: 10
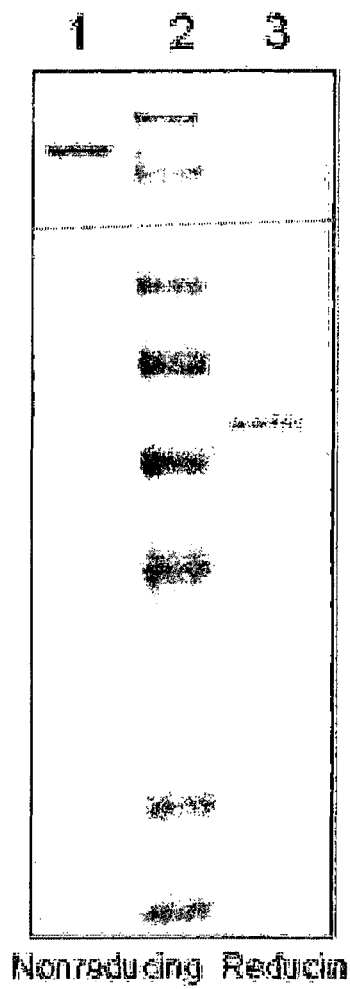
Lanes:
1. ROR2-90, 1 ug, non-reducing
2. SeeBlue Plus2 ladder (10 uL)
3. ROR2-90, 1 ug, reducing
⇐ Heavy chain
⇐ Light chain
Nonreducing  Reducing

Figure: 11
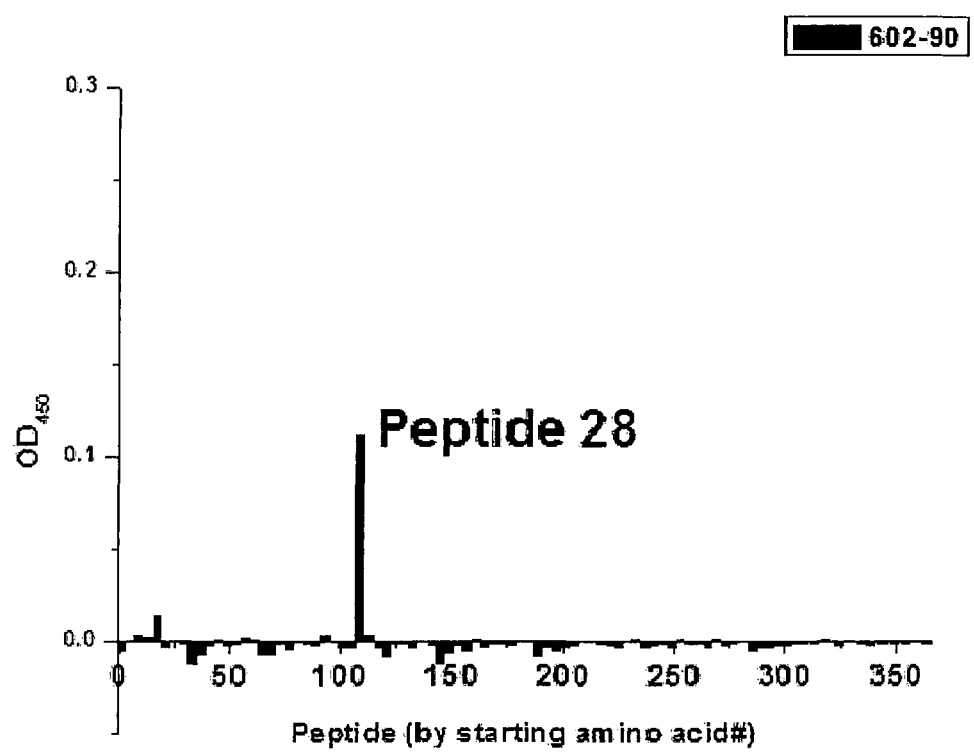
Epitope for clone #90 mAb (need to be refined)
KTITATGVLFVRLGP
(C-terminal of Ig domain)

Figure: 12

|     |            |            |            |            | Ig domain  |
|-----|------------|------------|------------|------------|------------|
| 1   | EVEVLDPNDP | LGPLDGQDGP | IPTLKGYFLN | FLEPVNNITI | VQGQTAILHC |

|     | Ig domain  |            |            |            |            |
|-----|------------|------------|------------|------------|------------|
| 51  | KVAGNPPPNV | RWLKNDAPVV | QEPRRIIIRK | TEYGSRLRIQ | DLDTTDTGYY |

|     | Ig domain  |            |            | CRD-FZ domain |         |
|-----|------------|------------|------------|---------------|---------|
| 101 | QCVATNGMKT | ITATGVLFVR | LGPTHSPNHN | FQDDYHEDGF | CQPYRGIACA |

|     |            |            | CRD-FZ domain |         |            |
|-----|------------|------------|------------|------------|------------|
| 151 | RFIGNRTIYV | DSLQMQGEIE | NRITAAFTMI | GTSTHLSDQC | SQFAIPSFCH |

|     |            |            | CRD-FZ domain |         |            |
|-----|------------|------------|------------|------------|------------|
| 201 | FVFPLCDARS | RAPKPRELCR | DECEVLESDL | CRQEYTIARS | NPLILMRLQL |

|     | CRD-FZ domain |         |            | putative domain interaction sit / Kringle domain | |
|-----|------------|------------|------------|------------|------------|
| 251 | PKCEALPMPE | SPDAANCMRI | GIPAERLGRY | HQCYNGSGMD | YRGTASTTKS |

|     |            | Kringle domain |        |            |            |
|-----|------------|------------|------------|------------|------------|
| 301 | GHQCQPWALQ | HPHSHHLSST | DFPELGGGHA | YCRNPGGQME | GPWCFTQNKN |

|     | Kringle domain |        | Linker-His tag |      |            |
|-----|------------|------------|------------|------------|------------|
| 351 | VRMELCDVPS | CSPRDSSKMG | TSGGGSLVPR | GSGSHHHHHH |            |

Figure: 13
ROR2-23 = clone #23 = 602-23
ROR2-90 = clone #90 = 602-90
ROR2-27 = clone #27 = 602-27
ROR2-240 = clone #240 = 602-240
ROR2-241= clone #241 = 602-241
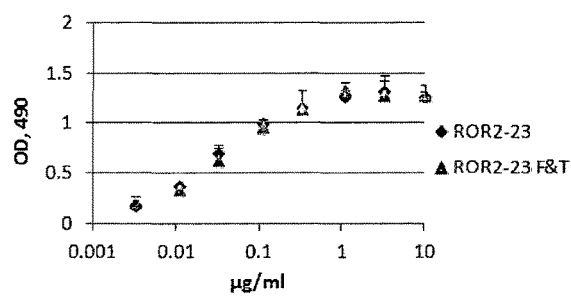
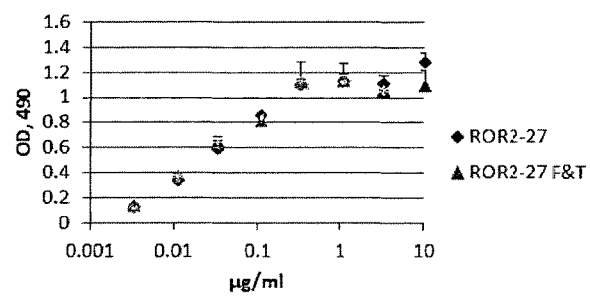

Figure: 13 (continued)
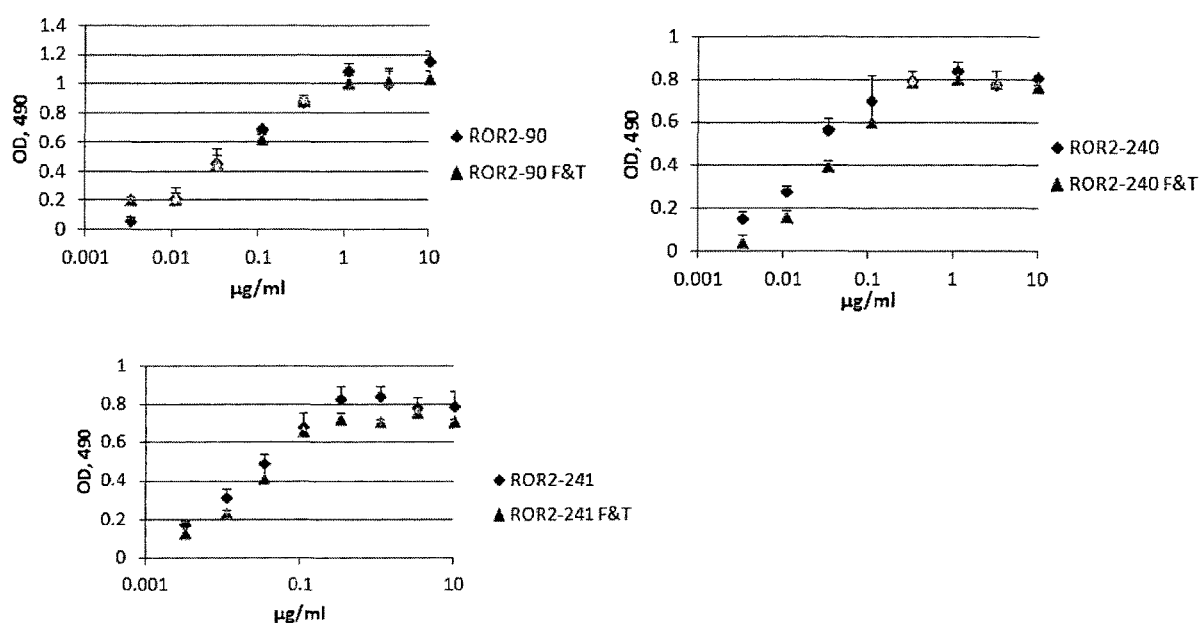

Figure: 14
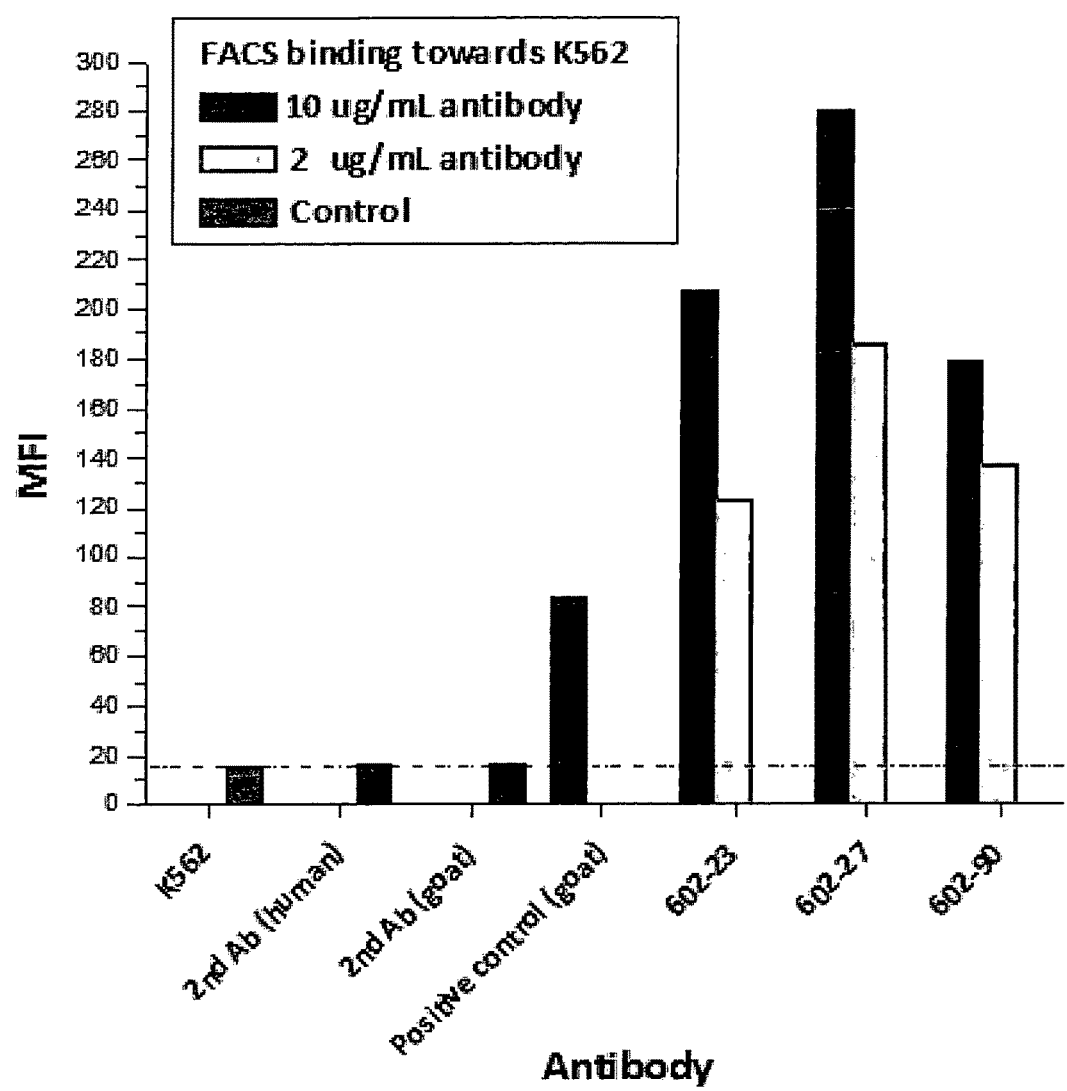

Figure: 15
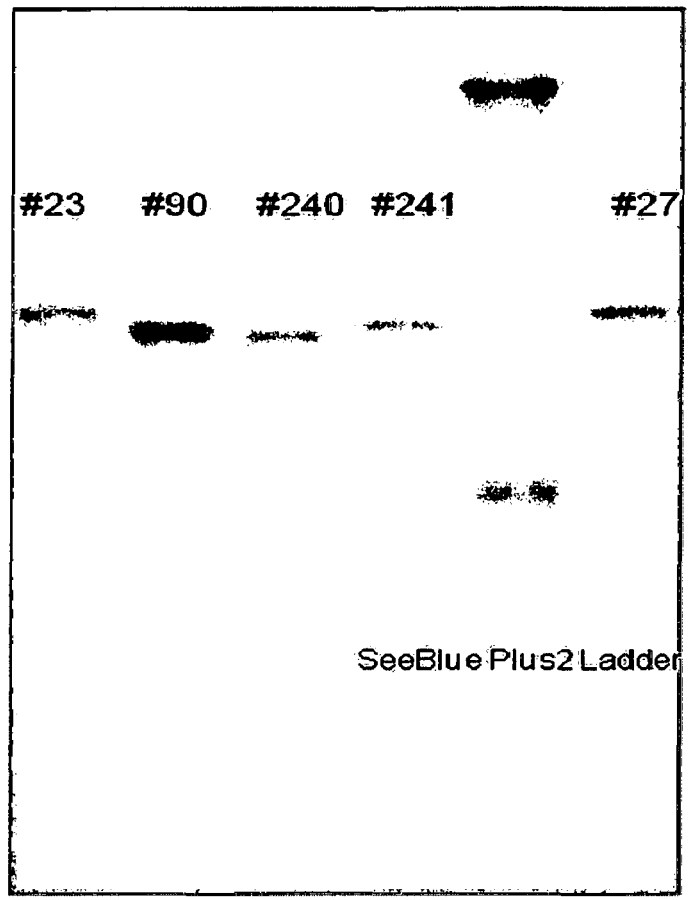
Nonreducing Gel
ROR2-23 = clone #23 = 602-23 = #23
ROR2-90 = clone #90 = 602-90 = #90
ROR2-27 = clone #27 = 602-27 = #27
ROR2-240 = clone #240 = 602-240 = #240
ROR2-241= clone #241 = 602-241 = #241

Figure: 16
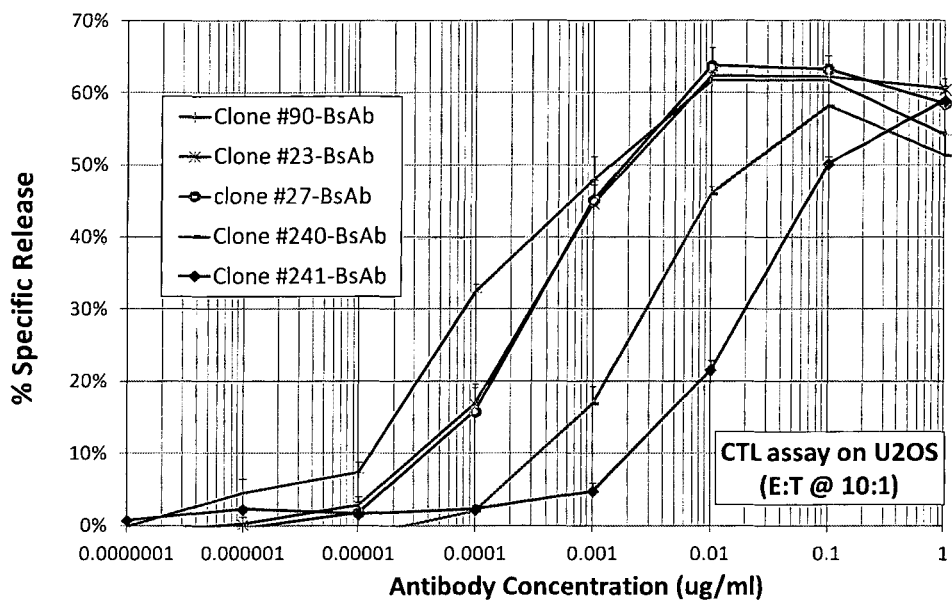
Figure: 17
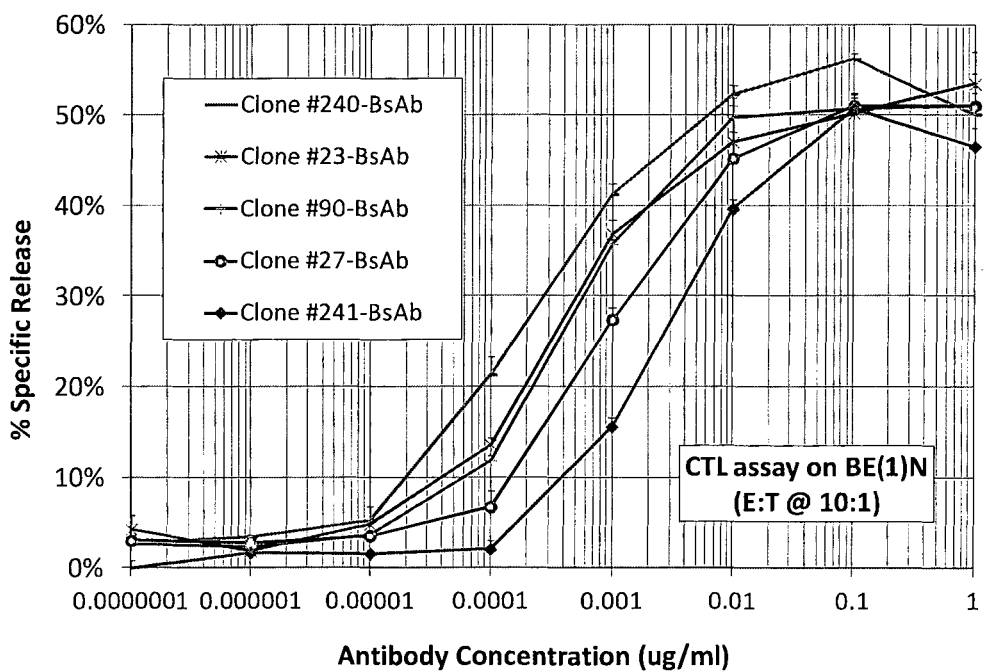

Figure: 18
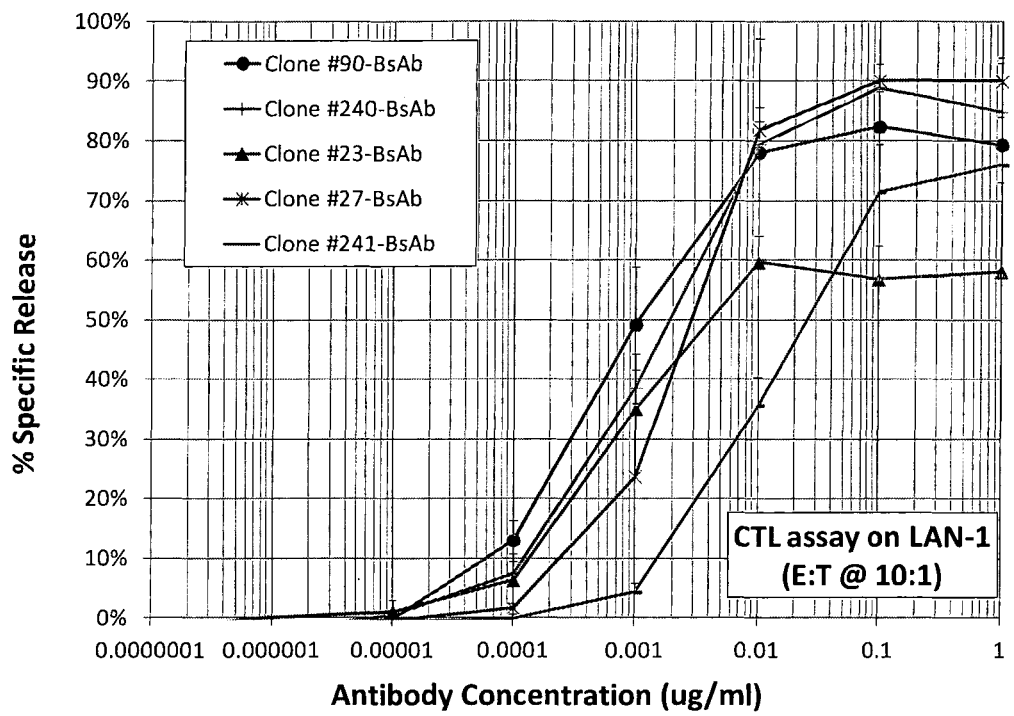
Figure: 19
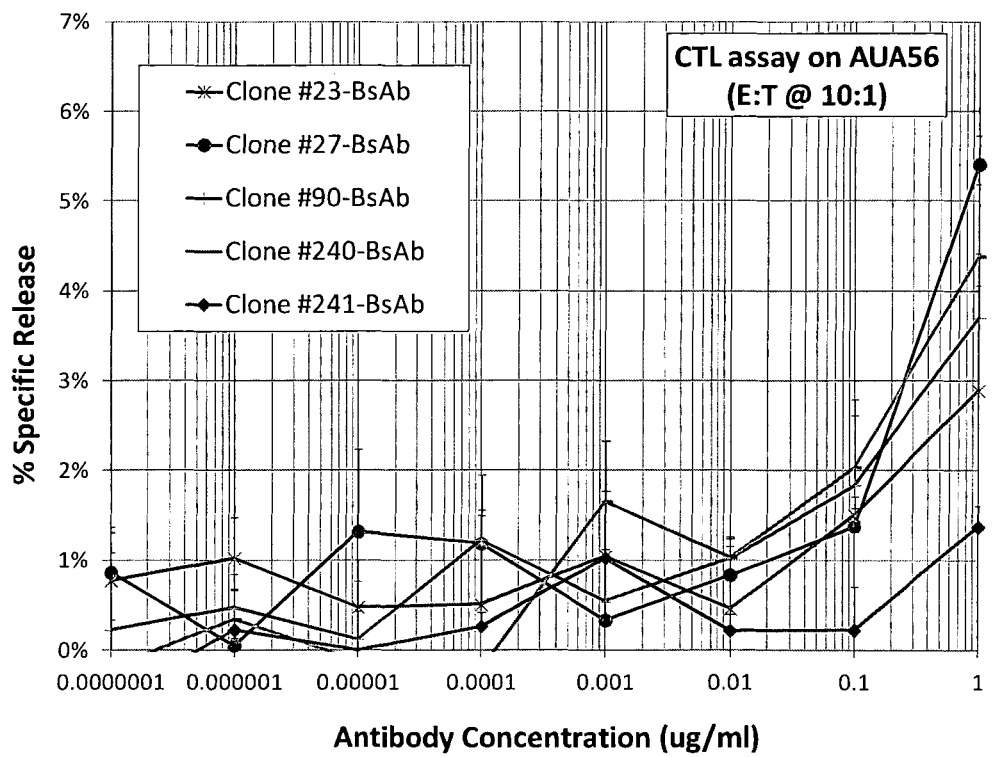

Figure: 20
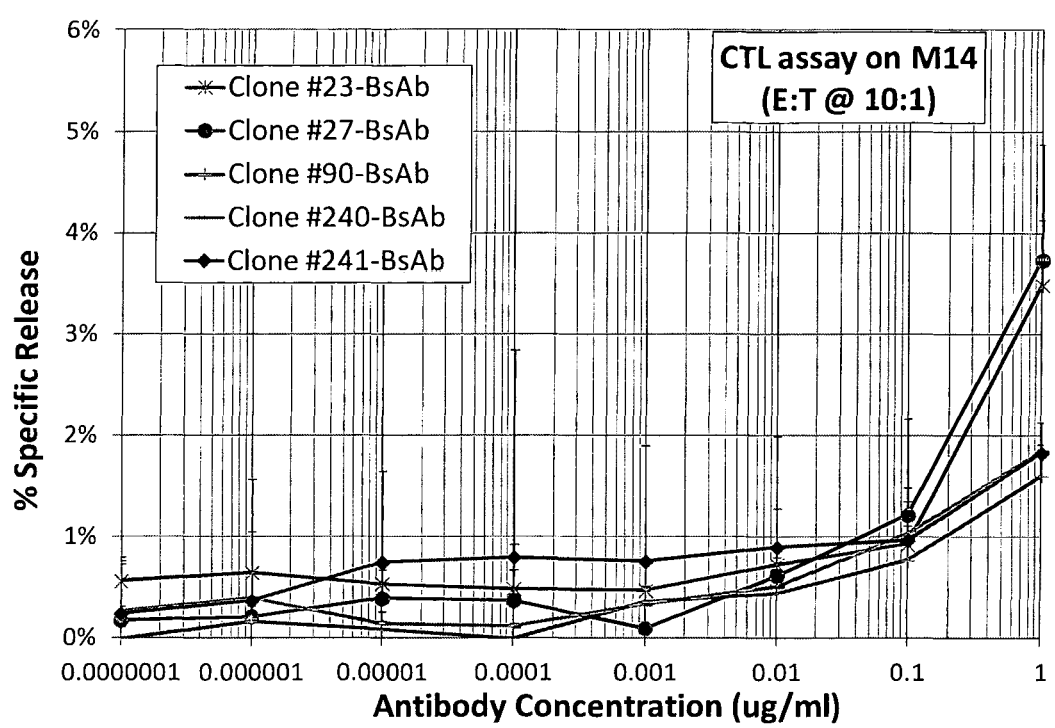

Figure: 21
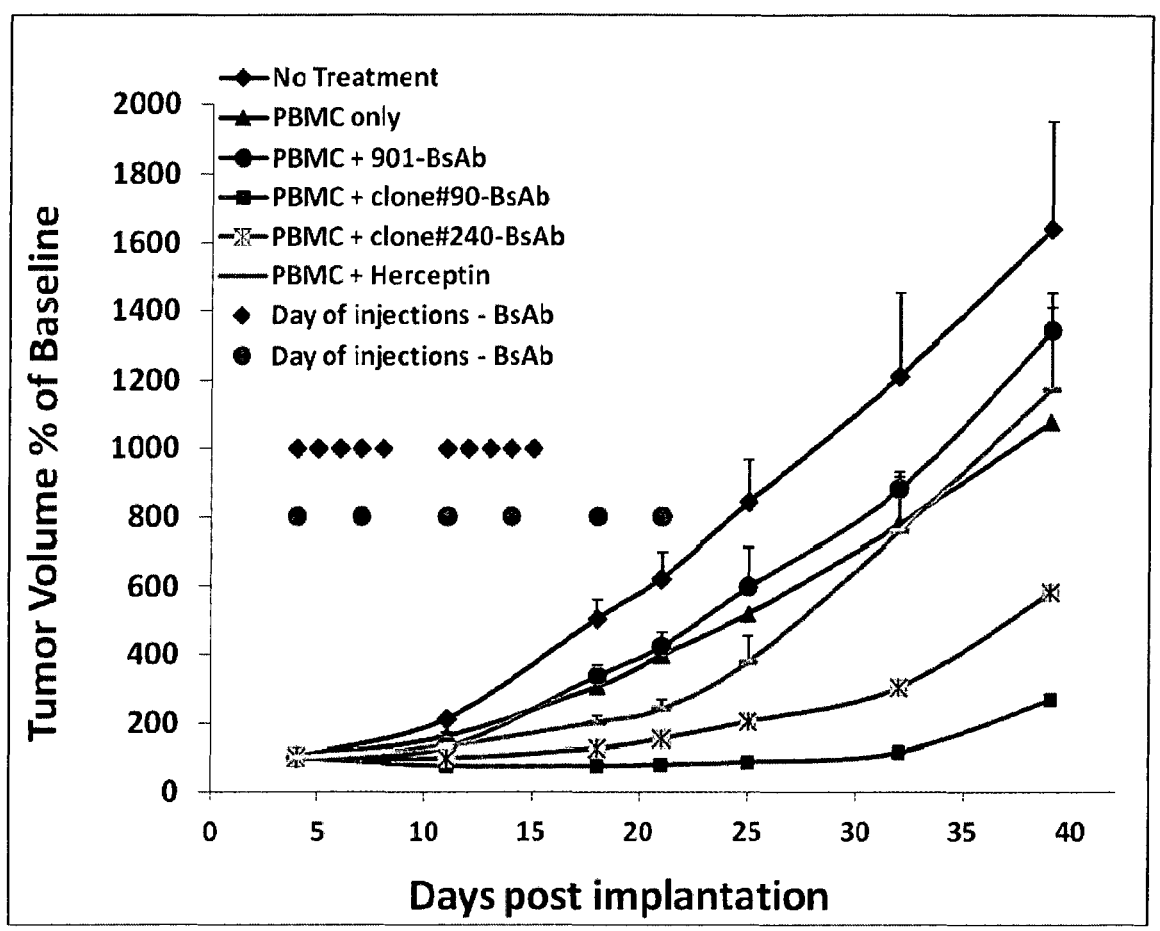

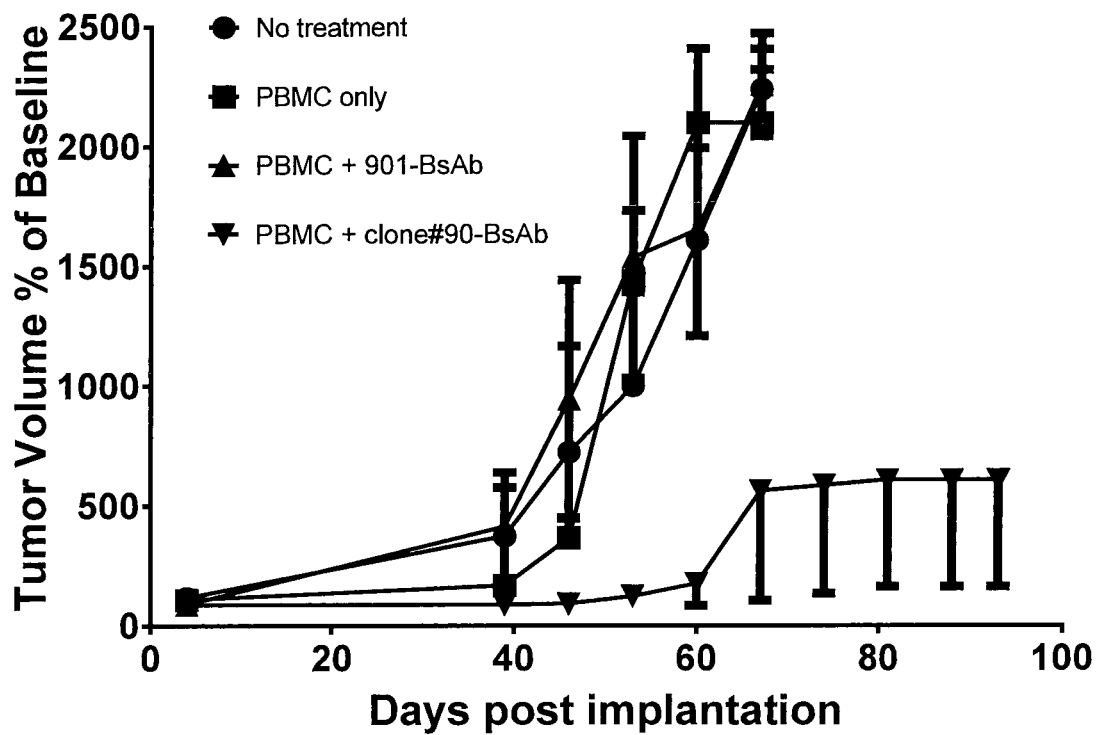
Figure: 22

Figure: 23
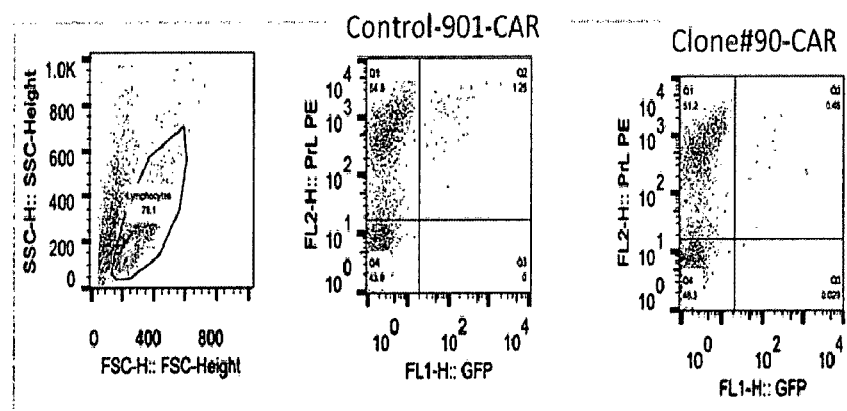

Figure: 24
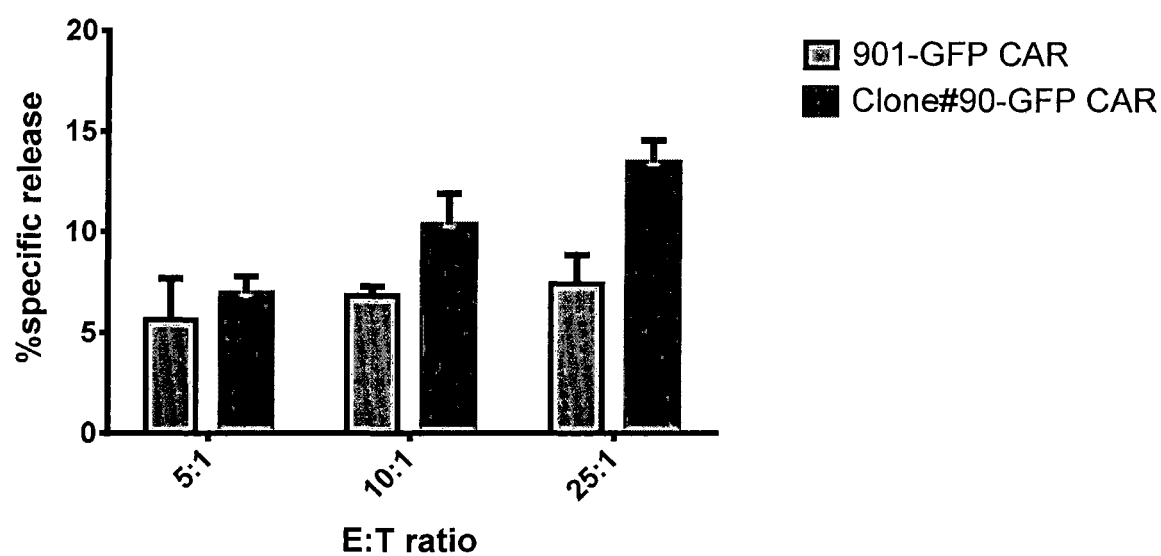

SEQUENCE LISTING

<160> NUMBER OF SEQ ID NOS: 233

<210> SEQ ID NO 1
<211> LENGTH: 8
<212> TYPE: PRT
<213> ORGANISM: Homo sapiens

<400> SEQUENCE: 1

Gly Tyr Thr Phe Thr Asp Tyr Tyr
1               5

<210> SEQ ID NO 2
<211> LENGTH: 24
<212> TYPE: DNA
<213> ORGANISM: Homo sapiens

<400> SEQUENCE: 2
ggatacacct tcaccgacta ctat                                          24

<210> SEQ ID NO 3
<211> LENGTH: 8
<212> TYPE: PRT
<213> ORGANISM: Homo sapiens

<400> SEQUENCE: 3

Met Asn Pro Asn Ser Gly Asn Ser
1               5

<210> SEQ ID NO 4
<211> LENGTH: 24
<212> TYPE: DNA
<213> ORGANISM: Homo sapiens

<400> SEQUENCE: 4 atgaaccota acagtgggaa ctca                                          24

<210> SEQ ID NO 5
<211> LENGTH: 14
<212> TYPE: PRT
<213> ORGANISM: Homo sapiens

<400> SEQUENCE: 5

Ala Arg Asn Ser Glu Trp His Pro Trp Gly Tyr Tyr Asp Tyr
1               5                   10

<210> SEQ ID NO 6
<211> LENGTH: 42
<212> TYPE: DNA
<213> ORGANISM: Homo sapiens

<400> SEQUENCE: 6
gcgcgcaact ctgaatggca tccgtggggt tactacgatt ac                      42

<210> SEQ ID NO 7
<211> LENGTH: 6
<212> TYPE: PRT
<213> ORGANISM: Homo sapiens

<400> SEQUENCE: 7

Ser Leu Arg Ser Tyr Tyr
1               5

<210> SEQ ID NO 8
<211> LENGTH: 18

```
<212> TYPE: DNA
<213> ORGANISM: Homo sapiens

<400> SEQUENCE: 8
agcctcagaa gctattat                                                 18

<210> SEQ ID NO 9
<211> LENGTH: 3
<212> TYPE: PRT
<213> ORGANISM: Homo sapiens

<400> SEQUENCE: 9

Gly Lys Asn
1

<210> SEQ ID NO 10
<211> LENGTH: 9
<212> TYPE: DNA
<213> ORGANISM: Homo sapiens

<400> SEQUENCE: 10 ggtaaaaac                                                            9

<210> SEQ ID NO 11
<211> LENGTH: 11
<212> TYPE: PRT
<213> ORGANISM: Homo sapiens

<400> SEQUENCE: 11

Asn Ser Arg Asp Ser Ser Gly Asn His Leu Val
1               5                   10

<210> SEQ ID NO 12
<211> LENGTH: 33
<212> TYPE: DNA
<213> ORGANISM: Homo sapiens

<400> SEQUENCE: 12
aactcccggg acagcagtgg taaccatctg gta                                 33

<210> SEQ ID NO 13
<211> LENGTH: 8
<212> TYPE: PRT
<213> ORGANISM: Homo sapiens

<400> SEQUENCE: 13

Gly Tyr Arg Phe Ser Lys Tyr Trp
1               5

<210> SEQ ID NO 14
<211> LENGTH: 24
<212> TYPE: DNA
<213> ORGANISM: Homo sapiens

<400> SEQUENCE: 14
ggatacaggt tcagcaagta ctgg                                           24

<210> SEQ ID NO 15
<211> LENGTH: 8
<212> TYPE: PRT
<213> ORGANISM: Homo sapiens

<400> SEQUENCE: 15

Ile Tyr Pro Gly Asp Ser Asp Thr
```

<210> SEQ ID NO 16
<211> LENGTH: 24
<212> TYPE: DNA
<213> ORGANISM: Homo sapiens

<400> SEQUENCE: 16
atctatcctg gtgactctga tacc                                       24

<210> SEQ ID NO 17
<211> LENGTH: 11
<212> TYPE: PRT
<213> ORGANISM: Homo sapiens

<400> SEQUENCE: 17

Ala Arg Ser Phe Ser Ser Phe Ile Tyr Asp Tyr
1               5                   10

<210> SEQ ID NO 18
<211> LENGTH: 33
<212> TYPE: DNA
<213> ORGANISM: Homo sapiens

<400> SEQUENCE: 18
gcgcgctctt tctcttcttt catctacgat tac                             33

<210> SEQ ID NO 19
<211> LENGTH: 6
<212> TYPE: PRT
<213> ORGANISM: Homo sapiens

<400> SEQUENCE: 19

Gln Ser Val Ser Ser Asn
1               5

<210> SEQ ID NO 20
<211> LENGTH: 18
<212> TYPE: DNA
<213> ORGANISM: Homo sapiens

<400> SEQUENCE: 20
cagagtgtta gcagcaac                                              18

<210> SEQ ID NO 21
<211> LENGTH: 3
<212> TYPE: PRT
<213> ORGANISM: Homo sapiens

<400> SEQUENCE: 21

Gly Ala Ser
1

<210> SEQ ID NO 22
<211> LENGTH: 9
<212> TYPE: DNA
<213> ORGANISM: Homo sapiens

<400> SEQUENCE: 22 ggtgcgtct                                                         9

<210> SEQ ID NO 23
<211> LENGTH: 9
<212> TYPE: PRT

```
<213> ORGANISM: Homo sapiens

<400> SEQUENCE: 23

Gln Gln Tyr Gly Arg Ser Pro Leu Thr
1               5

<210> SEQ ID NO 24
<211> LENGTH: 27
<212> TYPE: DNA
<213> ORGANISM: Homo sapiens

<400> SEQUENCE: 24
cagcagtatg gtaggtcacc gctcact                                         27

<210> SEQ ID NO 25
<211> LENGTH: 8
<212> TYPE: PRT
<213> ORGANISM: Homo sapiens

<400> SEQUENCE: 25

Gly Tyr Ser Phe Ser Asn Tyr Trp
1               5

<210> SEQ ID NO 26
<211> LENGTH: 24
<212> TYPE: DNA
<213> ORGANISM: Homo sapiens

<400> SEQUENCE: 26
ggatacagct ttagcaacta ctgg                                            24

<210> SEQ ID NO 27
<211> LENGTH: 8
<212> TYPE: PRT
<213> ORGANISM: Homo sapiens

<400> SEQUENCE: 27

Ile Tyr Pro Asp Asp Ser Asp Thr
1               5

<210> SEQ ID NO 28
<211> LENGTH: 24
<212> TYPE: DNA
<213> ORGANISM: Homo sapiens

<400> SEQUENCE: 28
atctatcctg atgactctga tacc                                            24

<210> SEQ ID NO 29
<211> LENGTH: 9
<212> TYPE: PRT
<213> ORGANISM: Homo sapiens

<400> SEQUENCE: 29

Val Arg Pro Arg Gly Ala Phe Asp Ile
1               5

<210> SEQ ID NO 30
<211> LENGTH: 27
<212> TYPE: DNA
<213> ORGANISM: Homo sapiens

<400> SEQUENCE: 30
gtgcgcccta gggggctttt gatatc                                          27
```

```
<210> SEQ ID NO 31
<211> LENGTH: 6
<212> TYPE: PRT
<213> ORGANISM: Homo sapiens

<400> SEQUENCE: 31

Gln Gly Val Gly Ile Asn
1               5

<210> SEQ ID NO 32
<211> LENGTH: 18
<212> TYPE: DNA
<213> ORGANISM: Homo sapiens

<400> SEQUENCE: 32
cagggtgttg gcatcaac                                              18

<210> SEQ ID NO 33
<211> LENGTH: 3
<212> TYPE: PRT
<213> ORGANISM: Homo sapiens

<400> SEQUENCE: 33

Asp Ala Ser
1

<210> SEQ ID NO 34
<211> LENGTH: 9
<212> TYPE: DNA
<213> ORGANISM: Homo sapiens

<400> SEQUENCE: 34 gatgcatcc                                                         9

<210> SEQ ID NO 35
<211> LENGTH: 9
<212> TYPE: PRT
<213> ORGANISM: Homo sapiens

<400> SEQUENCE: 35

Gln Gln Tyr Tyr Ser Phe Pro Trp Thr
1               5

<210> SEQ ID NO 36
<211> LENGTH: 27
<212> TYPE: DNA
<213> ORGANISM: Homo sapiens

<400> SEQUENCE: 36
cagcaatact atagttttcc gtggacg                                    27

<210> SEQ ID NO 37
<211> LENGTH: 8
<212> TYPE: PRT
<213> ORGANISM: Homo sapiens

<400> SEQUENCE: 37

Gly Tyr Ser Phe Ser Asn Tyr Trp
1               5

<210> SEQ ID NO 38
<211> LENGTH: 24
<212> TYPE: DNA
```

```
<213> ORGANISM: Homo sapiens

<400> SEQUENCE: 38
ggatacagct ttagcaacta ctgg                                          24

<210> SEQ ID NO 39
<211> LENGTH: 8
<212> TYPE: PRT
<213> ORGANISM: Homo sapiens

<400> SEQUENCE: 39

Ile Tyr Pro Asp Asp Ser Asp Thr
1               5

<210> SEQ ID NO 40
<211> LENGTH: 24
<212> TYPE: DNA
<213> ORGANISM: Homo sapiens

<400> SEQUENCE: 40
atctatcctg atgactctga tacc                                          24

<210> SEQ ID NO 41
<211> LENGTH: 9
<212> TYPE: PRT
<213> ORGANISM: Homo sapiens

<400> SEQUENCE: 41

Val Arg Pro Arg Gly Ala Phe Asp Ile
1               5

<210> SEQ ID NO 42
<211> LENGTH: 27
<212> TYPE: DNA
<213> ORGANISM: Homo sapiens

<400> SEQUENCE: 42
gtgcgcccta gggggcttt tgatatc                                        27

<210> SEQ ID NO 43
<211> LENGTH: 9
<212> TYPE: PRT
<213> ORGANISM: Homo sapiens

<400> SEQUENCE: 43

Ser Ser Asn Ile Gly Ala Gly His Ala
1               5

<210> SEQ ID NO 44
<211> LENGTH: 27
<212> TYPE: DNA
<213> ORGANISM: Homo sapiens

<400> SEQUENCE: 44
agctccaaca tcggggcagg tcatgct                                       27

<210> SEQ ID NO 45
<211> LENGTH: 3
<212> TYPE: PRT
<213> ORGANISM: Homo sapiens

<400> SEQUENCE: 45

Asp Asn Ala
1
```

```
<210> SEQ ID NO 46
<211> LENGTH: 9
<212> TYPE: DNA
<213> ORGANISM: Homo sapiens

<400> SEQUENCE: 46 gataacgcc                                                              9

<210> SEQ ID NO 47
<211> LENGTH: 11
<212> TYPE: PRT
<213> ORGANISM: Homo sapiens

<400> SEQUENCE: 47

Gly Thr Trp Asp Asp Ser Pro Ser Ala Tyr Val
1               5                   10

<210> SEQ ID NO 48
<211> LENGTH: 33
<212> TYPE: DNA
<213> ORGANISM: Homo sapiens

<400> SEQUENCE: 48
ggaacatggg atgacagccc gagtgcttat gtc                                   33

<210> SEQ ID NO 49
<211> LENGTH: 8
<212> TYPE: PRT
<213> ORGANISM: Homo sapiens

<400> SEQUENCE: 49

Gly Phe Thr Phe Ser Ser Tyr Trp
1               5

<210> SEQ ID NO 50
<211> LENGTH: 24
<212> TYPE: DNA
<213> ORGANISM: Homo sapiens

<400> SEQUENCE: 50
ggattcacct ttagtagcta ttgg                                             24

<210> SEQ ID NO 51
<211> LENGTH: 8
<212> TYPE: PRT
<213> ORGANISM: Homo sapiens

<400> SEQUENCE: 51

Ile Lys Gln Asp Gly Ser Glu Lys
1               5

<210> SEQ ID NO 52
<211> LENGTH: 24
<212> TYPE: DNA
<213> ORGANISM: Homo sapiens

<400> SEQUENCE: 52
ataaagcaag atggaagtga gaaa                                             24

<210> SEQ ID NO 53
<211> LENGTH: 11
<212> TYPE: PRT
<213> ORGANISM: Homo sapiens
```

<400> SEQUENCE: 53

Ala Arg Gly Ser Phe Ser Tyr Asp Ser Asp Leu
1               5                   10

<210> SEQ ID NO 54
<211> LENGTH: 33
<212> TYPE: DNA
<213> ORGANISM: Homo sapiens

<400> SEQUENCE: 54
gcgcgcggtt ctttctctta cgacagtgat ctg         33

<210> SEQ ID NO 55
<211> LENGTH: 11
<212> TYPE: PRT
<213> ORGANISM: Homo sapiens

<400> SEQUENCE: 55

Gln Ser Leu Val His Ser Asp Gly Asn Thr Tyr
1               5                   10

<210> SEQ ID NO 56
<211> LENGTH: 33
<212> TYPE: DNA
<213> ORGANISM: Homo sapiens

<400> SEQUENCE: 56
caaagcctcg ttcacagtga tggaaacacc tac         33

<210> SEQ ID NO 57
<211> LENGTH: 3
<212> TYPE: PRT
<213> ORGANISM: Homo sapiens

<400> SEQUENCE: 57

Lys Val Ser
1

<210> SEQ ID NO 58
<211> LENGTH: 9
<212> TYPE: DNA
<213> ORGANISM: Homo sapiens

<400> SEQUENCE: 58 aaagtttct                                    9

<210> SEQ ID NO 59
<211> LENGTH: 9
<212> TYPE: PRT
<213> ORGANISM: Homo sapiens

<400> SEQUENCE: 59

Met Gln Thr Thr His Trp Pro Pro Thr
1               5

<210> SEQ ID NO 60
<211> LENGTH: 27
<212> TYPE: DNA
<213> ORGANISM: Homo sapiens

<400> SEQUENCE: 60
atgcaaacca cacactggcc tccgacg                27

<210> SEQ ID NO 61
<211> LENGTH: 10
<212> TYPE: PRT
<213> ORGANISM: Homo sapiens

<400> SEQUENCE: 61

Gly Gly Ser Ile Ser Ser Gly Gly Tyr Tyr
1               5                   10

<210> SEQ ID NO 62
<211> LENGTH: 30
<212> TYPE: DNA
<213> ORGANISM: Homo sapiens

<400> SEQUENCE: 62
ggtggctcca tcagcagtgg tggttactac                                    30

<210> SEQ ID NO 63
<211> LENGTH: 7
<212> TYPE: PRT
<213> ORGANISM: Homo sapiens

<400> SEQUENCE: 63

Ile Tyr Tyr Ser Gly Ser Thr
1               5

<210> SEQ ID NO 64
<211> LENGTH: 21
<212> TYPE: DNA
<213> ORGANISM: Homo sapiens

<400> SEQUENCE: 64
atctattaca gtgggagcac c                                             21

<210> SEQ ID NO 65
<211> LENGTH: 13
<212> TYPE: PRT
<213> ORGANISM: Homo sapiens

<400> SEQUENCE: 65

Ala Arg Gly Gly Leu Tyr Trp Thr Tyr Ser Gln Asp Val
1               5                   10

<210> SEQ ID NO 66
<211> LENGTH: 39
<212> TYPE: DNA
<213> ORGANISM: Homo sapiens

<400> SEQUENCE: 66
gcgcgcggtg gtctgtactg gacttactct caggatgtt                          39

<210> SEQ ID NO 67
<211> LENGTH: 8
<212> TYPE: PRT
<213> ORGANISM: Homo sapiens

<400> SEQUENCE: 67

Ser Ser Asn Ile Gly Ser Asp Tyr
1               5

<210> SEQ ID NO 68
<211> LENGTH: 24
<212> TYPE: DNA
<213> ORGANISM: Homo sapiens

```
<400> SEQUENCE: 68
agctccaaca tcgggagtga ttat                                          24

<210> SEQ ID NO 69
<211> LENGTH: 3
<212> TYPE: PRT
<213> ORGANISM: Homo sapiens

<400> SEQUENCE: 69

Arg Asn Asp
1

<210> SEQ ID NO 70
<211> LENGTH: 9
<212> TYPE: DNA
<213> ORGANISM: Homo sapiens

<400> SEQUENCE: 70 aggaatgat                                                            9

<210> SEQ ID NO 71
<211> LENGTH: 11
<212> TYPE: PRT
<213> ORGANISM: Homo sapiens

<400> SEQUENCE: 71

Val Ala Trp Asp Asp Ser Leu Ser Gly Tyr Val
1               5                   10

<210> SEQ ID NO 72
<211> LENGTH: 33
<212> TYPE: DNA
<213> ORGANISM: Homo sapiens

<400> SEQUENCE: 72
gtagcatggg atgacagcct gagtggttat gtc                                33

<210> SEQ ID NO 73
<211> LENGTH: 8
<212> TYPE: PRT
<213> ORGANISM: Homo sapiens

<400> SEQUENCE: 73

Gly Phe Thr Phe Ser Asn Tyr Asp
1               5

<210> SEQ ID NO 74
<211> LENGTH: 24
<212> TYPE: DNA
<213> ORGANISM: Homo sapiens

<400> SEQUENCE: 74
ggattcacct tcagtaacta tgac                                          24

<210> SEQ ID NO 75
<211> LENGTH: 8
<212> TYPE: PRT
<213> ORGANISM: Homo sapiens

<400> SEQUENCE: 75

Ile Ser Tyr Asp Gly Ser Asn Asn
1               5
```

<210> SEQ ID NO 76
<211> LENGTH: 24
<212> TYPE: DNA
<213> ORGANISM: Homo sapiens

<400> SEQUENCE: 76
atatcatatg atggaagtaa taat                                          24

<210> SEQ ID NO 77
<211> LENGTH: 17
<212> TYPE: PRT
<213> ORGANISM: Homo sapiens

<400> SEQUENCE: 77

Ala Arg Ser Ser Ala Trp Val Gly Gly Gly Phe Leu Ser Gly Thr Asp
1               5                   10                  15

Asp

<210> SEQ ID NO 78
<211> LENGTH: 51
<212> TYPE: DNA
<213> ORGANISM: Homo sapiens

<400> SEQUENCE: 78
gcgcgctctt ctgcttgggt tggtggtggt ttcctgtctg gtactgatga c            51

<210> SEQ ID NO 79
<211> LENGTH: 7
<212> TYPE: PRT
<213> ORGANISM: Homo sapiens

<400> SEQUENCE: 79

Gln Ser Val Ser Ser Ser Tyr
1               5

<210> SEQ ID NO 80
<211> LENGTH: 21
<212> TYPE: DNA
<213> ORGANISM: Homo sapiens

<400> SEQUENCE: 80
cagagtgtta gcagcagcta c                                             21

<210> SEQ ID NO 81
<211> LENGTH: 3
<212> TYPE: PRT
<213> ORGANISM: Homo sapiens

<400> SEQUENCE: 81

Asp Thr Ser
1

<210> SEQ ID NO 82
<211> LENGTH: 9
<212> TYPE: DNA
<213> ORGANISM: Homo sapiens

<400> SEQUENCE: 82 gatacatcc                                                            9

<210> SEQ ID NO 83
<211> LENGTH: 10
<212> TYPE: PRT

<210> SEQ ID NO 83
<211> LENGTH: (not shown)
<212> TYPE: PRT
<213> ORGANISM: Homo sapiens

<400> SEQUENCE: 83

Leu His Tyr Gly Arg Ser Pro Pro Val Thr
1               5                   10

<210> SEQ ID NO 84
<211> LENGTH: 30
<212> TYPE: DNA
<213> ORGANISM: Homo sapiens

<400> SEQUENCE: 84
cttcactatg gtcgctcacc tccggtcact          30

<210> SEQ ID NO 85
<211> LENGTH: 8
<212> TYPE: PRT
<213> ORGANISM: Homo sapiens

<400> SEQUENCE: 85

Gly Phe Ser Leu Asn Asp Tyr Tyr
1               5

<210> SEQ ID NO 86
<211> LENGTH: 24
<212> TYPE: DNA
<213> ORGANISM: Homo sapiens

<400> SEQUENCE: 86
ggattcagcc tcaatgacta ttac          24

<210> SEQ ID NO 87
<211> LENGTH: 10
<212> TYPE: PRT
<213> ORGANISM: Homo sapiens

<400> SEQUENCE: 87

Ile Arg Asp Lys Ala His Gly Asp Thr Thr
1               5                   10

<210> SEQ ID NO 88
<211> LENGTH: 30
<212> TYPE: DNA
<213> ORGANISM: Homo sapiens

<400> SEQUENCE: 88
attagagaca aagctcacgg tgacaccaca          30

<210> SEQ ID NO 89
<211> LENGTH: 18
<212> TYPE: PRT
<213> ORGANISM: Homo sapiens

<400> SEQUENCE: 89

Ala Arg Trp Val Asp Asp Tyr Gln Gly Tyr Trp Ile Trp Ser Tyr His
1               5                   10                  15

Asp Phe

<210> SEQ ID NO 90
<211> LENGTH: 54
<212> TYPE: DNA
<213> ORGANISM: Homo sapiens

<400> SEQUENCE: 90
gcgcgctggg ttgacgacta ccagggttac tggatctggt cttaccacga tttc    54

<210> SEQ ID NO 91
<211> LENGTH: 11
<212> TYPE: PRT
<213> ORGANISM: Homo sapiens

<400> SEQUENCE: 91

Gln Ser Leu Ala Tyr Ser Asp Gly Asn Thr Tyr
1               5                   10

<210> SEQ ID NO 92
<211> LENGTH: 33
<212> TYPE: DNA
<213> ORGANISM: Homo sapiens

<400> SEQUENCE: 92
caaagcctcg catacagtga tggaaacacc tac    33

<210> SEQ ID NO 93
<211> LENGTH: 3
<212> TYPE: PRT
<213> ORGANISM: Homo sapiens

<400> SEQUENCE: 93

Lys Val Ser
1

<210> SEQ ID NO 94
<211> LENGTH: 9
<212> TYPE: DNA
<213> ORGANISM: Homo sapiens

<400> SEQUENCE: 94 aaggtttct    9

<210> SEQ ID NO 95
<211> LENGTH: 9
<212> TYPE: PRT
<213> ORGANISM: Homo sapiens

<400> SEQUENCE: 95

Met Gln Gly Thr His Trp Pro His Thr
1               5

<210> SEQ ID NO 96
<211> LENGTH: 27
<212> TYPE: DNA
<213> ORGANISM: Homo sapiens

<400> SEQUENCE: 96
atgcaaggta cacactggcc tcacact    27

<210> SEQ ID NO 97
<211> LENGTH: 8
<212> TYPE: PRT
<213> ORGANISM: Homo sapiens

<400> SEQUENCE: 97

Gly Phe Thr Phe Ser Ser Tyr Ala
1               5

<210> SEQ ID NO 98

```
<211> LENGTH: 24
<212> TYPE: DNA
<213> ORGANISM: Homo sapiens

<400> SEQUENCE: 98
ggattcacct ttagcagcta tgcc                                          24

<210> SEQ ID NO 99
<211> LENGTH: 8
<212> TYPE: PRT
<213> ORGANISM: Homo sapiens

<400> SEQUENCE: 99

Ile Ser Gly Ser Gly Gly Ser Thr
1               5

<210> SEQ ID NO 100
<211> LENGTH: 24
<212> TYPE: DNA
<213> ORGANISM: Homo sapiens

<400> SEQUENCE: 100
attagtggta gtggtggtag caca                                          24

<210> SEQ ID NO 101
<211> LENGTH: 9
<212> TYPE: PRT
<213> ORGANISM: Homo sapiens

<400> SEQUENCE: 101

Ala Arg His Tyr Tyr Ser Ser Asp Ser
1               5

<210> SEQ ID NO 102
<211> LENGTH: 27
<212> TYPE: DNA
<213> ORGANISM: Homo sapiens

<400> SEQUENCE: 102
gcgcgccatt actactcttc tgattct                                       27

<210> SEQ ID NO 103
<211> LENGTH: 6
<212> TYPE: PRT
<213> ORGANISM: Homo sapiens

<400> SEQUENCE: 103

Arg Leu Arg Glu Lys Tyr
1               5

<210> SEQ ID NO 104
<211> LENGTH: 18
<212> TYPE: DNA
<213> ORGANISM: Homo sapiens

<400> SEQUENCE: 104
agattgagag agaagtat                                                 18

<210> SEQ ID NO 105
<211> LENGTH: 3
<212> TYPE: PRT
<213> ORGANISM: Homo sapiens

<400> SEQUENCE: 105
```

```
Glu Asp Thr
1

<210> SEQ ID NO 106
<211> LENGTH: 9
<212> TYPE: DNA
<213> ORGANISM: Homo sapiens

<400> SEQUENCE: 106 gaagatact                                                                  9

<210> SEQ ID NO 107
<211> LENGTH: 8
<212> TYPE: PRT
<213> ORGANISM: Homo sapiens

<400> SEQUENCE: 107

Gln Ala Trp Asp Ser Ser Val Ile
1               5

<210> SEQ ID NO 108
<211> LENGTH: 24
<212> TYPE: DNA
<213> ORGANISM: Homo sapiens

<400> SEQUENCE: 108
caggcgtggg acagcagcgt gatt                                                24

<210> SEQ ID NO 109
<211> LENGTH: 8
<212> TYPE: PRT
<213> ORGANISM: Homo sapiens

<400> SEQUENCE: 109

Gly Tyr Thr Phe Thr Ser Tyr Tyr
1               5

<210> SEQ ID NO 110
<211> LENGTH: 24
<212> TYPE: DNA
<213> ORGANISM: Homo sapiens

<400> SEQUENCE: 110
ggatacacct tcaccagcta ctat                                                24

<210> SEQ ID NO 111
<211> LENGTH: 8
<212> TYPE: PRT
<213> ORGANISM: Homo sapiens

<400> SEQUENCE: 111

Ile Asn Pro Ser Gly Gly Ser Thr
1               5

<210> SEQ ID NO 112
<211> LENGTH: 24
<212> TYPE: DNA
<213> ORGANISM: Homo sapiens

<400> SEQUENCE: 112
atcaacccta gtggtggtag caca                                                24

<210> SEQ ID NO 113
<211> LENGTH: 13
```

```
<212> TYPE: PRT
<213> ORGANISM: Homo sapiens

<400> SEQUENCE: 113

Ala Arg Gly Gly Tyr Thr Gly Trp Ser Pro Ser Asp Pro
1               5                   10

<210> SEQ ID NO 114
<211> LENGTH: 39
<212> TYPE: DNA
<213> ORGANISM: Homo sapiens

<400> SEQUENCE: 114
gcgcgcggtg gttacactgg ttggtctccg tctgatccg                              39

<210> SEQ ID NO 115
<211> LENGTH: 9
<212> TYPE: PRT
<213> ORGANISM: Homo sapiens

<400> SEQUENCE: 115

Ser Ser Asp Val Gly Gly Tyr Asn Tyr
1               5

<210> SEQ ID NO 116
<211> LENGTH: 27
<212> TYPE: DNA
<213> ORGANISM: Homo sapiens

<400> SEQUENCE: 116
agcagtgacg ttggtggtta taactat                                          27

<210> SEQ ID NO 117
<211> LENGTH: 3
<212> TYPE: PRT
<213> ORGANISM: Homo sapiens

<400> SEQUENCE: 117

Asp Val Ser
1

<210> SEQ ID NO 118
<211> LENGTH: 9
<212> TYPE: DNA
<213> ORGANISM: Homo sapiens

<400> SEQUENCE: 118 gatgtcagt                                                               9

<210> SEQ ID NO 119
<211> LENGTH: 10
<212> TYPE: PRT
<213> ORGANISM: Homo sapiens

<400> SEQUENCE: 119

Gly Ser Phe Thr Ser Ser Ile Thr Tyr Val
1               5                   10

<210> SEQ ID NO 120
<211> LENGTH: 30
<212> TYPE: DNA
<213> ORGANISM: Homo sapiens

<400> SEQUENCE: 120
```

```
ggctcattta caagcagcat cacttatgtc                                    30
```

<210> SEQ ID NO 121
<211> LENGTH: 8
<212> TYPE: PRT
<213> ORGANISM: Homo sapiens

<400> SEQUENCE: 121

Gly Tyr Thr Phe Thr Ser Tyr Gly
1               5

<210> SEQ ID NO 122
<211> LENGTH: 24
<212> TYPE: DNA
<213> ORGANISM: Homo sapiens

<400> SEQUENCE: 122

```
ggttacacct ttaccagcta tggt                                          24
```

<210> SEQ ID NO 123
<211> LENGTH: 8
<212> TYPE: PRT
<213> ORGANISM: Homo sapiens

<400> SEQUENCE: 123

Ile Ser Ala Tyr Asn Gly Asn Thr
1               5

<210> SEQ ID NO 124
<211> LENGTH: 24
<212> TYPE: DNA
<213> ORGANISM: Homo sapiens

<400> SEQUENCE: 124

```
atcagcgctt acaatggtaa caca                                          24
```

<210> SEQ ID NO 125
<211> LENGTH: 16
<212> TYPE: PRT
<213> ORGANISM: Homo sapiens

<400> SEQUENCE: 125

Ala Arg His Leu Gly Pro Met Gly Met Tyr Asp Trp Ser Phe Asp Lys
1               5                   10                  15

<210> SEQ ID NO 126
<211> LENGTH: 48
<212> TYPE: DNA
<213> ORGANISM: Homo sapiens

<400> SEQUENCE: 126

```
gcgcgccatc tgggtccgat gggtatgtac gactggtctt tcgataaa              48
```

<210> SEQ ID NO 127
<211> LENGTH: 6
<212> TYPE: PRT
<213> ORGANISM: Homo sapiens

<400> SEQUENCE: 127

Asn Ile Gly Arg Lys Ser
1               5

<210> SEQ ID NO 128
<211> LENGTH: 18

```
<212> TYPE: DNA
<213> ORGANISM: Homo sapiens

<400> SEQUENCE: 128
aacattggac gtaaaagt                                              18

<210> SEQ ID NO 129
<211> LENGTH: 3
<212> TYPE: PRT
<213> ORGANISM: Homo sapiens

<400> SEQUENCE: 129

Tyr Asp Ser
1

<210> SEQ ID NO 130
<211> LENGTH: 9
<212> TYPE: DNA
<213> ORGANISM: Homo sapiens

<400> SEQUENCE: 130 tatgatagc                                                         9

<210> SEQ ID NO 131
<211> LENGTH: 11
<212> TYPE: PRT
<213> ORGANISM: Homo sapiens

<400> SEQUENCE: 131

Gln Val Trp Asp Arg Ser Ser Asp Leu Tyr Val
1               5                   10

<210> SEQ ID NO 132
<211> LENGTH: 33
<212> TYPE: DNA
<213> ORGANISM: Homo sapiens

<400> SEQUENCE: 132
caggtgtggg atcgtagtag tgacctttat gtc                             33

<210> SEQ ID NO 133
<211> LENGTH: 10
<212> TYPE: PRT
<213> ORGANISM: Homo sapiens

<400> SEQUENCE: 133

Gly Phe Ser Leu Ser Thr Ser Gly Met Ser
1               5                   10

<210> SEQ ID NO 134
<211> LENGTH: 30
<212> TYPE: DNA
<213> ORGANISM: Homo sapiens

<400> SEQUENCE: 134
gggttctcac tcagcactag tggaatgtct                                 30

<210> SEQ ID NO 135
<211> LENGTH: 7
<212> TYPE: PRT
<213> ORGANISM: Homo sapiens

<400> SEQUENCE: 135

Ile Asp Trp Asp Asp Asp Lys
```

<210> SEQ ID NO 136
<211> LENGTH: 21
<212> TYPE: DNA
<213> ORGANISM: Homo sapiens

<400> SEQUENCE: 136
attgattggg atgatgataa a                                              21

<210> SEQ ID NO 137
<211> LENGTH: 13
<212> TYPE: PRT
<213> ORGANISM: Homo sapiens

<400> SEQUENCE: 137

Ala Arg Gly Phe Tyr Leu Ala Tyr Gly Ser Tyr Asp Ser
1               5                   10

<210> SEQ ID NO 138
<211> LENGTH: 39
<212> TYPE: DNA
<213> ORGANISM: Homo sapiens

<400> SEQUENCE: 138
gcgcgcggtt tctacctggc ttacggttct tacgattct                           39

<210> SEQ ID NO 139
<211> LENGTH: 9
<212> TYPE: PRT
<213> ORGANISM: Homo sapiens

<400> SEQUENCE: 139

Ser Gly Asp Val Gly Gly Tyr Asn Tyr
1               5

<210> SEQ ID NO 140
<211> LENGTH: 27
<212> TYPE: DNA
<213> ORGANISM: Homo sapiens

<400> SEQUENCE: 140
agcggtgacg ttggcggtta taactat                                        27

<210> SEQ ID NO 141
<211> LENGTH: 3
<212> TYPE: PRT
<213> ORGANISM: Homo sapiens

<400> SEQUENCE: 141

Asp Val Asn
1

<210> SEQ ID NO 142
<211> LENGTH: 9
<212> TYPE: DNA
<213> ORGANISM: Homo sapiens

<400> SEQUENCE: 142 gatgtcaat                                                             9

<210> SEQ ID NO 143
<211> LENGTH: 9
<212> TYPE: PRT

<213> ORGANISM: Homo sapiens

<400> SEQUENCE: 143

Ser Ser Tyr Thr Ser Thr Ser Thr Val
1               5

<210> SEQ ID NO 144
<211> LENGTH: 27
<212> TYPE: DNA
<213> ORGANISM: Homo sapiens

<400> SEQUENCE: 144
agctcatata caagcaccag caccgtc                                          27

<210> SEQ ID NO 145
<211> LENGTH: 8
<212> TYPE: PRT
<213> ORGANISM: Homo sapiens

<400> SEQUENCE: 145

Gly Tyr Thr Phe Thr Asn Tyr Tyr
1               5

<210> SEQ ID NO 146
<211> LENGTH: 24
<212> TYPE: DNA
<213> ORGANISM: Homo sapiens

<400> SEQUENCE: 146
ggatacacct tcaccaatta ctat                                             24

<210> SEQ ID NO 147
<211> LENGTH: 8
<212> TYPE: PRT
<213> ORGANISM: Homo sapiens

<400> SEQUENCE: 147

Ile Asn Pro Thr Ser Gly Arg Thr
1               5

<210> SEQ ID NO 148
<211> LENGTH: 24
<212> TYPE: DNA
<213> ORGANISM: Homo sapiens

<400> SEQUENCE: 148
atcaacccta caagtggtag gaca                                             24

<210> SEQ ID NO 149
<211> LENGTH: 13
<212> TYPE: PRT
<213> ORGANISM: Homo sapiens

<400> SEQUENCE: 149

Ala Arg Ser Gly Tyr Tyr Trp Gly Val Asn Gly Asp Gln
1               5                   10

<210> SEQ ID NO 150
<211> LENGTH: 39
<212> TYPE: DNA
<213> ORGANISM: Homo sapiens

<400> SEQUENCE: 150
gcgcgctctg gttactactg gggtgttaac ggtgatcag                             39

<210> SEQ ID NO 151
<211> LENGTH: 6
<212> TYPE: PRT
<213> ORGANISM: Homo sapiens

<400> SEQUENCE: 151

Asn Ile Gly Ser Lys Asn
1               5

<210> SEQ ID NO 152
<211> LENGTH: 18
<212> TYPE: DNA
<213> ORGANISM: Homo sapiens

<400> SEQUENCE: 152
aacattggaa gtaaaaat                                                   18

<210> SEQ ID NO 153
<211> LENGTH: 3
<212> TYPE: PRT
<213> ORGANISM: Homo sapiens

<400> SEQUENCE: 153

Arg Asp Ser
1

<210> SEQ ID NO 154
<211> LENGTH: 9
<212> TYPE: DNA
<213> ORGANISM: Homo sapiens

<400> SEQUENCE: 154 agggatagc                                                              9

<210> SEQ ID NO 155
<211> LENGTH: 9
<212> TYPE: PRT
<213> ORGANISM: Homo sapiens

<400> SEQUENCE: 155

Gln Val Trp Asp Ser Ser Ile Val Val
1               5

<210> SEQ ID NO 156
<211> LENGTH: 27
<212> TYPE: DNA
<213> ORGANISM: Homo sapiens

<400> SEQUENCE: 156
caggtgtggg acagcagtat tgtggta                                         27

<210> SEQ ID NO 157
<211> LENGTH: 327
<212> TYPE: DNA
<213> ORGANISM: Homo sapiens

<400> SEQUENCE: 157
tcttctgagc tgactcagga ccctgctgtg tctgtggcct tgggacagac agtcaggatc     60
acatgccaag agacagcct cagaagctat tatgcaagct ggtaccagca gaagccagga    120
caggcccctg tacttgtcat ctatggtaaa acaaccggc cctcagggat cccagaccga    180
ttctctggct ccagctcagg aaacacagct tccttgacca tcactggggc tcaggcggaa    240
gatgaggctg actattactg taactcccgg gacagcagtg gtaaccatct ggtattcggc    300
ggagggacca agctgaccgt cctaggt                                       327

<210> SEQ ID NO 158
<211> LENGTH: 109
<212> TYPE: PRT
<213> ORGANISM: Homo sapiens

<400> SEQUENCE: 158

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Lys Leu Thr Val Leu Gly
            100                 105

<210> SEQ ID NO 159
<211> LENGTH: 363
<212> TYPE: DNA
<213> ORGANISM: Homo sapiens

<400> SEQUENCE: 159
gaggtccagc tggtacagtc tggggctgag gtgaagaagc ctggggcctc agtgaaggtc    60
tcctgcaagg cttctggata caccttcacc gactactata tacactgggt gcggcaggcc   120
cctggacaag gctggagtg gatgggatgg atgaacccta acagtgggaa ctcagtctct   180
gcacagaagt tccagggcag agtcaccatg accaggata cctccataaa cacagcctac   240
atggagctga gcagcctgac atctgacgac acggccgtgt attactgtgc gcgcaactct   300
gaatggcatc cgtggggtta ctacgattac tggggtcaag gtactctggt gaccgtctcc   360
tca                                                                  363

<210> SEQ ID NO 160
<211> LENGTH: 121
<212> TYPE: PRT
<213> ORGANISM: Homo sapiens

<400> SEQUENCE: 160

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Met Asn Pro Asn Ser Gly Asn Ser Val Ser Ala Gln Lys Phe
    50                  55                  60

Gln Gly Arg Val Thr Met Thr Arg Asp Thr Ser Ile Asn Thr Ala Tyr
65                  70                  75                  80

```
Met Glu Leu Ser Ser Leu Thr Ser Asp Asp Thr Ala Val Tyr Tyr Cys
                85                  90                  95

Ala Arg Asn Ser Glu Trp His Pro Trp Gly Tyr Tyr Tyr Trp Gly
            100                 105                 110

Gln Gly Thr Leu Val Thr Val Ser Ser
        115                 120

<210> SEQ ID NO 161
<211> LENGTH: 324
<212> TYPE: DNA
<213> ORGANISM: Homo sapiens

<400> SEQUENCE: 161
gaaacgacac tcacgcagtc tccaggcacc ctgtctgtgt ctccagggga aagagccacc    60
ctctcctgca gggccagtca gagtgttagc agcaacttag cctggtacca gcagaaacgt   120
ggccaggctc ccaggctcct catctatggt gcgtctaccc gggccactgg tatcccagtc   180
aggttcagtg gcagtgggtc tgggacagag ttcactctca ccatcagcag attggagcct   240
gaagattttg cagtgtatta ctgtcagcag tatggtaggt caccgctcac tttcggcgga   300
gggaccaaag tggatatcaa acgt                                          324

<210> SEQ ID NO 162
<211> LENGTH: 108
<212> TYPE: PRT
<213> ORGANISM: Homo sapiens

<400> SEQUENCE: 162

Glu Thr Thr Leu Thr Gln Ser Pro Gly Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Arg Gly Gln Ala Pro Arg Leu Leu Ile
        35                  40                  45

Tyr Gly Ala Ser Thr Arg Ala Thr Gly Ile Pro Val Arg Phe Ser Gly
    50                  55                  60

Ser Gly Ser Gly Thr Glu Phe Thr Leu Thr Ile Ser Arg Leu Glu Pro
65                  70                  75                  80

Glu Asp Phe Ala Val Tyr Tyr Cys Gln Gln Tyr Gly Arg Ser Pro Leu
                85                  90                  95

Thr Phe Gly Gly Gly Thr Lys Val Asp Ile Lys Arg
            100                 105

<210> SEQ ID NO 163
<211> LENGTH: 354
<212> TYPE: DNA
<213> ORGANISM: Homo sapiens

<400> SEQUENCE: 163
gaagtgcagc tggtgcagtc tggagcagag gtgaaaaagc ccggggagtc tctgaagatc    60
tcctgtcagg gttctggata caggttcagc aagtactgga tcggctgggt gcgccagatg   120
cccgggaaag gcctggagtg gatggggatc atctatcctg gtgactctga taccagatac   180
agcccgtcct tccaaggcca ggtcaccatc tcagccgaca gtccatcagc acccgcctac   240
ctgcagtgga gcagcctgaa ggcctcggac accgccatgt attactgtgc gcgctctttc   300
tcttctttca tctacgatta ctggggtcaa ggtactctgg tgaccgtctc ctca         354
```

```
<210> SEQ ID NO 164
<211> LENGTH: 118
<212> TYPE: PRT
<213> ORGANISM: Homo sapiens

<400> SEQUENCE: 164

Glu Val Gln Leu Val Gln Ser Gly Ala Glu Val Lys Lys Pro Gly Glu
1               5                   10                  15

Ser Leu Lys Ile Ser Cys Gln Gly Ser Gly Tyr Arg Phe Ser Lys Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Phe Ser Ser Phe Ile Tyr Asp Tyr Trp Gly Gln Gly Thr
            100                 105                 110

Leu Val Thr Val Ser Ser
        115

<210> SEQ ID NO 165
<211> LENGTH: 324
<212> TYPE: DNA
<213> ORGANISM: Homo sapiens

<400> SEQUENCE: 165
gaaattgtga tgacacagtc tccagccacc ctgtctgtgt ctccagggga aagtgccacc    60
ctctcctgca gggccagtca gggtgttggc atcaacttag cctggtacca gcagagacct   120
ggccagcctc ccaggctcct catctatgat gcatccaaca gggccactgg catcccagcc   180
aggttcagtg gcagtgggtc tgggacagat ttcactctca ccatcagcag cctgcaggct   240
gaagatgtgg cagtctatta ctgtcagcaa tactatagtt ttccgtggac gttcggccag   300
gggaccaagg tggaaatcaa acgt                                          324

<210> SEQ ID NO 166
<211> LENGTH: 108
<212> TYPE: PRT
<213> ORGANISM: Homo sapiens

<400> SEQUENCE: 166

Glu Ile Val Met Thr Gln Ser Pro Ala Thr Leu Ser Val Ser Pro Gly
1               5                   10                  15

Glu Ser Ala Thr Leu Ser Cys Arg Ala Ser Gln Gly Val Gly Ile Asn
            20                  25                  30

Leu Ala Trp Tyr Gln Gln Arg Pro Gly Gln Pro Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Tyr Ser Phe Pro Trp
                85                  90                  95

Thr Phe Gly Gln Gly Thr Lys Val Glu Ile Lys Arg
            100                 105
```

-continued

<210> SEQ ID NO 167
<211> LENGTH: 348
<212> TYPE: DNA
<213> ORGANISM: Homo sapiens

<400> SEQUENCE: 167

```
gaggtgcagc tggtgcagtc tggggcagag gtgaaaaagc ccggggagtc tctgaaaatc      60
tcctgtaagg cttctggata cagctttagc aactactgga tcggctgggt gcgccagatg     120
cccgggaaag gcctggagtg gatggggatc atctatcctg atgactctga taccagatac     180
agcccgtccg tccaaggcca ggtcaccatc tcagccgaca gtccatcag caccgcctac      240
ctgcagtggt acagcctgaa ggtcgcggac accgccaaat attactgtgt gcgccctagg     300
ggggcttttg atatctgggg ccaagggacc acggtcaccg tctcctca                  348
```

<210> SEQ ID NO 168
<211> LENGTH: 116
<212> TYPE: PRT
<213> ORGANISM: Homo sapiens

<400> SEQUENCE: 168

```
Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Val
    50                  55                  60

Gln Gly Gln Val Thr Ile Ser Ala Asp Lys Ser Ile Ser Thr Ala Tyr
65                  70                  75                  80

Leu Gln Trp Tyr Ser Leu Lys Val Ala Asp Thr Ala Lys Tyr Tyr Cys
                85                  90                  95

Val Arg Pro Arg Gly Ala Phe Asp Ile Trp Gly Gln Gly Thr Thr Val
            100                 105                 110

Thr Val Ser Ser
        115
```

<210> SEQ ID NO 169
<211> LENGTH: 336
<212> TYPE: DNA
<213> ORGANISM: Homo sapiens

<400> SEQUENCE: 169

```
cagtctgtgc tgacgcagcc gccctcagtg tctggggccc agggcagag ggtcacgatc       60
tcctgcactg ggagtagctc aacatcgggg gcaggtcatg ctgtacactg gtaccagcaa     120
cttccaggaa cagcccccaa actcctcatc tatgataacg ccaatcggcc tcaggggtc      180
cctgaccgat tctctggctc ccagtctggc acttcagcct cctggccat caccggactc      240
cagactgggg acgaggccga ttattactgc ggaacatggg atgacagccc gagtgcttat    300
gtcttcggaa ctgggaccaa ggtcaccgtc ctaggt                                336
```

<210> SEQ ID NO 170
<211> LENGTH: 112
<212> TYPE: PRT
<213> ORGANISM: Homo sapiens -continued

<400> SEQUENCE: 170

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

His Ala Val His Trp Tyr Gln Gln Leu Pro Gly Thr Ala Pro Lys Leu
        35                  40                  45

Leu Ile Tyr Asp Asn Ala Asn Arg Pro Ser Gly Val Pro Asp Arg Phe
    50                  55                  60

Ser Gly Ser Gln Ser Gly Thr Ser Ala Ser Leu Ala Ile Thr Gly Leu
65                  70                  75                  80

Gln Thr Gly Asp Glu Ala Asp Tyr Tyr Cys Gly Thr Trp Asp Asp Ser
                85                  90                  95

Pro Ser Ala Tyr Val Phe Gly Thr Gly Thr Lys Val Thr Val Leu Gly
            100                 105                 110

<210> SEQ ID NO 171
<211> LENGTH: 348
<212> TYPE: DNA
<213> ORGANISM: Homo sapiens

<400> SEQUENCE: 171
caggtgcagc tggtggagtc tggggcagag gtgaaaaagc ccggggagtc tctgaaaatc      60
tcctgtaagg cttctggata cagctttagc aactactgga tcggctgggt gcgccagatg     120
cccgggaaag gcctggagtg gatggggatc atctatcctg atgactctga taccagatac     180
agcccgtcct tccaaggcca ggtcaccatc tcagccgaca gtccatcag caccgcctac      240 ctgcagtggt acagcctgaa ggtcgcggac accgccaaat attactgtgt gcgccctagg     300
ggggcttttg atatctgggg ccaagggacc acggtcaccg tctcctca                  348

<210> SEQ ID NO 172
<211> LENGTH: 116
<212> TYPE: PRT
<213> ORGANISM: Homo sapiens

<400> SEQUENCE: 172

Gln Val Gln Leu Val Glu Ser Gly Ala Glu Val Lys Lys Pro Gly Glu
1               5                   10                  15

Ser Leu Lys Ile Ser Cys Lys Ala Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Tyr Ser Leu Lys Val Ala Asp Thr Ala Lys Tyr Tyr Cys
                85                  90                  95

Val Arg Pro Arg Gly Ala Phe Asp Ile Trp Gly Gln Gly Thr Thr Val
            100                 105                 110

Thr Val Ser Ser
        115

<210> SEQ ID NO 173
<211> LENGTH: 339
<212> TYPE: DNA

<213> ORGANISM: Homo sapiens

<400> SEQUENCE: 173

```
gatgttgtga tgactcagtc tccactctcc ctgcccgtca cccttggaca gccggcctcc      60
atctcctgca ggtctagtca aagcctcgtt cacagtgatg gaaacaccta cttgaattgg     120
tttcagcaga ggccaggcca atctccaagg cgcctaattt ataaagtttc tagccgggac     180
tctggggtcc cagatagatt cagcggcact gggtcaggca ctgatttcac actgaaaatc     240
agcagggtgg aggctgaaga tgttggcgtt tattactgca tgcaaaccac acactggcct     300
ccgacgttcg gccaagggac caaggtggag atcaaacgt                            339
```

<210> SEQ ID NO 174
<211> LENGTH: 113
<212> TYPE: PRT
<213> ORGANISM: Homo sapiens

<400> SEQUENCE: 174

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Ser Arg Asp Ser Gly Val Pro
    50                  55                  60

Asp Arg Phe Ser Gly Thr Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr His Trp Pro Pro Thr Phe Gly Gln Gly Thr Lys Val Glu Ile Lys
            100                 105                 110

Arg

<210> SEQ ID NO 175
<211> LENGTH: 354
<212> TYPE: DNA
<213> ORGANISM: Homo sapiens

<400> SEQUENCE: 175

```
caggtgcagc tggtggagtc tgggggaggc ttggtccagc ctggggggtc cctgagactc      60
tcctgtgcag cctctggatt cacctttagt agctattgga tgagctgggt ccgccaggct     120
ccagggaaag gctggagtg gtggccaac ataaagcaag atggaagtga aaatactat        180
gtggactctg tgaggggccg attcaccatc tccagagaca cgccaagaa ctcactgtat      240
ctgcaaatga acagcctgag agccgaggac accgccatgt attactgtgc gcgcggttct     300
ttctcttacg acagtgatct gtggggtcaa ggtactctgg tgaccgtctc ctca           354
```

<210> SEQ ID NO 176
<211> LENGTH: 118
<212> TYPE: PRT
<213> ORGANISM: Homo sapiens

<400> SEQUENCE: 176

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
                20                  25                  30
Trp Met Ser Trp Val Arg Gln Ala Pro Gly Lys Gly Leu Glu Trp Val
            35                  40                  45
Ala Asn Ile Lys Gln Asp Gly Ser Glu Lys Tyr Tyr Val Asp Ser Val
        50                  55                  60
Arg Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Met Tyr Tyr Cys
                85                  90                  95
Ala Arg Gly Ser Phe Ser Tyr Asp Ser Asp Leu Trp Gly Gln Gly Thr
            100                 105                 110
Leu Val Thr Val Ser Ser
        115

<210> SEQ ID NO 177
<211> LENGTH: 333
<212> TYPE: DNA
<213> ORGANISM: Homo sapiens

<400> SEQUENCE: 177
cagcctgtgc tgactcagcc accctcagcg tctgggaccc ccgggcagag ggtcaccatc      60
tcttgttctg gaagcagctc aacatcggg agtgattatg tatcctggta ccaacagctc     120
ccaggaacgg ccccccaaact cctcatctat aggaatgatc agcggccctc aggggtccct     180
gaccgattct ctggctccaa gtctggcacc tcagcctccc tggccatcag tgggctccgg     240
tccgaggatg aggctgatta ttactgtgta gcatgggatg acagcctgag tggttatgtc     300
ttcggaagtg ggaccaaggt caccgtccta ggt                                   333

<210> SEQ ID NO 178
<211> LENGTH: 111
<212> TYPE: PRT
<213> ORGANISM: Homo sapiens

<400> SEQUENCE: 178

Gln Pro Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asp
            20                  25                  30
Tyr Val Ser Trp Tyr Gln Gln Leu Pro Gly Thr Ala Pro Lys Leu Leu
        35                  40                  45
Ile Tyr Arg Asn Asp Gln Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Val Ala Trp Asp Asp Ser Leu
                85                  90                  95
Ser Gly Tyr Val Phe Gly Ser Gly Thr Lys Val Thr Val Leu Gly
            100                 105                 110

<210> SEQ ID NO 179
<211> LENGTH: 363
<212> TYPE: DNA
<213> ORGANISM: Homo sapiens

<400> SEQUENCE: 179
gaggtgcagc tggtggagtc tggcccagga ctggtgaagc cttcacagac cctgtccctc      60
```

```
acctgcactg tctctggtgg ctccatcagc agtggtggtt actactggag ctggatccgc    120
cagcacccag ggaagggcct ggagtggatt gggtacatct attacagtgg gagcacctac    180
tacaacccgt ccctcaagag tcgagttacc atatcagtag acacgtccaa gaaccagttc    240
tccctgaagc tgagctctgt gaccgctgcg gacaccgcca tgtattactg tgcgcgcggt    300
ggtctgtact ggacttactc tcaggatgtt tggggtcaag gtactctggt gaccgtctcc    360
tca                                                                    363
```

```
<210> SEQ ID NO 180
<211> LENGTH: 121
<212> TYPE: PRT
<213> ORGANISM: Homo sapiens

<400> SEQUENCE: 180
```

Glu Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Met Tyr Tyr
                85                  90                  95

Cys Ala Arg Gly Gly Leu Tyr Trp Thr Tyr Ser Gln Asp Val Trp Gly
            100                 105                 110

Gln Gly Thr Leu Val Thr Val Ser Ser
        115                 120

```
<210> SEQ ID NO 181
<211> LENGTH: 330
<212> TYPE: DNA
<213> ORGANISM: Homo sapiens
<400> SEQUENCE: 181
gaaattgtga tgacgcagtc tccagccacc ctgtctttgt ctccagggga aagagccacc    60
ctctcctgcg gggccagtca gagtgttagc agcagctact tagcctggta ccagcagaaa   120
cctggcctgg cgcccaggct cctcatctat gatacatcca aagggccac tggcatccca   180 gacaggttca gtggcagtgg gtctgggaca gacttcactc tcaccatcag cagactggag   240
ccggaagatt ttgcagtgta ttactgtctt cactatggtc gctcacctcc ggtcactttc   300
ggcggaggga ccaaggtgga gatcaaacgt                                       330
```

```
<210> SEQ ID NO 182
<211> LENGTH: 110
<212> TYPE: PRT
<213> ORGANISM: Homo sapiens

<400> SEQUENCE: 182
```

Glu Ile Val Met Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Leu Ala Pro Arg Leu Leu

```
                35                  40                  45
Ile Tyr Asp Thr Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Leu His Tyr Gly Arg Ser Pro
                 85                  90                  95

Pro Val Thr Phe Gly Gly Gly Thr Lys Val Glu Ile Lys Arg
            100                 105                 110

<210> SEQ ID NO 183
<211> LENGTH: 372
<212> TYPE: DNA
<213> ORGANISM: Homo sapiens

<400> SEQUENCE: 183
cagatgcagc tggtgcagtc tgggggaggc gtggtccagc ctgggaggtc cctgagactc     60
tcctgtgcag cctctggatt caccttcagt aactatgaca tgcactgggt ccgccgggct    120
ccaggcaagg ggctggagtg ggtggcagtt atatcatatg atggaagtaa taattactat    180
gcagactccg tgaagggccg attcaccatc tccagagaca attccaagaa cacgctgtat    240
ctgcaaatga acagcctgag agctgaggac acggccgtgt attactgtgc gcgctcttct    300
gcttgggttg gtggtggttt cctgtctggt actgatgact ggggtcaagg tactctggtg    360
accgtctcct ca                                                        372

<210> SEQ ID NO 184
<211> LENGTH: 124
<212> TYPE: PRT
<213> ORGANISM: Homo sapiens

<400> SEQUENCE: 184

Gln Met Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
                20                  25                  30

Asp Met His Trp Val Arg Arg Ala Pro Gly Lys Gly Leu Glu Trp Val
            35                  40                  45

Ala Val Ile Ser Tyr Asp Gly Ser Asn Asn Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ser Ser Ala Trp Val Gly Gly Gly Phe Leu Ser Gly Thr Asp
            100                 105                 110

Asp Trp Gly Gln Gly Thr Leu Val Thr Val Ser Ser
        115                 120

<210> SEQ ID NO 185
<211> LENGTH: 339
<212> TYPE: DNA
<213> ORGANISM: Homo sapiens

<400> SEQUENCE: 185
gaaattgtgc tgactcagtc tccactctcc ctgcccgtca cccttggaca gccggcctcc     60
atctcctgca ggtctagtca aagcctcgca tacagtgatg gaaacaccta cttgaattgg    120
```

```
tttcaccaga ggccaggcca atctccaagg cgcctaatct ataaggtttc taagcgggac      180
tctggggtcc cagacagatt cagcggcagt gggtcaggca ctgatttcac actgagaatc      240
agcagggtgg aggctgagga tgttgggatt tattactgca tgcaaggtac acactggcct      300
cacactttcg gccctgggac caaagtggat atcaaacgt                             339
```

<210> SEQ ID NO 186
<211> LENGTH: 113
<212> TYPE: PRT
<213> ORGANISM: Homo sapiens

<400> SEQUENCE: 186

Glu Ile Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Tyr Ser
            20                  25                  30

Asp Gly Asn Thr Tyr Leu Asn Trp Phe His Gln Arg Pro Gly Gln Ser
        35                  40                  45

Pro Arg Arg Leu Ile Tyr Lys Val Ser Lys Arg Asp Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Gly
                85                  90                  95

Thr His Trp Pro His Thr Phe Gly Pro Gly Thr Lys Val Asp Ile Lys
            100                 105                 110

Arg

<210> SEQ ID NO 187
<211> LENGTH: 381
<212> TYPE: DNA
<213> ORGANISM: Homo sapiens

<400> SEQUENCE: 187

```
gaagtgcagc tggtgcagtc tgggggaggc ttggtccagc ctggagggtc cctgagactc      60
tcctgtgcag cctctggatt cagcctcaat gactattaca tggactgggt ccgccaggct      120
ccaggggagg ggctggagtg ggttggccgt attagagaca agctcacgg tgacaccaca      180 gaatacatcg cgtctgtgaa agacagattt atcgtctcaa gagatgactc caagaactca      240
ctgtatctgc aaatgaacag cctgaaaacc gaggacaccg ccatgtatta ctgtgcgcgc      300
tgggttgacg actaccaggg ttactggatc tggtcttacc acgatttctg gggtcaaggt      360
actctggtga ccgtctcctc a                                                381
```

<210> SEQ ID NO 188
<211> LENGTH: 127
<212> TYPE: PRT
<213> ORGANISM: Homo sapiens

<400> SEQUENCE: 188

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Ser Leu Asn Asp Tyr
            20                  25                  30

Tyr Met Asp Trp Val Arg Gln Ala Pro Gly Glu Gly Leu Glu Trp Val
        35                  40                  45

Gly Arg Ile Arg Asp Lys Ala His Gly Asp Thr Thr Glu Tyr Ile Ala
        50                  55                  60

Ser Val Lys Asp Arg Phe Ile Val Ser Arg Asp Asp Ser Lys Asn Ser
65                  70                  75                  80

Leu Tyr Leu Gln Met Asn Ser Leu Lys Thr Glu Asp Thr Ala Met Tyr
                85                  90                  95

Tyr Cys Ala Arg Trp Val Asp Asp Tyr Gln Gly Tyr Trp Ile Trp Ser
            100                 105                 110

Tyr His Asp Phe Trp Gly Gln Gly Thr Leu Val Thr Val Ser Ser
        115                 120                 125

<210> SEQ ID NO 189
<211> LENGTH: 318
<212> TYPE: DNA
<213> ORGANISM: Homo sapiens

<400> SEQUENCE: 189
tcctatgtgc tgactcagcc accctcagtg tccgtgtccc caggacagac agccagcgtc    60
acctgttctg gatatagatt gagagagaag tatgtttcct ggtatcaaca gaggccaggc   120
cactcccctg tcttggtcat ctatgaagat actaagaggc cttcaggat ccctgagcga    180 ttctctggct ccaattctgg ggacacagcc actctgacca tcagggac ccaggctata    240 gatgaggctg actattactg tcaggcgtgg gacagcagcg tgattttcgg cggagggacc   300
aagctgaccg tcctaggt                                                318

<210> SEQ ID NO 190
<211> LENGTH: 106
<212> TYPE: PRT
<213> ORGANISM: Homo sapiens

<400> SEQUENCE: 190

Ser Tyr Val Leu Thr Gln Pro Pro Ser Val Ser Val Ser Pro Gly Gln
1               5                   10                  15

Thr Ala Ser Val Thr Cys Ser Gly Tyr Arg Leu Arg Glu Lys Tyr Val
                20                  25                  30

Ser Trp Tyr Gln Gln Arg Pro Gly His Ser Pro Val Leu Val Ile Tyr
            35                  40                  45

Glu Asp Thr Lys Arg Pro Ser Gly Ile Pro Glu Arg Phe Ser Gly Ser
        50                  55                  60

Asn Ser Gly Asp Thr Ala Thr Leu Thr Ile Arg Gly Thr Gln Ala Ile
65                  70                  75                  80

Asp Glu Ala Asp Tyr Tyr Cys Gln Ala Trp Asp Ser Ser Val Ile Phe
                85                  90                  95

Gly Gly Gly Thr Lys Leu Thr Val Leu Gly
            100                 105

<210> SEQ ID NO 191
<211> LENGTH: 348
<212> TYPE: DNA
<213> ORGANISM: Homo sapiens

<400> SEQUENCE: 191
caggtgcagc tggtgcagtc tggggggaggc ttggtacagc ctggggggtc cctgagactc    60
tcctgtgcag ccactggatt caccttagc agctatgcca tgagttgggt ccgccaggct   120
ccagggaagg ggctggagtg ggtctcagtt attagtggta gtggtggtag cacatactac   180
gcagactccg tgaagggccg gttcaccatc tccagagaca attccaagaa cacgttgtat   240

```
ctgcaaatga acagcctgag agccgacgac actgccgtgt attactgtgc gcgccattac    300
tactcttctg attcttgggg tcaaggtact ctggtgaccg tctcctca                 348
```

<210> SEQ ID NO 192
<211> LENGTH: 116
<212> TYPE: PRT
<213> ORGANISM: Homo sapiens

<400> SEQUENCE: 192

Gln Val Gln Leu Val Gln Ser Gly Gly Gly Leu Val Gln Pro Gly Gly
1               5                   10                  15

Ser Leu Arg Leu Ser Cys Ala Ala Thr Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg His Tyr Tyr Ser Ser Asp Ser Trp Gly Gln Gly Thr Leu Val
            100                 105                 110

Thr Val Ser Ser
        115

<210> SEQ ID NO 193
<211> LENGTH: 333
<212> TYPE: DNA
<213> ORGANISM: Homo sapiens

<400> SEQUENCE: 193

```
caatctgccc tgactcagcc tgcctccgtg tctgggtctc ctggacagtc gatcaccatc    60
tcctgcactg gaaccagcag tgacgttggt ggttataact atgtctcttg gtaccaacag   120
cacccaggca agcccccaa attcatgatt tatgatgtca gtaagcggcc ctcaggtgtt    180
tctaatcgct tctctggctc caagtctggc aacacggcct ccctgaccat ctctgggctc   240
caggctgagg acgaggctga ttattactgc ggctcattta caagcagcat cacttatgtc   300
ttcggaactg ggaccaaggt caccgtccta ggt                                333
```

<210> SEQ ID NO 194
<211> LENGTH: 111
<212> TYPE: PRT
<213> ORGANISM: Homo sapiens

<400> SEQUENCE: 194

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Phe Thr Ser Ser
                85                  90                  95

Ile Thr Tyr Val Phe Gly Thr Gly Thr Lys Val Thr Val Leu Gly
            100                 105                 110

<210> SEQ ID NO 195
<211> LENGTH: 360
<212> TYPE: DNA
<213> ORGANISM: Homo sapiens

<400> SEQUENCE: 195
cagatgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccctg tggtggtag cacaagctac       180 gcacagaagt tccagggcag agtcaccatg accagggaca cgtccacgag cacagtctac     240
atggagctga gcagcctgag atctgaggac actgccgtgt attactgtgc gcgcggtggt     300
tacactggtt ggtctccgtc tgatccgtgg ggtcaaggta ctctggtgac cgtctcctca     360

<210> SEQ ID NO 196
<211> LENGTH: 120
<212> TYPE: PRT
<213> ORGANISM: Homo sapiens

<400> SEQUENCE: 196

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Thr Gly Trp Ser Pro Ser Asp Pro Trp Gly Gln
            100                 105                 110

Gly Thr Leu Val Thr Val Ser Ser
        115                 120

<210> SEQ ID NO 197
<211> LENGTH: 327
<212> TYPE: DNA
<213> ORGANISM: Homo sapiens

<400> SEQUENCE: 197
cagtctgtgt tgactcagcc accctcagtg tcagtggccc caggaaagac ggccaggatt      60
acctgtggtg agacaacat tggacgtaaa agtgtgcact ggtaccagca gaagccaggc      120
caggcccctg tgctggtcat ctattatgat agcgaccggc cctcagggat ccctgagcga     180
ttctctggct ccacctctgg gaacacggcc accctgacca tcagtagggt cgaagccggg     240
gatgaggccg actattactg tcaggtgtgg gatcgtagta gtgaccttta tgtcttcgga     300
actgggacca aggtcaccgt cctaggt                                         327

<210> SEQ ID NO 198
<211> LENGTH: 109
<212> TYPE: PRT
<213> ORGANISM: Homo sapiens

<400> SEQUENCE: 198

Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Arg Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Ser Ser Asp Leu
                85                  90                  95

Tyr Val Phe Gly Thr Gly Thr Lys Val Thr Val Leu Gly
            100                 105

<210> SEQ ID NO 199
<211> LENGTH: 369
<212> TYPE: DNA
<213> ORGANISM: Homo sapiens

<400> SEQUENCE: 199
caggtgcagc tggtgcagtc tggggctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggctgtgt attactgtgc gcgccatctg     300
ggtccgatgg gtatgtacga ctggtctttc gataaatggg gtcaaggtac tctggtgacc     360
gtctcctca                                                             369

<210> SEQ ID NO 200
<211> LENGTH: 123
<212> TYPE: PRT
<213> ORGANISM: Homo sapiens

<400> SEQUENCE: 200

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Leu Gly Pro Met Gly Met Tyr Asp Trp Ser Phe Asp Lys
            100                 105                 110

Trp Gly Gln Gly Thr Leu Val Thr Val Ser Ser
        115                 120

<210> SEQ ID NO 201
<211> LENGTH: 330
<212> TYPE: DNA
<213> ORGANISM: Homo sapiens

<400> SEQUENCE: 201
caatctgccc tgactcagcc tgcctccgtg tctgggtctc ctggacagtc gatcaccatc      60
tcctgcactg gaaccagcgg tgacgttggc ggttataact atgtctcctg gtaccaacac     120
cacccaggca aagcccccaa actcataatt tatgatgtca ataagcggcc ctcaggtttt     180
tctgatcggt tctctggctc caagtctggc aacacggcct ccctgacaat ctctgggctc     240
caggctgagg acgaggctga ttattactgc agctcatata caagcaccag caccgtcttc     300
ggcggaggga ccaagctgac cgtcctaggt                                       330

<210> SEQ ID NO 202
<211> LENGTH: 110
<212> TYPE: PRT
<213> ORGANISM: Homo sapiens

<400> SEQUENCE: 202

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Gly Asp Val Gly Gly Tyr
            20                  25                  30

Asn Tyr Val Ser Trp Tyr Gln His Pro Gly Lys Ala Pro Lys Leu
        35                  40                  45

Ile Ile Tyr Asp Val Asn Lys Arg Pro Ser Gly Phe Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Ser Thr Val Phe Gly Gly Gly Thr Lys Leu Thr Val Leu Gly
            100                 105                 110

<210> SEQ ID NO 203
<211> LENGTH: 363
<212> TYPE: DNA
<213> ORGANISM: Homo sapiens

<400> SEQUENCE: 203
cagatcacct tgaaggagtc tggtcctgag ctggtgaaac ccacacagac cctcacactg      60
acctgcacct tttctgggtt ctcactcagc actagtggaa tgtctgtgag ctggatccgt     120
cagcccccag ggaaggccct ggagtggctt gcacgcattg attgggatga tgataaatac     180
tacagcacat ctctgaagac caggctcacc atctccaagg acacctccaa aaaccaggtg     240
gtccttacaa tgaccaacac ggaccctgtg acacagcca cgtattactg tgcgcgcggt     300
ttctacctgg cttacggttc ttacgattct tggggtcaag gtactctggt gaccgtctcc     360
tca                                                                    363

<210> SEQ ID NO 204
<211> LENGTH: 121
<212> TYPE: PRT

<213> ORGANISM: Homo sapiens

<400> SEQUENCE: 204

| | | | | | | | | | | | | |
|---|---|---|---|---|---|---|---|---|---|---|---|---|
| Gln | Ile | Thr | Leu | Lys | Glu | Ser | Gly | Pro | Glu | Leu | Val | Lys | Pro | Thr | Gln |
| 1 | | | | 5 | | | | | 10 | | | | | 15 | |
| Thr | Leu | Thr | Leu | Thr | Cys | Thr | Phe | Ser | Gly | Phe | Ser | Leu | Ser | Thr | Ser |
| | | | 20 | | | | | 25 | | | | | 30 | | |
| Gly | Met | Ser | Val | Ser | Trp | Ile | Arg | Gln | Pro | Pro | Gly | Lys | Ala | Leu | Glu |
| | | 35 | | | | | 40 | | | | | 45 | | | |
| Trp | Leu | Ala | Arg | Ile | Asp | Trp | Asp | Asp | Lys | Tyr | Tyr | Ser | Thr | Ser |
| | 50 | | | | | 55 | | | | 60 | | | | |
| Leu | Lys | Thr | Arg | Leu | Thr | Ile | Ser | Lys | Asp | Thr | Ser | Lys | Asn | Gln | Val |
| 65 | | | | | 70 | | | | | 75 | | | | | 80 |
| Val | Leu | Thr | Met | Thr | Asn | Thr | Asp | Pro | Val | Asp | Thr | Ala | Thr | Tyr | Tyr |
| | | | | 85 | | | | | 90 | | | | | 95 | |
| Cys | Ala | Arg | Gly | Phe | Tyr | Leu | Ala | Tyr | Gly | Ser | Tyr | Asp | Ser | Trp | Gly |
| | | | 100 | | | | | 105 | | | | | 110 | | |
| Gln | Gly | Thr | Leu | Val | Thr | Val | Ser | Ser |
| | | | 115 | | | | | 120 |

<210> SEQ ID NO 205
<211> LENGTH: 321
<212> TYPE: DNA
<213> ORGANISM: Homo sapiens

<400> SEQUENCE: 205

```
tcctatgagc tgactcagcc actctcagtg tcagtggccc tgggacagac ggccaggatt      60
acctgtgggg gaaacaacat tggaagtaaa aatgtgcact ggtaccagca gaagccaggc     120
caggcccctg tgctggtcat ctatagggat agcaaccggc cctctgggat ccctgagcga     180
ttctctggct ccaactcggg gaacacggcc accctgacca tcagcagagc ccaagccggg     240
gatgaggctg actattactg tcaggtgtgg gacagcagta ttgtggtatt cggcggaggg     300
accaagctga ccgtcctagg t                                               321
```

<210> SEQ ID NO 206
<211> LENGTH: 107
<212> TYPE: PRT
<213> ORGANISM: Homo sapiens

<400> SEQUENCE: 206

| | | | | | | | | | | | | | | | |
|---|---|---|---|---|---|---|---|---|---|---|---|---|---|---|---|
| Ser | Tyr | Glu | Leu | Thr | Gln | Pro | Leu | Ser | Val | Ser | Val | Ala | Leu | Gly | Gln |
| 1 | | | | 5 | | | | | 10 | | | | | 15 | |
| Thr | Ala | Arg | Ile | Thr | Cys | Gly | Gly | Asn | Asn | Ile | Gly | Ser | Lys | Asn | Val |
| | | | 20 | | | | | 25 | | | | | 30 | | |
| His | Trp | Tyr | Gln | Gln | Lys | Pro | Gly | Gln | Ala | Pro | Val | Leu | Val | Ile | Tyr |
| | | | 35 | | | | | 40 | | | | | 45 | | |
| Arg | Asp | Ser | Asn | Arg | Pro | Ser | Gly | Ile | Pro | Glu | Arg | Phe | Ser | Gly | Ser |
| | | | 50 | | | | | 55 | | | | | 60 | | |
| Asn | Ser | Gly | Asn | Thr | Ala | Thr | Leu | Thr | Ile | Ser | Arg | Ala | Gln | Ala | Gly |
| 65 | | | | | 70 | | | | | 75 | | | | | 80 |
| Asp | Glu | Ala | Asp | Tyr | Tyr | Cys | Gln | Val | Trp | Asp | Ser | Ser | Ile | Val | Val |
| | | | | 85 | | | | | 90 | | | | | 95 | |
| Phe | Gly | Gly | Gly | Thr | Lys | Leu | Thr | Val | Leu | Gly |
| | | | 100 | | | | | 105 | | |

<210> SEQ ID NO 207

```
<211> LENGTH: 360
<212> TYPE: DNA
<213> ORGANISM: Homo sapiens

<400> SEQUENCE: 207
gaagtgcagc tggtgcagtc tggggctgag gtgaagaagc ctggggcctc agtgaaggtt    60
tcctgcaagg catctggata caccttcacc aattactata tacactgggt gcgacaggcc   120
cctggacaag gccttgagtg gatgggaata atcaaccctg caagtggtag gacaaggtac   180
gcacagaggt tccagggcag agtcaccatg accagggaca cgtccacgaa cacagtctac   240
atggacctga gcagcctgag atctgaagac accgccatgt attactgtgc gcgctctggt   300
tactactggg gtgttaacgg tgatcagtgg ggtcaaggta ctctggtgac cgtctcctca   360

<210> SEQ ID NO 208
<211> LENGTH: 120
<212> TYPE: PRT
<213> ORGANISM: Homo sapiens

<400> SEQUENCE: 208

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Met
            35                  40                  45

Gly Ile Ile Asn Pro Thr Ser Gly Arg Thr Arg Tyr Ala Gln Arg Phe
        50                  55                  60

Gln Gly Arg Val Thr Met Thr Arg Asp Thr Ser Thr Asn Thr Val Tyr
65                  70                  75                  80

Met Asp Leu Ser Ser Leu Arg Ser Glu Asp Thr Ala Met Tyr Tyr Cys
                85                  90                  95

Ala Arg Ser Gly Tyr Tyr Trp Gly Val Asn Gly Asp Gln Trp Gly Gln
            100                 105                 110

Gly Thr Leu Val Thr Val Ser Ser
        115                 120

<210> SEQ ID NO 209
<211> LENGTH: 105
<212> TYPE: PRT
<213> ORGANISM: Homo sapiens

<400> SEQUENCE: 209

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Gly Ser Pro Val
            35                  40                  45

Lys Ala Gly Val Glu Thr Thr Lys Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 210
<211> LENGTH: 318
<212> TYPE: DNA
<213> ORGANISM: Homo sapiens

<400> SEQUENCE: 210
cagcctaagg ccaaccctac cgtgaccctg ttccccccat cctccgagga actgcaggcc      60
aacaaggcca ccctcgtgtg cctgatctcc gacttctacc ctggcgccgt gaccgtggcc     120
tggaaggctg atggatctcc tgtgaaggcc ggcgtggaaa ccaccaagcc ctccaagcag     180
tccaacaaca aatacgccgc ctcctcctac ctgtccctga cccctgagca gtggaagtcc     240
caccggtcct acagctgcca agtgacccac gagggctcca ccgtggaaaa gaccgtggct     300
cctaccgagt gctcctag                                                   318

<210> SEQ ID NO 211
<211> LENGTH: 106
<212> TYPE: PRT
<213> ORGANISM: Homo sapiens

<400> SEQUENCE: 211

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 212
<211> LENGTH: 321
<212> TYPE: DNA
<213> ORGANISM: Homo sapiens

<400> SEQUENCE: 212
accgtggccg ctccctccgt gttcatcttc ccaccttccg acgagcagct gaagtccggc      60
accgcttctg tcgtgtgcct gctgaacaac ttctaccccc gcgaggccaa ggtgcagtgg     120
aaggtggaca acgccctgca gagcggcaac tcccaggaat ccgtgaccga gcaggactcc     180
aaggacagca cctactccct gtcctccacc ctgaccctgt ccaaggccga ctacgagaag     240
cacaaggtgt acgcctgcga agtgacccac cagggcctgt ctagccccgt gaccaagtct     300
ttcaaccggg gcgagtgcta g                                               321

<210> SEQ ID NO 213
<211> LENGTH: 330
<212> TYPE: PRT
<213> ORGANISM: Homo sapiens

<400> SEQUENCE: 213

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 214
<211> LENGTH: 1002
<212> TYPE: DNA
<213> ORGANISM: Homo sapiens

<400> SEQUENCE: 214

| | | | | | |
|---|---|---|---|---|---|
| gtctcctcag | cttccaccaa | gggcccatcg | gtcttccccc | tggcaccctc | ctccaagagc | 60 |
| acctctgggg | gcacagcggc | cctgggctgc | ctggtcaagg | actacttccc | cgaaccggtg | 120 |
| acggtgtcgt | ggaactcagg | cgccctgacc | agcggcgtgc | acaccttccc | ggccgtccta | 180 |
| cagtcctcag | gactctactc | cctcagcagc | gtggtgaccg | tgccctccag | cagcttgggc | 240 |
| acccagacct | acatctgcaa | cgtgaatcac | aagcccagca | acaccaaggt | ggacaagaag | 300 |

```
gttgagccca atcttgtga caaaactcac acatgcccac cgtgcccagc acctgaactc    360 ctgggggac cgtcagtctt cctcttcccc ccaaaaccca aggacaccct catgatctcc    420
cggacccctg aggtcacatg cgtggtggtg gacgtgagcc acgaagaccc tgaggtcaag    480
ttcaactggt acgtggacgg cgtggaggtg cataatgcca agacaaagcc gcggaggag     540 cagtacaaca gcacgtaccg tgtggtcagc gtcctcaccg tcctgcacca ggactggctg    600
aatggcaagg agtacaagtg caaggtctcc aacaaagccc tcccagcccc catcgagaaa   660
accatctcca aagccaaagg gcagcccga  gaaccacagg tgtacaccct gcccccatcc    720
cgggaggaga tgaccaagaa ccaggtcagc ctgacctgcc tggtcaaagg cttctatccc   780
agcgacatcg ccgtggagtg ggagagcaat gggcagccgg agaacaacta caagaccacg   840
cctcccgtgc tggactccga cggctccttc ttcctctaca gcaagctcac cgtggacaag   900 agcaggtgg agcaggggaa cgtcttctca tgctccgtga tgcatgaggc tctgcacaac    960
cactacacgc agaagagcct ctccctgtct ccgggtaaat ga                       1002
```

<210> SEQ ID NO 215
<211> LENGTH: 502
<212> TYPE: PRT
<213> ORGANISM: Homo sapiens

<400> SEQUENCE: 215

```
Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Ile Val Val
                85                  90                  95

Phe Gly Gly Gly Thr Lys Leu Thr Val Leu Gly Ser Arg Gly Gly Gly
            100                 105                 110

Gly Ser Gly Gly Gly Gly Ser Gly Gly Gly Gly Ser Leu Glu Met Ala
        115                 120                 125

Glu Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asn Tyr
145                 150                 155                 160

Tyr Ile His Trp Val Arg Gln Ala Pro Gly Gln Gly Leu Glu Trp Met
                165                 170                 175

Gly Ile Ile Asn Pro Thr Ser Gly Arg Thr Arg Tyr Ala Gln Arg Phe
            180                 185                 190

Gln Gly Arg Val Thr Met Thr Arg Asp Thr Ser Thr Asn Thr Val Tyr
        195                 200                 205

Met Asp Leu Ser Ser Leu Arg Ser Glu Asp Thr Ala Met Tyr Tyr Cys
    210                 215                 220

Ala Arg Ser Gly Tyr Tyr Trp Gly Val Asn Gly Asp Gln Trp Gly Gln
225                 230                 235                 240

Gly Thr Leu Val Thr Val Ser Ser Gly Gly Gly Gly Ser Asp Val Gln
                245                 250                 255
```

Leu Val Gln Ser Gly Ala Glu Val Lys Lys Pro Gly Ala Ser Val Lys
            260                 265                 270

Val Ser Cys Lys Ala Ser Gly Tyr Thr Phe Thr Arg Tyr Thr Met His
        275                 280                 285

Trp Val Arg Gln Ala Pro Gly Gln Gly Leu Glu Trp Ile Gly Tyr Ile
    290                 295                 300

Asn Pro Ser Arg Gly Tyr Thr Asn Tyr Ala Asp Ser Val Lys Gly Arg
305                 310                 315                 320

Phe Thr Ile Thr Thr Asp Lys Ser Thr Ser Thr Ala Tyr Met Glu Leu
                325                 330                 335

Ser Ser Leu Arg Ser Glu Asp Thr Ala Thr Tyr Tyr Cys Ala Arg Tyr
            340                 345                 350

Tyr Asp Asp His Tyr Cys Leu Asp Tyr Trp Gly Gln Gly Thr Thr Val
        355                 360                 365

Thr Val Ser Ser Gly Glu Gly Thr Ser Thr Gly Ser Gly Gly Ser Gly
    370                 375                 380

Gly Ser Gly Gly Ala Asp Asp Ile Val Leu Thr Gln Ser Pro Ala Thr
385                 390                 395                 400

Leu Ser Leu Ser Pro Gly Glu Arg Ala Thr Leu Ser Cys Arg Ala Ser
                405                 410                 415

Gln Ser Val Ser Tyr Met Asn Trp Tyr Gln Gln Lys Pro Gly Lys Ala
            420                 425                 430

Pro Lys Arg Trp Ile Tyr Asp Thr Ser Lys Val Ala Ser Gly Val Pro
        435                 440                 445

Ala Arg Phe Ser Gly Ser Gly Ser Gly Thr Asp Tyr Ser Leu Thr Ile
    450                 455                 460

Asn Ser Leu Glu Ala Glu Asp Ala Ala Thr Tyr Tyr Cys Gln Gln Trp
465                 470                 475                 480

Ser Ser Asn Pro Leu Thr Phe Gly Gly Gly Thr Lys Val Glu Ile Lys
                485                 490                 495

His His His His His His
            500

<210> SEQ ID NO 216
<211> LENGTH: 21
<212> TYPE: PRT
<213> ORGANISM: Homo sapiens

<400> SEQUENCE: 216

Ser Arg Gly Gly Gly Ser Gly Gly Gly Ser Gly Gly Gly
1               5                   10                  15

Ser Leu Glu Met Ala
            20

<210> SEQ ID NO 217
<211> LENGTH: 50
<212> TYPE: DNA
<213> ORGANISM: Homo sapiens

<400> SEQUENCE: 217
ctagaggtgg tggtggtagc ggcggcggcg gctctggtgg tggtggatcc        50

<210> SEQ ID NO 218
<211> LENGTH: 5
<212> TYPE: PRT
<213> ORGANISM: Homo sapiens

<400> SEQUENCE: 218

Gly Gly Gly Gly Ser
1               5

<210> SEQ ID NO 219
<211> LENGTH: 15
<212> TYPE: DNA
<213> ORGANISM: Homo sapiens

<400> SEQUENCE: 219
ggcgggggag gatcc                                                15

<210> SEQ ID NO 220
<211> LENGTH: 249
<212> TYPE: PRT
<213> ORGANISM: Homo sapiens

<400> SEQUENCE: 220

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys His His His His His His
                245

<210> SEQ ID NO 221
<211> LENGTH: 750
<212> TYPE: DNA
<213> ORGANISM: Homo sapiens

<400> SEQUENCE: 221

```
gacgtgcagc tggtgcagag cggagctgaa gtgaagaaac ctggcgcctc cgtgaaggtg     60
tcctgcaaag ctagcggcta taccttcacc cggtacacca tgcactgggt gcgccaggca    120
cctggacagg gactggaatg gatcggctac atcaacccct cccggggcta caccaactac    180
gccgactctg tgaagggccg gttcaccatc accaccgata gtccaccag caccgcttac    240
atggaactgt cctccctgag atccgaggac accgctacct actattgcgc ccggtactac    300
gacgaccact actgcctgga ctactgggga cagggaacca cagtgaccgt gtcctctggc    360
gagggcacct ctactggatc tgggggaagt ggtggttctg gcggcgctga cgacatcgtg    420
ctgacccagt ctccagccac cctgtctctg agcccaggcg agagagctac cctgtcctgc    480
agagcctccc agtccgtgtc ctacatgaat tggtatcagc agaagcctgg caaggcccct    540
aagcggtgga tctacgacac ctccaaggtg gcctctggcg tgccagcccg gttttccgga    600
tctggctctg gcaccgacta ctccctgacc atcaacagcc tggaagccga ggacgctgcc    660
acctattact gccagcagtg gtcctccaac cccctgacct ttggaggcgg caccaaggtg    720
gaaatcaagc accaccatca tcaccactga                                      750

<210> SEQ ID NO 222
<211> LENGTH: 2814
<212> TYPE: DNA
<213> ORGANISM: Homo sapiens

<400> SEQUENCE: 222
atgcaccggc cgcgccgccg cgggacgcgc ccgccgctcc tggcgctgct ggccgcgctg     60
ctgctggccg cacgcgggc tgctgcccaa gaaacagagc tgtcagtcag tgctgaatta    120
gtgcctacct catcatggaa catctcaagt gaactcaaca agattcttta cctgaccctc    180
gatgaaccaa tgaataacat caccacgtct ctgggccaga cagcagaact gcactgcaaa    240
gtctctggga atccacctcc caccatccgc tggttcaaaa atgatgctcc tgtggtccag    300
gagcccggga ggctctcctt tcggtccacc atctatggct ctcggctgcg gattagaaac    360
ctcgacacca cagacacagg ctacttccag tgcgtggcaa caaacggcaa ggaggtggtt    420
tcttccactg gagtcttgtt tgtcaagttt ggccccctc ccactgcaag tccaggatac    480
tcagatgagt atgaagaaga tggattctgt cagccataca gagggattgc atgtgcaaga    540
tttattggca accgcaccgt ctatatggag tctttgcaca tgcaagggga aatagaaaat    600
cagatcacag ctgccttcac tatgattggc acttccagtc acttatctga taagtgttct    660
cagttcgcca ttccttccct gtgccactat gccttccgt actgcgatga acttcatcc    720
gtcccaaagc cccgtgactt gtgtcgcgat gaatgtgaaa tcctggagaa tgtcctgtgt    780
caaacagagt acattttgc aagatcaaat cccatgattc tgatgaggct gaaactgcca    840
aactgtgaag atctccccca gccagagagc ccagaagctg cgaactgtat ccggattgga    900
attcccatgg cagatcctat aaataaaaat cacaagtgtt ataacagcac aggtgtggac    960
taccggggga ccgtcagtgt gaccaaatca gggcgccagt gccagccatg gaattcccag   1020
tatccccaca cacactttt caccgccctt cgtttcccag agctgaatgg aggccattcc   1080
tactgccgca acccagggaa tcaaaaggaa gctccctggt gcttcacctt ggatgaaaac   1140
tttaagtctg atctgtgtga catcccagcg tgcgattcaa aggattccaa ggagaagaat   1200
aaaatgaaaa tcctgtacat actagtgcca agtgtggcca ttcccctggc cattgcttta   1260
ctcttcttct tcatttgcgt ctgtcggaat aaccagaagt catcgtcggc accagtccag   1320
aggcaaccaa aacacgtcag aggtcaaaat gtagagatgt caatgctgaa tgcatataaa   1380
```

-continued

```
cccaagagca aggctaaaga gctacctctt tctgctgtac gctttatgga agaattgggt    1440
gagtgtgcct ttggaaaaat ctataaaggc catctctatc tcccaggcat ggaccatgct    1500
cagctggttg ctatcaagac cttgaaagac tataacaacc cccagcaatg gacggaattt    1560
caacaagaag cctccctaat ggcagaactg caccaccca atattgtctg ccttctaggt    1620
gccgtcactc aggaacaacc tgtgtgcatg cttttgagt atattaatca ggggatctc    1680
catgagttcc tcatcatgag atccccacac tctgatgttg ctgcagcag tgatgaagat    1740
gggactgtga atccagcct ggaccacgga gattttctgc acattgcaat tcagattgca    1800
gctggcatga ataccctgtc tagtcacttc tttgtccaca aggaccttgc agctcgcaat    1860
attttaatcg gagagcaact tcatgtaaag atttcagact gggctttc cagagaaatt    1920
tactccgctg attactacag ggtccagagt aagtccttgc tgcccattcg ctggatgccc    1980
cctgaagcca tcatgtatgg caaattctct tctgattcag atatctggtc ctttggggtt    2040
gtcttgtggg agattttcag ttttggactc cagccatatt atggattcag taaccaggaa    2100
gtgattgaga tggtgagaaa acggcagctc ttaccatgct ctgaagactg cccacccaga    2160
atgtacagcc tcatgacaga gtgctggaat gagattcctt ctaggagacc aagatttaaa    2220
gatattcacg tccggcttcg gtcctgggag ggactctcaa gtcacacaag ctctactact    2280
ccttcagggg gaaatgccac cacacagaca acctccctca gtgccagccc agtgagtaat    2340
ctcagtaacc ccagatatcc taattacatg ttcccgagcc agggtattac accacagggc    2400
cagattgctg gtttcattgg cccgccaata cctcagaacc agcgattcat tcccatcaat    2460
ggatacccaa tacctcctgg atatgcagcg tttccagctg cccactacca gccaacaggt    2520
cctcccagag tgattcagca ctgcccacct cccaagagtc ggtccccaag cagtgccagt    2580
gggtcgacta gcactggcca tgtgactagc ttgccctcat caggatccaa tcaggaagca    2640
aatattcctt tactaccaca catgtcaatt ccaaatcatc ctggtggaat gggtatcacc    2700
gtttttggca acaaatctca aaaaccctac aaaattgact caaagcaagc atctttacta    2760
ggagacgcca atattcatgg acacaccgaa tctatgattt ctgcagaact gtaa          2814
```

<210> SEQ ID NO 223
<211> LENGTH: 937
<212> TYPE: PRT
<213> ORGANISM: Homo sapiens

<400> SEQUENCE: 223

Met His Arg Pro Arg Arg Gly Thr Arg Pro Leu Leu Ala Leu
1               5                   10                  15

Leu Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr

```
            115                 120                 125
Phe Gln Cys Val Ala Thr Asn Gly Lys Glu Val Val Ser Ser Thr Gly
    130                 135                 140
Val Leu Phe Val Lys Phe Gly Pro Pro Thr Ala Ser Pro Gly Tyr
145                 150                 155                 160
Ser Asp Glu Tyr Glu Asp Gly Phe Cys Gln Pro Tyr Arg Gly Ile
                165                 170                 175
Ala Cys Ala Arg Phe Ile Gly Asn Arg Thr Val Tyr Met Glu Ser Leu
            180                 185                 190
His Met Gln Gly Glu Ile Glu Asn Gln Ile Thr Ala Ala Phe Thr Met
            195                 200                 205
Ile Gly Thr Ser Ser His Leu Ser Asp Lys Cys Ser Gln Phe Ala Ile
            210                 215                 220
Pro Ser Leu Cys His Tyr Ala Phe Pro Tyr Cys Asp Glu Thr Ser Ser
225                 230                 235                 240
Val Pro Lys Pro Arg Asp Leu Cys Arg Asp Glu Cys Glu Ile Leu Glu
                245                 250                 255
Asn Val Leu Cys Gln Thr Glu Tyr Ile Phe Ala Arg Ser Asn Pro Met
            260                 265                 270
Ile Leu Met Arg Leu Lys Leu Pro Asn Cys Glu Asp Leu Pro Gln Pro
            275                 280                 285
Glu Ser Pro Glu Ala Ala Asn Cys Ile Arg Ile Gly Ile Pro Met Ala
            290                 295                 300
Asp Pro Ile Asn Lys Asn His Lys Cys Tyr Asn Ser Thr Gly Val Asp
305                 310                 315                 320
Tyr Arg Gly Thr Val Ser Val Thr Lys Ser Gly Arg Gln Cys Gln Pro
                325                 330                 335
Trp Asn Ser Gln Tyr Pro His Thr His Thr Phe Thr Ala Leu Arg Phe
            340                 345                 350
Pro Glu Leu Asn Gly Gly His Ser Tyr Cys Arg Asn Pro Gly Asn Gln
            355                 360                 365
Lys Glu Ala Pro Trp Cys Phe Thr Leu Asp Glu Asn Phe Lys Ser Asp
            370                 375                 380
Leu Cys Asp Ile Pro Ala Cys Asp Ser Lys Asp Ser Lys Glu Lys Asn
385                 390                 395                 400
Lys Met Glu Ile Leu Tyr Ile Leu Val Pro Ser Val Ala Ile Pro Leu
                405                 410                 415
Ala Ile Ala Leu Leu Phe Phe Phe Ile Cys Val Cys Arg Asn Asn Gln
            420                 425                 430
Lys Ser Ser Ser Ala Pro Val Gln Arg Gln Pro Lys His Val Arg Gly
            435                 440                 445
Gln Asn Val Glu Met Ser Met Leu Asn Ala Tyr Lys Pro Lys Ser Lys
            450                 455                 460
Ala Lys Glu Leu Pro Leu Ser Ala Val Arg Phe Met Glu Glu Leu Gly
465                 470                 475                 480
Glu Cys Ala Phe Gly Lys Ile Tyr Lys Gly His Leu Tyr Leu Pro Gly
                485                 490                 495
Met Asp His Ala Gln Leu Val Ala Ile Lys Thr Leu Lys Asp Tyr Asn
            500                 505                 510
Asn Pro Gln Gln Trp Thr Glu Phe Gln Gln Glu Ala Ser Leu Met Ala
            515                 520                 525
Glu Leu His His Pro Asn Ile Val Cys Leu Leu Gly Ala Val Thr Gln
            530                 535                 540
```

```
Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
                595                 600                 605

His Phe Phe Val His Lys Asp Leu Ala Ala Arg Asn Ile Leu Ile Gly
            610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
                660                 665                 670

Ser Asp Ile Trp Ser Phe Gly Val Val Leu Trp Glu Ile Phe Ser Phe
            675                 680                 685

Gly Leu Gln Pro Tyr Tyr Gly Phe Ser Asn Gln Glu Val Ile Glu Met
690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
                740                 745                 750

Ser Ser His Thr Ser Ser Thr Thr Pro Ser Gly Gly Asn Ala Thr Thr
            755                 760                 765

Gln Thr Thr Ser Leu Ser Ala Ser Pro Val Ser Asn Leu Ser Asn Pro
770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
                820                 825                 830

Ala Ala His Tyr Gln Pro Thr Gly Pro Pro Arg Val Ile Gln His Cys
            835                 840                 845

Pro Pro Pro Lys Ser Arg Ser Pro Ser Ser Ala Ser Gly Ser Thr Ser
850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
                900                 905                 910

Asp Ser Lys Gln Ala Ser Leu Leu Gly Asp Ala Asn Ile His Gly His
            915                 920                 925

Thr Glu Ser Met Ile Ser Ala Glu Leu
930                 935
```

<210> SEQ ID NO 224
<211> LENGTH: 2832

<212> TYPE: DNA
<213> ORGANISM: Homo sapiens

<400> SEQUENCE: 224

| | | | | | |
|---|---|---|---|---|---|
| atggcccggg | gctcggcgct | cccgcggcgg | ccgctgctgt | gcatcccggc | cgtctgggcg | 60 |
| gccgccgcgc | ttctgctctc | agtgtcccgg | acttcaggtg | aagtggaggt | tctggatccg | 120 |
| aacgacccct | taggacccct | tgatgggcag | gacggcccga | ttccaactct | gaaaggttac | 180 |
| tttctgaatt | ttctggagcc | agtaaacaat | atcaccattg | tccaaggcca | gacggcaatt | 240 |
| ctgcactgca | aggtggcagg | aaacccaccc | cctaacgtgc | ggtggctaaa | gaatgatgcc | 300 |
| ccggtggtgc | aggagccgcg | gcggatcatc | atccggaaga | cagaatatgg | ttcacgactg | 360 |
| cgaatccagg | acctggacac | gacagacact | ggctactacc | agtgcgtggc | caccaacggg | 420 |
| atgaagacca | ttaccgccac | tggcgtcctg | tttgtgcggc | tgggtccaac | gcacagccca | 480 |
| aatcataact | ttcaggatga | ttaccacgag | gatgggttct | gccagcctta | ccggggaatt | 540 |
| gcctgtgcac | gcttcattgg | caaccggacc | atttatgtgg | actcgcttca | gatgcagggg | 600 |
| gagattgaaa | accgaatcac | agcggccttc | accatgatcg | gcacgtctac | gcacctgtcg | 660 |
| gaccagtgct | cacagttcgc | catcccatcc | ttctgccact | cgtgtttcc | tctgtgcgac | 720 |
| gcgcgctccc | ggacacccaa | gccgcgtgag | ctgtgccgcg | acgagtgcga | ggtgctggag | 780 |
| agcgacctgt | gccgccagga | gtacaccatc | gcccgctcca | acccgctcat | cctcatgcgg | 840 |
| cttcagctgc | ccaagtgtga | ggcgctgccc | atgcctgaga | gccccgacgc | tgccaactgc | 900 |
| atgcgcattg | catcccagc | cgagaggctg | ggccgctacc | atcagtgcta | taacggctca | 960 |
| ggcatggatt | acagaggaac | ggcaagcacc | accaagtcag | gccaccagtg | ccagccgtgg | 1020 |
| gccctgcagc | accccacag | ccaccacctg | tccagcacag | acttccctga | gcttggaggg | 1080 |
| gggcacgcct | actgccggaa | ccccggaggc | cagatggagg | gccctggtg | ctttacgcag | 1140 |
| aataaaaacg | tacgcatgga | actgtgtgac | gtaccctcgt | gtagtccccg | agacagcagc | 1200 |
| aagatgggga | ttctgtacat | cttggtcccc | agcatcgcaa | ttccactggt | catcgcttgc | 1260 |
| cttttcttct | tggttgcat | gtgccggaat | aagcagaagg | catctgcgtc | cacaccgcag | 1320 |
| cggcgacagc | tgatggcctc | gcccagccaa | gacatggaaa | tgcccctcat | taaccagcac | 1380 |
| aaacaggcca | aactcaaaga | gatcagcctg | tctgcggtga | ggttcatgga | ggagctggga | 1440 |
| gaggaccggt | ttgggaaagt | ctacaaaggt | cacctgttcg | gccctgcccc | ggggagcag | 1500 |
| acccaggctg | tggccatcaa | aacgctgaag | gacaaagcgg | aggggcccct | gcgggaggag | 1560 |
| ttccggcatg | aggctatgct | gcgagcacgg | ctgcaacacc | ccaacgtcgt | ctgcctgctg | 1620 |
| ggcgtggtga | ccaaggacca | gccctgagc | atgatcttca | gctactgttc | gcacggcgac | 1680 |
| ctccacgaat | tcctggtcat | gcgctcgccg | cactcggacg | tgggcagcac | cgatgatgac | 1740 |
| cgcacggtga | agtccgccct | ggagcccccc | gacttcgtgc | accttgtggc | acagatcgcg | 1800 |
| gcggggatgg | agtacctatc | cagccaccac | gtggttcaca | aggacctggc | cacccgcaat | 1860 |
| gtgctagtgt | acgacaagct | gaacgtgaag | atctcagact | tgggcctctt | ccgagaggtg | 1920 |
| tatgccgccg | attactacaa | gctgctgggg | aactcgctgc | tgcctatccg | ctggatggcc | 1980 |
| ccagaggcca | tcatgtacgg | caagttctcc | atcgactcag | acatctggtc | ctacggtgtg | 2040 |
| gtcctgtggg | aggtcttcag | ctacggcctg | cagccctact | gcgggtactc | caaccaggat | 2100 |
| gtggtggaga | tgatccggaa | ccggcaggtg | ctgccttgcc | ccgatgactg | tcccgcctgg | 2160 |
| gtgtatgccc | tcatgatcga | gtgctggaac | gagttcccca | gccggcggcc | ccgcttcaag | 2220 |

-continued

```
gacatccaca gccggctccg agcctggggc aacctttcca actacaacag ctcggcgcag    2280
acctcggggg ccagcaacac cacgcagacc agctccctga gcaccagccc agtgagcaat    2340
gtgagcaacg cccgctacgt ggggcccaag cagaaggccc cgcccttccc acagcccag     2400 ttcatcccca tgaagggcca gatcagaccc atggtgcccc gccgcagct ctacgtcccc     2460 gtcaacggct accagccggt gccggcctat ggggcctacc tgcccaactt ctaccggtg     2520 cagatcccaa tgcagatggc cccgcagcag gtgcctcctc agatggtccc caagcccagc    2580
tcacaccaca gtggcagtgg ctccaccagc acaggctacg tcaccacggc ccctccaac     2640 acatccatgg cagacagggc agccctgctc tcagagggcg ctgatgacac acagaacgcc    2700
ccagaagatg gggcccagag caccgtgcag gaagcagagg aggaggagga aggctctgtc    2760
ccagagactg agctgctggg ggactgtgac actctgcagg tggacgaggc ccaagtccag    2820
ctggaagctt ga                                                        2832
```

<210> SEQ ID NO 225
<211> LENGTH: 943
<212> TYPE: PRT
<213> ORGANISM: Homo sapiens

<400> SEQUENCE: 225

```
Met Ala Arg Gly Ser Ala Leu Pro Arg Pro Leu Leu Cys Ile Pro
1               5                   10                  15

Ala Val Trp Ala Ala Ala Leu Leu Leu Ser Val Ser Arg Thr Ser
                20                  25                  30

Gly Glu Val Glu Val Leu Asp Pro Asn Asp Pro Leu Gly Pro Leu Asp
                35                  40                  45

Gly Gln Asp Gly Pro Ile Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Asn Val Arg Trp Leu
                85                  90                  95

Lys Asn Asp Ala Pro Val Val Gln Glu Pro Arg Arg Ile Ile Ile Arg
                100                 105                 110

Lys Thr Glu Tyr Gly Ser Arg Leu Arg Ile Gln Asp Leu Asp Thr Thr
                115                 120                 125

Asp Thr Gly Tyr Tyr Gln Cys Val Ala Thr Asn Gly Met Lys Thr Ile
    130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
                180                 185                 190

Val Asp Ser Leu Gln Met Gln Gly Glu Ile Glu Asn Arg Ile Thr Ala
                195                 200                 205

Ala Phe Thr Met Ile Gly Thr Ser Thr His Leu Ser Asp Gln Cys Ser
    210                 215                 220

Gln Phe Ala Ile Pro Ser Phe Cys His Phe Val Phe Pro Leu Cys Asp
225                 230                 235                 240

Ala Arg Ser Arg Thr Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
```

-continued

```
                260                 265                 270
Ser Asn Pro Leu Ile Leu Met Arg Leu Gln Leu Pro Lys Cys Glu Ala
            275                 280                 285

Leu Pro Met Pro Glu Ser Pro Asp Ala Ala Asn Cys Met Arg Ile Gly
        290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
            340                 345                 350

Thr Asp Phe Pro Glu Leu Gly Gly His Ala Tyr Cys Arg Asn Pro
        355                 360                 365

Gly Gly Gln Met Glu Gly Pro Trp Cys Phe Thr Gln Asn Lys Asn Val
    370                 375                 380

Arg Met Glu Leu Cys Asp Val Pro Ser Cys Ser Pro Arg Asp Ser Ser
385                 390                 395                 400

Lys Met Gly Ile Leu Tyr Ile Leu Val Pro Ser Ile Ala Ile Pro Leu
                405                 410                 415

Val Ile Ala Cys Leu Phe Phe Leu Val Cys Met Cys Arg Asn Lys Gln
            420                 425                 430

Lys Ala Ser Ala Ser Thr Pro Gln Arg Arg Gln Leu Met Ala Ser Pro
        435                 440                 445

Ser Gln Asp Met Glu Met Pro Leu Ile Asn Gln His Lys Gln Ala Lys
    450                 455                 460

Leu Lys Glu Ile Ser Leu Ser Ala Val Arg Phe Met Glu Glu Leu Gly
465                 470                 475                 480

Glu Asp Arg Phe Gly Lys Val Tyr Lys Gly His Leu Phe Gly Pro Ala
                485                 490                 495

Pro Gly Glu Gln Thr Gln Ala Val Ala Ile Lys Thr Leu Lys Asp Lys
            500                 505                 510

Ala Glu Gly Pro Leu Arg Glu Glu Phe Arg His Glu Ala Met Leu Arg
        515                 520                 525

Ala Arg Leu Gln His Pro Asn Val Val Cys Leu Leu Gly Val Val Thr
    530                 535                 540

Lys Asp Gln Pro Leu Ser Met Ile Phe Ser Tyr Cys Ser His Gly Asp
545                 550                 555                 560

Leu His Glu Phe Leu Val Met Arg Ser Pro His Ser Asp Val Gly Ser
                565                 570                 575

Thr Asp Asp Asp Arg Thr Val Lys Ser Ala Leu Glu Pro Pro Asp Phe
            580                 585                 590

Val His Leu Val Ala Gln Ile Ala Ala Gly Met Glu Tyr Leu Ser Ser
        595                 600                 605

His His Val Val His Lys Asp Leu Ala Thr Arg Asn Val Leu Val Tyr
    610                 615                 620

Asp Lys Leu Asn Val Lys Ile Ser Asp Leu Gly Leu Phe Arg Glu Val
625                 630                 635                 640

Tyr Ala Ala Asp Tyr Tyr Lys Leu Leu Gly Asn Ser Leu Leu Pro Ile
                645                 650                 655

Arg Trp Met Ala Pro Glu Ala Ile Met Tyr Gly Lys Phe Ser Ile Asp
            660                 665                 670

Ser Asp Ile Trp Ser Tyr Gly Val Val Leu Trp Glu Val Phe Ser Tyr
        675                 680                 685
```

```
Gly Leu Gln Pro Tyr Cys Gly Tyr Ser Asn Gln Asp Val Val Glu Met
            690                 695                 700

Ile Arg Asn Arg Gln Val Leu Pro Cys Pro Asp Cys Pro Ala Trp
705                 710                 715                 720

Val Tyr Ala Leu Met Ile Glu Cys Trp Asn Glu Phe Pro Ser Arg Arg
                725                 730                 735

Pro Arg Phe Lys Asp Ile His Ser Arg Leu Arg Ala Trp Gly Asn Leu
            740                 745                 750

Ser Asn Tyr Asn Ser Ser Ala Gln Thr Ser Gly Ala Ser Asn Thr Thr
                755                 760                 765

Gln Thr Ser Ser Leu Ser Thr Ser Pro Val Ser Asn Val Ser Asn Ala
770                 775                 780

Arg Tyr Val Gly Pro Lys Gln Lys Ala Pro Pro Phe Pro Gln Pro Gln
785                 790                 795                 800

Phe Ile Pro Met Lys Gly Gln Ile Arg Pro Met Val Pro Pro Pro Gln
                805                 810                 815

Leu Tyr Val Pro Val Asn Gly Tyr Gln Pro Val Pro Ala Tyr Gly Ala
            820                 825                 830

Tyr Leu Pro Asn Phe Tyr Pro Val Gln Ile Pro Met Gln Met Ala Pro
                835                 840                 845

Gln Gln Val Pro Pro Gln Met Val Pro Lys Pro Ser Ser His His Ser
850                 855                 860

Gly Ser Gly Ser Thr Ser Thr Gly Tyr Val Thr Thr Ala Pro Ser Asn
865                 870                 875                 880

Thr Ser Met Ala Asp Arg Ala Ala Leu Leu Ser Glu Gly Ala Asp Asp
                885                 890                 895

Thr Gln Asn Ala Pro Glu Asp Gly Ala Gln Ser Thr Val Gln Glu Ala
            900                 905                 910

Glu Glu Glu Glu Glu Gly Ser Val Pro Glu Thr Glu Leu Leu Gly Asp
                915                 920                 925

Cys Asp Thr Leu Gln Val Asp Glu Ala Gln Val Gln Leu Glu Ala
            930                 935                 940

<210> SEQ ID NO 226
<211> LENGTH: 15
<212> TYPE: PRT
<213> ORGANISM: Homo sapiens

<400> SEQUENCE: 226

Thr Gly Tyr Tyr Gln Cys Val Ala Thr Asn Gly Met Lys Thr Ile
1               5                   10                  15

<210> SEQ ID NO 227
<211> LENGTH: 15
<212> TYPE: PRT
<213> ORGANISM: Homo sapiens

<400> SEQUENCE: 227

Arg Gly Ile Ala Cys Ala Arg Phe Ile Gly Asn Arg Thr Ile Tyr
1               5                   10                  15

<210> SEQ ID NO 228
<211> LENGTH: 15
<212> TYPE: PRT
<213> ORGANISM: Homo sapiens

<400> SEQUENCE: 228
```

```
Lys Thr Ile Thr Ala Thr Gly Val Leu Phe Val Arg Leu Gly Pro
1               5                   10                  15
```

<210> SEQ ID NO 229
<211> LENGTH: 19
<212> TYPE: PRT
<213> ORGANISM: Homo sapiens

<400> SEQUENCE: 229

```
Cys Gln Pro Tyr Arg Gly Ile Ala Cys Ala Arg Phe Ile Gly Asn Arg
1               5                   10                  15

Thr Ile Tyr
```

<210> SEQ ID NO 230
<211> LENGTH: 19
<212> TYPE: PRT
<213> ORGANISM: Homo sapiens

<400> SEQUENCE: 230

```
Gln Cys Ser Gln Phe Ala Ile Pro Ser Phe Cys His Phe Val Phe Pro
1               5                   10                  15

Leu Cys Asp
```

<210> SEQ ID NO 231
<211> LENGTH: 15
<212> TYPE: PRT
<213> ORGANISM: Homo sapiens

<400> SEQUENCE: 231

```
Glu Leu Cys Arg Asp Glu Cys Glu Val Leu Glu Ser Asp Leu Cys
1               5                   10                  15
```

<210> SEQ ID NO 232
<211> LENGTH: 15
<212> TYPE: PRT
<213> ORGANISM: Homo sapiens

<400> SEQUENCE: 232

```
Ala Asn Cys Met Arg Ile Gly Ile Pro Ala Glu Arg Leu Gly Arg
1               5                   10                  15
```

<210> SEQ ID NO 233
<211> LENGTH: 370
<212> TYPE: PRT
<213> ORGANISM: Homo sapiens

<400> SEQUENCE: 233

```
Glu Val Glu Val Leu Asp Pro Asn Asp Pro Leu Gly Pro Leu Asp Gly
1               5                   10                  15

Gln Asp Gly Pro Ile Pro Thr Leu Lys Gly Tyr Phe Leu Asn Phe Leu
                20                  25                  30

Glu Pro Val Asn Asn Ile Thr Ile Val Gln Gly Gln Thr Ala Ile Leu
            35                  40                  45

His Cys Lys Val Ala Gly Asn Pro Pro Pro Asn Val Arg Trp Leu Lys
        50                  55                  60

Asn Asp Ala Pro Val Val Gln Glu Pro Arg Arg Ile Ile Ile Arg Lys
65                  70                  75                  80

Thr Glu Tyr Gly Ser Arg Leu Arg Ile Gln Asp Leu Asp Thr Thr Asp
                85                  90                  95

Thr Gly Tyr Tyr Gln Cys Val Ala Thr Asn Gly Met Lys Thr Ile Thr
                100                 105                 110
```

-continued

```
Ala Thr Gly Val Leu Phe Val Arg Leu Gly Pro Thr His Ser Pro Asn
        115                 120                 125

His Asn Phe Gln Asp Asp Tyr His Glu Asp Gly Phe Cys Gln Pro Tyr
    130                 135                 140

Arg Gly Ile Ala Cys Ala Arg Phe Ile Gly Asn Arg Thr Ile Tyr Val
145             150                 155                 160

Asp Ser Leu Gln Met Gln Gly Glu Ile Glu Asn Arg Ile Thr Ala Ala
                165                 170                 175

Phe Thr Met Ile Gly Thr Ser Thr His Leu Ser Asp Gln Cys Ser Gln
            180                 185                 190

Phe Ala Ile Pro Ser Phe Cys His Phe Val Phe Pro Leu Cys Asp Ala
            195                 200                 205

Arg Ser Arg Thr Pro Lys Pro Arg Glu Leu Cys Arg Asp Glu Cys Glu
    210                 215                 220

Val Leu Glu Ser Asp Leu Cys Arg Gln Glu Tyr Thr Ile Ala Arg Ser
225                 230                 235                 240

Asn Pro Leu Ile Leu Met Arg Leu Gln Leu Pro Lys Cys Glu Ala Leu
            245                 250                 255

Pro Met Pro Glu Ser Pro Asp Ala Ala Asn Cys Met Arg Ile Gly Ile
            260                 265                 270

Pro Ala Glu Arg Leu Gly Arg Tyr His Gln Cys Tyr Asn Gly Ser Gly
    275                 280                 285

Met Asp Tyr Arg Gly Thr Ala Ser Thr Thr Lys Ser Gly His Gln Cys
    290                 295                 300

Gln Pro Trp Ala Leu Gln His Pro His Ser His Leu Ser Ser Thr
305             310                 315                 320

Asp Phe Pro Glu Leu Gly Gly Gly His Ala Tyr Cys Arg Asn Pro Gly
            325                 330                 335

Gly Gln Met Glu Gly Pro Trp Cys Phe Thr Gln Asn Lys Asn Val Arg
            340                 345                 350

Met Glu Leu Cys Asp Val Pro Ser Cys Ser Pro Arg Asp Ser Ser Lys
        355                 360                 365

Met Gly
    370
```

ANTI-ROR2 ANTIBODIES

CROSS-REFERENCE TO RELATED APPLICATIONS

This application is a 371 U.S. National Phase of PCT/IB2016/000255, international filing date Mar. 10, 2016, which claims the benefit of U.S. Provisional Application No. 62/131,128, filed Mar. 10, 2015, and U.S. Provisional Application No. 62/219,587, filed Sep. 16, 2015, each of which are hereby incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 74798PCT1_SeqList_ST25 2017-08-31.txt, created date: Aug. 31, 2017, file size: 107 kilobytes).

FIELD OF THE INVENTION

The invention relates to antibodies, and in particular, to antibodies exhibiting specificity for the Receptor tyrosine kinase-like Orphan Receptor 2 (ROR2), and to uses thereof, for example in the treatment of cancer. The invention extends to polynucleotide sequences encoding the antibodies and corresponding polypeptide sequences, and compositions comprising these polypeptide or polynucleotide molecules and therapeutic uses thereof. Diagnostic kits comprising these molecules and diagnostic methods using these molecules are also described. The invention also extends to antibody-drug conjugates and to uses thereof in therapy. The invention also extends to methods of making these molecules or antibodies.

BACKGROUND TO THE INVENTION

Osteosarcoma (OS) is the most prevalent malignant tumour of bone in children and adolescents.[1] It affects about 400 children under age 20 and about 500 adults (most between the ages of 15-30) every year in the USA, and approximately ⅓ of the 900 will die each year. A second peak in incidence occurs in the elderly, usually associated with an underlying bone pathology such as Paget's disease, medullary infarct, or prior irradiation.[1] Osteosarcoma is characterized by the direct formation of osteoid or bone by tumor cells, and displays aggressive growth in the primary lesion and high propensity for lung metastasis. The introduction of sophisticated adjuvant chemotherapy has dramatically improved the outcome for patients with localized disease, but has not altered the prognosis of patients with metastatic disease. Prior to 1975, curability ranged from 5 to 20%, even for patients with localized disease of the extremity.

Despite advances in therapeutic approaches initiated in the 1980s, culminating in an overall patient survival of 50-70%,[2] improvements since then have been relatively small. Options are particularly limited among patients refractory to standard chemotherapy. Late toxicities can be disabling and distressing among survivors.[2] Molecular alterations are potential targets for novel therapies that may be more selective.[4] For example, migration-invasion, resistance to anoikis and apoptosis, and angiogenesis have all been linked to the Wnt/β-catenin pathways.

Immunotherapy is another modality with high potential for sarcomas. Active immunotherapy offers a specific and possibly permanent protection from tumour relapse. Immunostimulatory agents for OS have included transfer factor,[5] interferon-alpha,[6] Muramyl Tripeptide-Phosphatidyl Ethanolamine (MTP-PE),[7] GM-CSF,[8] and IL-12.[9] Several potential antibody targets have been identified in OS; these include GD2,[10] CSPG4,[11] CD55,[12] HER-2,[13] and ROR2.[14] While anti-GD2 therapy is now an established target for neuroblastoma,[15] its painful treatment side effects are not acceptable for most adolescents or young adults. HER-2 expression is upregulated in OS, and the Phase II trial of trastuzumab was recently completed by Children's Oncology Group (COG). However, a limitation of trastuzumab treatment is that HER-2 expression is heterogeneous and often has low expression in osteosarcoma.[13] Osteosarcoma treatment remains an unmet medical need, and more effective, tumour-specific therapies are needed to improve overall outcome.

Neuroblastoma (NB) is the most common extracranial solid tumour of children. Of the 700 new cases a year in the USA, 50-60% of patients present with an unresectable primary tumour and metastases in bone marrow (BM).[16] Intensive induction chemotherapy and aggressive surgery have improved remission rates in young patients;[17-19] results, however, have been less encouraging for adolescents and adults whose NB tends to be chemoresistant.[20,21] A cure has remained elusive due to the difficulty in eradicating minimal residual disease (MRD), despite post-surgical use of local radiotherapy to control MRD in the primary site,[22] as well as myeloablative therapy (with stem-cell support) and treatment with the vitamin A derivative 13-cis-retinoic acid to control MRD in distant sites. Cure rate has been <30% at toxicity limits for stage 4 patients diagnosed at >18 months of age.[23]

Monoclonal antibody (mAb) therapy is an accepted treatment modality for cancers, with less than to mAbs currently FDA approved for treatment of solid tumours in adults, including colorectal, breast and non small cell lung cancer, squamous cell carcinoma and melanoma.[24,25]

This modality, however, has remained inadequately exploited for treatment of paediatric cancers. Unlike chemotherapy or radiation, mAb therapy is neither myelosuppressive nor genotoxic, generally with few long term toxicities. These are critical considerations for young children and adolescents. More importantly, mAbs are effective against cancer in blood, bone marrow and bone metastases found in high risk NB and OS. As a class of agents, the pharmacokinetics and toxicities of human or humanized IgG1 antibodies have been extensively studied. In addition, antibodies can carry cytotoxic payloads, which can be immune based, radioisotopes, toxins or enzymes, thereby increasing the options for targeted therapy. NB is a disease where mAbs have definitively shown clinical benefit. mAbs can mediate highly efficient antibody-dependent cellular cytotoxicity (ADCC) of NB in the presence of human white cells. mAbs also induce complement-dependent cytotoxicity (CDC) because NB cells lack decay accelerating factor CD55[26] and homologous restriction factor CD59.[27] Moreover, complement deposition on NB cells enhances ADCC through activation of the iC3b receptor on neutrophils.[28,29] is an adhesion molecule abundant on NB and is also widely expressed among melanoma, small cell lung cancer, bone or soft tissue sarcoma, retinoblastoma and brain tumor.[30] GD2 is rarely expressed in normal tissues except neurons, skin cells and pain fibers. Scintigraphy studies using radiolabeled anti-GD2 mAbs have confirmed specific tumor targeting.[30]

At least two antibody families have been tested clinically, i.e. murine 3F8[31] and ch14.18[32] Ch14.18 was constructed from the murine mAb 14.18 variable region and human IgG1κ constant regions.[33] The antibody demonstrates ADCC and CDC of NB and melanoma cells in vitro.[34-37] COG completed a randomized phase III trial that clearly demonstrated the efficacy of combination therapy using anti-GD2 ch14.18 with GM-CSF and IL-2 for prevention of NB relapse.[15] However, despite this clinical success, painful side effects and the requirement of cytokines to achieve benefit limit the broad utility of chL4.18.

ROR1 and ROR2 are emerging targets for antibody based immunotherapy[60]. ROR2 is a type-I transmembrane receptor tyrosine kinase important in developmental biology. The extracellular region of ROR2 contains an immunoglobulin (Ig) domain, a cysteine-rich domain (CRD), also called a Frizzled domain, and a Kringle (Kr) domain. All three domains are involved in protein-protein interactions. Intracellularly, ROR2 possesses a tyrosine kinase (TK) domain and a proline-rich domain (PRD) straddled by two serine/threonine-rich domains. ROR2 is normally expressed at high levels during development, playing a key role in skeletal and neural organogenesis, but then expression is suppressed in adult tissues.[38] ROR2 has been shown to play a role in establishing cellular polarity and in tumor-like behavior, such as cell migration and cell invasiveness.[14,39,40] Wnt5a and 5b, glycoproteins critical in carcinogenesis, have been identified to regulate these functions by binding and activating ROR2.44[14,41,42] Wnt5a/b binding to ROR2 and its co-receptor, Frizzled (Fz), can activate the JNK pathway and filamin A to regulate cell migration and invasion, Rac1 and Rho A to regulate cell polarity, Src family members to modulate the expression of matrix metalloproteases such as MMP[1,2,13], and inhibit the canonical Wnt pathways.[40,41]

ROR2 is an embryonic protein. In mice, it is expressed only during the developmental stage. ROR2 expression is quickly silenced after birth, and is normally undetectable or expressed at very low levels in adult tissues.[38] ROR2-deficient mice exhibit widespread skeletal abnormalities, ventricular septal defects in the heart, and respiratory dysfunction, leading to neonatal lethality.[38,43-46] In human, homozygous mutations in ROR2 have been shown to be responsible for Robinow syndrome, a skeletal dysplasia syndrome characterized by generalized limb shortening, segmental defects of the spine, and dysmorphic facial appearance, while heterozygous mutations have been found in patients with dominant brachydactyly B1, characterized by terminal deficiency of fingers and toes.[47,48]

ROR2 is highly expressed in several types of human cancer tissues, such as OS,[14] renal cell carcinoma,[49] gastric cancer,[50,51] malignant melanoma,[52] oral squamous cell carcinoma,[53] prostate cancer,[54] leimyosarcoma[61], Gastrointestinal Stromal Tumour (GIST)[61], and NB (Cheung et al., unpublished results). ROR2 is transactivated in a majority of OS, and knockdown of ROR2 in OS cell lines results in significantly inhibited cell proliferation, migration and invasion.[14,55] Evidence links Wnt5a and ROR2 within OS, where ROR2 has an additional role in the degradation of the extracellular matrix and invadopodia formation.[55] Research has also shown that expression of ROR2 tends to increase as the degree of malignancy rises in oral squamous cell carcinoma and in metastatic nodules of melanoma.[52,53] In a xenograft metastasis model, silencing ROR2 significantly decreased lung metastasis of melanoma cells.[52] Like its mouse counterpart, human ROR2 expression cannot be detected in normal adult tissues, except for low levels in stomach and thyroid.[14] Overexpression of ROR2 appears to strongly correlate with poor survival in patients with NB. This differential expression of ROR2 between human cancers and normal tissues makes it an excellent therapeutic target.

Therapeutic antibodies have achieved great success in treatment of cancer, autoimmune and infectious diseases in the past decade. As the fastest growing class of innovative drugs, there are more than 350 candidates in different phases of clinical trials. The proposed research is for the development of a highly-specific antibody drug against ROR2 for treatment of various cancers, such as osteosarcoma and neuroblastoma. The unique expression profile of ROR2 suggests that a successful ROR2 specific antibody drug can be expected to have high potency and low side effects compared to existing treatments. An effective new antibody therapy could potentially prolong survival without the late effects for children and young adults. In the modern era of personalized medicine, advances in the production, safety and efficacy of monoclonal antibody drugs for orphan indications should make antibody cancer therapy attractive from a public health finance standpoint as well.

BRIEF DESCRIPTION OF THE DRAWINGS

For a better understanding of the invention, and to show how embodiments of the same may be carried into effect, reference will now be made, by way of example, to the accompanying Figures, in which:—

FIG. 1 is a Kaplan Meier curve showing that high expression levels of ROR2 correlate with poorer overall survival among neuroblastoma patients. The Kaplan Meier curve was generated using the publically available database and software algorithm from the Oncogenomics Section, Pediatric—Oncology Branch of the National Cancer Institute. http://home.ccr.cancer.gov/oncology/oncogenomics/). The database used for these plots was previously published.[56]

FIG. 2 is a flow diagram showing how fully human antibody candidates were identified and generated using a human single-chain variable fragment (scFv) antibody phage display. Protein panning against human ROR2 ECD-Fc fusion protein was conducted using Eureka Therapeutics' proprietary fully human phage libraries. ECD is extracellular domain. The human ROR2 ECD-specific phage antibody binders were enriched.

FIG. 3 shows the results of a protein ELISA for ROR2 conducted using specific scFv phage antibody clones. ELISA plates were coated with human ROR2 ECD-Fc fusion protein, control-Fc fusion protein, or PBS alone as blank control, respectively. Individual phage clones from enriched phage display panning pools against ROR2 ECD-Fc fusion protein were incubated in the coated plates. Binding of the phage clones was detected by HRP-conjugated anti-M13 antibodies and developed using HRP substrate. The absorbance was read at 450 nm.

FIG. 4 is a schematic description of the phage competition ELISA for ROR2-specific phage antibody clones with ROR2-ECD Fc fusion proteins. The assay was used to rank the ROR2 human antibodies by their binding affinity against ROR2-ECD Fc fusion proteins.

FIG. 5 is a graph showing the results of a protein ELISA, which shows phage antibody clones capable of binding to ROR2. ELISA plates were coated with human ROR2 ECD-Fc fusion protein, human ROR1 ECD-Fc fusion protein, control-Fc fusion protein, or PBS alone as blank control, respectively. Phage clones #240, #241, #081, #090, #024, #027, #005 and #023, which target the ROR2 ECD-Fc fusion protein, were incubated in the coated plates. Binding of the phage clones was detected by HRP-conjugated anti-M13 antibodies and developed using HRP substrate. The absorbance was read at 450 nm.

FIG. 6 is a representative figure of a FACS analysis of the ROR2-specific phage antibody clone #90. Phage clone #90 was incubated with HCT116 cells (ROR1(+) and ROR2(+), see FIG. 8), then with biotin-labeled anti-M13 antibody after washing. Finally FITC-labeled streptavidin was added to the reaction after washing again. The binding was measured by FACS and expressed as mean fluorescence intensity (MFI). Cells incubated with M13 K07 helper phage and cells only were used as negative controls.

FIG. 7 is representative figure of a FACS analysis of the ROR2-specific phage antibody clone #90. Phage clone #90 was incubated with Jurkat cells (ROR1(−) a=nd ROR2(−) see FIG. 8), then with biotin-labeled anti-M13 antibody after washing. Finally FITC-labeled streptavidin was added to the reaction after washing again. The binding was measured by FACS and expressed as mean fluorescence intensity (MFI). Cells incubated with M13 K07 helper phage and cells only were used as negative controls.

FIG. 8 is a FACs analysis of HCT116 and Jurkat cells binding to commercial ROR1 antibody (control 2)—a goat-anti ROR1 polyclonal antibody (R&D system), ROR2 antibody (control 1)—a goat-anti ROR2 polyclonal antibody (R&D system) and cell only negative controls.

FIG. 9a is a mammalian expression vector map for the light chain of embodiments of antibodies according to the invention, and FIG. 9b is a proprietary mammalian expression vector map for the heavy chain of embodiments of antibodies according to the invention.

FIG. 10 is a SDS PAGE of full-length human IgG1 ROR2 antibody clone #90.

FIG. 11 shows the results of a ROR2 epitope mapping ELISA result conducted using ROR2 clone #90.

FIG. 12 indicates where the binding epitope of ROR2 antibody, #90, is located with respect to the primary structure of ROR2. ROR2 #90 recognizes a linear epitope KTI-TATGVLFVRLGP (SEQ ID No. 228), which is located in the C-terminal of the ROR2 Ig domain. This sequence is not shared by ROR1 or any other human proteins when determined by PBLAST.

FIG. 13 shows the binding specificity of the following five purified full-length IgG1 antibodies: clone #23, #27, #90, #240 and #241. ELISA assays were carried out as follows: 20 ng of ROR2 ECD recombinant protein were coated onto 96-well ELISA plates overnight at 4° C. Anti-ROR2 IgG1s at different dilutions were incubated in the antigen wells for 1 hour at RT. Bound IgG1s were detected with anti-human Fc-HRP antibody (1:10,000, BD Biosciences). The 2,2'-azino-bis-(3-ethylbenzthiazoline-6-sulfonic acid) substrate (Sigma-Aldrich) was added and the reaction was read at 490 nm. These ELISAs confirmed the binding of the IgGs to ROR2 ECD. Meanwhile, all the ROR2 antibodies tested were stable after multiple freeze-and-thaw (F&T) cycles, demonstrated by ROR2 ECD ELISA. The diamond curves represent antibody-antigen binding of non-frozen ROR2 antibodies; the triangle curves represent antibody-antigen binding of antibodies after multiple freeze-and-thaw cycles. Each point represents triplicate results.

FIG. 14 shows the results of an ELISA which shows that full length ROR2 hIgG1 antibodies based on clones #23, #27 and #90 bind to a ROR2 positive cancer cell line K562. ROR2 hIgG1 antibodies (2 ug/ml or 10 ug/ml) were incubated with K562 cells, then washed with PBS, and stained with FTC-conjugated anti-human IgG (H+L) secondary antibody (Vector Lab). Then the cells were washed again in PBS and analyzed by flow cytometry. Goat anti-human ROR2 polyclonal antibody (R&D system) was used as positive control. Negative control include cell only control, anti-human IgG secondary antibody control and anti-goat antibody control.

FIG. 15 is an SDS PAGE of ROR2 bispecific antibody (ROR2 BsAb antibody) clones performed using a non-reducing gel.

FIGS. 16 to 20 are the results of various CTL assays, which show that ROR2 BsAb antibodies kill cancer cells in a ROR2-dependent manner in in vitro T cell killing assays. Tumour cytotoxicity was assayed by $^{51}$Cr release as previously described[50], and EC50 was calculated using Sigma-Plot software. Effector T cells were purified from human PBMC using Pan T cell isolation kit, and then activated and expanded with CD3/CD28 Dynabeads (Invitrogen) according to manufacturer's protocol. Activated T cells (ATC) were cultured and maintained in F10 medium plus 30 U/ml IL-2, and used at day 14-21. CD3+ T cells were above 99% by FACS analysis. The antibodies killed multiple ROR2 positive cancer cell lines (U2OS, BE(1)N, LAN-1 and AU565) efficiently in the in vitro T cell killing assays, but none of the ROR2 BsAb antibodies killed the ROR2 negative cancer cell line M14 (see FIGS. 16-19). In FIG. 20, the same T cell killing assays were conducted against a ROR2 negative cancer cell line, M14 cells.

FIG. 21 shows that BsAb antibodies, ROR2 #90 and ROR2 #240, are capable of shrinking a human breast cancer tumour in the presence of human PBMCs in vivo. Purified human PBMC (discard from blood bank) were mixed with MCF7 breast cancer cells (1:1 ratio, 7 million each) in Matrigel (BD Biosciences) and implanted subcutaneously (sc) into DKO mice in the right flank. Daily iv injections of 10 μg of BsAb antibody was given on days 5, 6, 7, 8, 9, 11, 12, 13, 14, 15 (a total of to days) post implantation. Daily iv injections of 20 μg herceptin were given on days 4, 7, 11, 14, 18, 21 (a total of 6 doses) post implantation. Tumour size was measured by calipers once a week, and tumor volumes were calculated using the approximated formula: V=0.5* (length*width*width). % growth was then calculated.

FIG. 22 shows that a ROR2 BsAb (clone #90-BsAb) antibody is capable of shrinking a human neuroblastoma tumour in vivo. Purified PBMC (discard from blood bank) were mixed with SKNBE(2)S neuroblastoma cells (1:2 ratio, 2.5×106 PBMC, 5×106 tumor cells) in Matrigel (BD Biosciences) and implanted subcutaneously (sc) into the right flank of DKO mice. Daily injections of 10 μg of antibody were given on days 4, 5, 6, 7, 8, 11, 12, 13, 14, 15 (a total of to days) post implantation. Tumour size was measured by calipers once a week, and tumor volumes were calculated using the approximated formula: V=0.5* (length*width*width). % growth was then calculated.

FIG. 23 shows the results of an in vitro characterization of ROR2 #90 chimeric antibody receptor (CAR) performed using FACS. ROR2 #90 CAR and control 901 CAR were constructed using retroviral CAR expression vector pMSCV-BBz-ires-EGFP. Both CAR structures were evaluated using stable transduction of human T lymphocytes. PG13 (GaLV pseudotyped) packaging cell line was used for transfection of pMSCV plasmids. Human T-cells were used for transduction after 4-day stimulation and expansion with CD3/CD28 beads (Dynabeads®, Invitrogen) in the presence of interleukine-2 at 30 U/ml. Cell free supernatant was filtered and applied on T-cells in Retronectin (Takara) coated 6-well plates at 48 and 72 hours after PG13 virus producer cell line transfection. Transduction efficiency was assessed by FACS using biotinylated Protein-L (primary) antibody (GeneScript) and PE-conjugated (secondary) antibody (BD Biosciences). Repeat FACS analyses were done at 72 hours and every 3-4 days thereafter. Level of transduction was about 50% for both constructs. Of note, detected GFP expression was miniscule (1-3%).

FIG. 24 shows the results of a 4-hour $^{51}$Cr release assay, which was used to assess the functional activity of transduced T cells. T cells transduced with pMSCV 3F8-BBz-CAR served as control effectors. Effector-to-target ratios were 5:1, 10:1, 25:1. Two neuroblastoma cell lines, which express ROR2, were used as targets: SKNMM with 71% ROR2 positivity, and SKNSH with 99% positivity by FACS. This Figure shows the ROR2 #90 CAR specific killing against SKNSH cells when compared to control. Clone #90-CAR T cells exhibited higher level of cytotoxicity against SKNSH as compared to 901 control CAR T cells at E:T ratios 10:1 and 25:1.

DETAILED DESCRIPTION OF THE INVENTION

The inventors focused their investigations on Receptor Tyrosine Kinase-Like Orphan Receptor 2 (ROR2), as they considered it to be a promising novel therapeutic target for the treatment of various types of cancer, such as neuroblastoma and osteosarcoma, especially in children and adolescents. However, the inventors found that a significant problem involved in the development of effective ROR2-targeting monoclonal antibody diagnostics and therapies is that ROR2 has 62% amino acid sequence identity with ROR1. ROR1 is expressed in adipose tissues and early stages of normal B cell development[62]. Accordingly, an effective antibody treatment directed at ROR2 for neuroblastoma (for example) must be able to avoid ROR1 cross reactivity in normal (non-cancerous) tissues. Similarly, an effective antibody treatment directed at ROR2 for osteosarcoma (for example) must be able to avoid cross reactivity with adipose tissues and early B cells.

One way to overcome the challenge of the sequence identity between ROR1 and ROR2 is to identify a high affinity antibody that can bind to ROR2 positive cancer cells without cross reactivity with ROR1.

The objective of the present invention therefore is to develop highly-specific and high-affinity anti-ROR2 monoclonal antibodies that will target and kill cancerous cells with minimal side effects to normal tissues. By panning against the human ROR2 extracellular domain (ECD) protein using a fully-human antibody phage library, the inventors have now been able to isolate a highly specific human ROR2-specific antibody with no cross reactivity to ROR1.

Therefore, according to a first aspect of the invention, there is provided a human anti-Receptor Tyrosine Kinase-Like Orphan Receptor 2 (ROR2) antibody, or a functional fragment thereof.

Advantageously, the inventors have isolated the first ever fully human ROR2-immunospecific antibody, and developed a ROR2-targeting antibody therapy for ROR2-positive cancer types, such as neuroblastoma or osteosarcoma, thereby addressing an unmet medical need. Targeting ROR2 by antibodies according to the invention for cancer therapy is based on the important scientific finding that ROR2 is aberrantly expressed in cancer cells, but expressed at low levels in normal blood cells and normal adult tissues (see Example 11), and therefore provides a highly specific therapy which targets only cancerous cells and tumours (see Examples 8 and 9).

As described in the Examples, several different embodiments of the fully human and unique anti-ROR2 antibody of the invention have been isolated, each of these antibodies being capable of recognizing distinct binding epitopes on ROR2 protein with surprisingly high affinity (i.e. antibody clone #16, #23, #24, #27, #84, #90, #93, #96, #121, #159, #173, #240 and #241). Advantageously, full length antibodies of the invention can: (i) mediate complement-dependent cytotoxicity (CDC), (ii) mediate antibody-dependent cellular cytotoxicity (ADCC) against various ROR2-positive cancer cell lines, and (iii) shrink the size of ROR2-positive tumours, as shown in Example 9. The inventors believe that this is the first time that a fully human anti-ROR2 antibody has been isolated, identified and sequenced. The antibodies of the invention therefore present a highly effective therapeutic agent when used alone, or as a vehicle that is capable of delivering potent anti-cancer reagents, or as an engineered antibody exhibiting enhanced immune functions. Additionally, the antibody of the invention may also be used as a diagnostic or prognostic tool.

The invention extends to both whole antibodies (i.e. immunoglobulins) with immunospecificity for a ROR2 protein, preferably an extracellular domain thereof, as well as to functional fragments thereof. Such fragments retain at least one antigen binding region of the corresponding full-length antibody. The antibody or functional fragment thereof may comprise a human monoclonal or polyclonal antibody or functional fragment thereof.

The antibody or functional fragment may be monovalent, divalent or polyvalent. Monovalent antibodies are dimers (HL) comprising a heavy (H) chain associated by a disulphide bridge with a light chain (L). Divalent antibodies are tetramer (H2L2) comprising two dimers associated by at least one disulphide bridge. Polyvalent antibodies may also be produced, for example by linking multiple dimers. The basic structure of an antibody molecule consists of two identical light chains and two identical heavy chains which associate non-covalently and can be linked by disulphide bonds. Each heavy and light chain contains an amino-terminal variable region of about 110 amino acids, and constant sequences in the remainder of the chain. The variable region includes several hypervariable regions, or Complementarity Determining Regions (CDRs), that form the antigen-binding site of the antibody molecule and determine its specificity for the antigen, i.e. ROR2 or an epitope thereof. On either side of the CDRs of the heavy and light chains is a framework region, a relatively conserved sequence of amino acids that anchors and orients the CDRs. Antibody fragments may include a bi-specific antibody (BsAb) or a chimeric antigen receptor (CAR).

The constant region consists of one of five heavy chain sequences (μ, γ, ζ, α, or ε) and one of two light chain sequences (κ or λ). The heavy chain constant region sequences determine the isotype of the antibody and the effector functions of the molecule.

As used herein, the term "human antibody" can mean an antibody, such as a monoclonal antibody, which comprises substantially the same heavy and light chain CDR amino acid sequences as found in a particular human antibody exhibiting immunospecificity for ROR2 protein. An amino acid sequence, which is substantially the same as a heavy or light chain CDR, exhibits a considerable amount of sequence identity when compared to a reference sequence. Such identity is definitively known or recognizable as representing the amino acid sequence of the particular human antibody. Substantially the same heavy and light chain CDR amino acid sequence can have, for example, minor modifications or conservative substitutions of amino acids. Such a human antibody maintains its function of selectively binding to ROR2 protein.

The term "human monoclonal antibody" can include a monoclonal antibody with substantially or entirely human CDR amino acid sequences produced, for example by recombinant methods such as production by a phage library, by lymphocytes or by hybridoma cells.

The term "humanised antibody" can mean an antibody from a non-human species (e.g. mouse) whose protein sequences have been modified to increase their similarity to antibodies produced naturally in humans.

The antibody may be a recombinant antibody. The term "recombinant human antibody" can include a human antibody produced using recombinant DNA technology.

The term "antigen binding region" can mean a region of the antibody having specific binding affinity for its target antigen, for example, the ROR2 protein, or an epitope thereof. The binding region may be a hypervariable CDR or a functional portion thereof. The term "functional portion" of a CDR can mean a sequence within the CDR which shows specific affinity for the target antigen. The functional portion of a CDR may comprise a ligand which specifically binds to ROR2 protein.

The term "CDR" can mean a hypervariable region in the heavy and light variable chains. There may be one, two, three or more CDRs in each of the heavy and light chains of the antibody. Normally, there are at least three CDRs on each chain which, when configured together, form the antigen-binding site, i.e. the three-dimensional combining site with which the antigen binds or specifically reacts. It has however been postulated that there may be four CDRs in the heavy chains of some antibodies.

The definition of CDR also includes overlapping or subsets of amino acid residues when compared against each other. The exact residue numbers which encompass a particular CDR or a functional portion thereof will vary depending on the sequence and size of the CDR. Those skilled in the art can routinely determine which residues comprise a particular CDR given the variable region amino acid sequence of the antibody.

The term "functional fragment" of an antibody can mean a portion of the antibody which retains a functional activity. A functional activity can be, for example antigen binding activity or specificity. A functional activity can also be, for example, an effector function provided by an antibody constant region. The term "functional fragment" is also intended to include, for example, fragments produced by protease digestion or reduction of a human monoclonal antibody and by recombinant DNA methods known to those skilled in the art. Human monoclonal antibody functional fragments include, for example individual heavy or light chains and fragments thereof, such as VL, VH and Fd; monovalent fragments, such as Fv, Fab, and Fab'; bivalent fragments such as F(ab')$_2$; single chain Fv (scFv); and Fc fragments.

The term "VL fragment" can mean a fragment of the light chain of a human monoclonal antibody which includes all or part of the light chain variable region, including the CDRs. A VL fragment can further include light chain constant region sequences.

The term "VH fragment" can means a fragment of the heavy chain of a human monoclonal antibody which includes all or part of the heavy chain variable region, including the CDRs.

The term "Fd fragment" can mean the heavy chain variable region coupled to the first heavy chain constant region, i.e. VH and CH-1. The "Fd fragment" does not include the light chain, or the second and third constant regions of the heavy chain.

The term "Fv fragment" can mean a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about 110 amino acids of both the heavy and light chains.

The term "Fab fragment" can mean a monovalent antigen-binding fragment of a human monoclonal antibody that is larger than an Fv fragment. For example, a Fab fragment includes the variable regions, and all or part of the first constant domain of the heavy and light chains. Thus, a Fab fragment additionally includes, for example, amino acid residues from about 110 to about 220 of the heavy and light chains.

The term "Fab' fragment" can mean a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "F(ab')$_2$ fragment" can mean a bivalent antigen-binding fragment of a human monoclonal antibody. An F(ab')$_2$ fragment includes, for example, all or part of the variable regions of two heavy chains—and two light chains, and can further include all or part of the first constant domains of two heavy chains and two light chains.

The term "single chain Fv (scFv)" can mean a fusion of the variable regions of the heavy (VH) and light chains (VL) connected with a short linker peptide.

The term "bispecific antibody (BsAb)" can mean a bispecific antibody comprising two scFv linked to each other by a shorter linked peptide.

The term "peptide" as used herein refers to a polymer of amino acid residues typically ranging in length from 2 to about 30, or to about 40, or to about 50, or to about 60, or to about 70 residues. In certain embodiments the peptide ranges in length from about 2, 3, 4, 5, 7, 9, 10, or 11 residues to about 60, 50, 45, 40, 45, 30, 25, 20, or 15 residues. In certain embodiments the peptide ranges in length from about 8, 9, 10, 11, or 12 residues to about 15, 20 or 25 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an a-ester, a f3-ester, a thioamide, phosphonamide, carbamate, hydroxylate, and the like (see, e.g., Spatola, (1983) Chem. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "residue" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, nethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-nmethyllysine, n-methylvaline, norvaline, norleucine, ornithine, and the like. These modified amino acids are illustrative and not intended to be limiting.

"f3-peptides" comprise of "f3 amino acids", which have their amino group bonded to the f3 carbon rather than the a-carbon as in the 20 standard biological amino acids. The only commonly naturally occurring f3 amino acid is f3-alanine.

Where an amino acid sequence is provided herein, L-, D-, or beta amino acid versions of the sequence are also contemplated as well as retro, inversion, and retroinversion isoforms. In addition, conservative substitutions are contemplated. Non-protein backbones, such as PEG, alkane, ethylene bridged, ester backbones, and other backbones are also contemplated. Also fragments ranging in length from about 5, 6, 7, 8, 9, 10, 11, 12, 13, 14, 15, 16, 17, 18, 19, 20, 21, 22, 23, 24, or 25 amino acids up to the full length minus one amino acid of the peptide are contemplated where the fragment retains at least 50%, preferably at least 60% 70% or 80%, more preferably at least 90%, 95%, 98%, 99%, or at least 100% of the activity of the full length peptide are contemplated.

In certain embodiments, conservative substitutions of the amino acids comprising any of the sequences described herein are contemplated. In various embodiments one, two, three, four, or five different residues are substituted. The term "conservative substitution" is used to reflect amino acid substitutions that do not substantially alter the activity of the molecule. Typically conservative amino acid substitutions involve substitution one amino acid for another amino acid with similar chemical properties (e.g. charge or hydrophobicity). Certain conservative substitutions include "analog substitutions" where a standard amino acid is replaced by a non-standard (e.g., rare, synthetic, etc) amino acid differing minimally from the parental residue. Amino acid analogs are considered to be derived synthetically from the standard amino acids without sufficient change to the structure of the parent, are isomers, or are metabolite precursors. Examples of such "analog substitutions" include, but are not limited to, 1) Lys-Om, 2) Leu-Norleucine, 3) LysLys[TFA], 4) Phe-Phe [Gly], and 5) 8-amino butylglycine-~-amino hexylglycine, where Phe[gly] refers to phenylglycine (a Phe derivative with a H rather than CH3 component in the R group), and Lys[TFA] refers to a Lys where a negatively charged ion (e.g., TFA) is attached to the amine R group.

Other conservative substitutions include "functional substitutions" where the general chemistries of the two residues are similar, and can be sufficient to mimic or partially recover the function of the native peptide. Strong functional substitutions include, but are not limited to 1) Gly/Ala, 2) Arg/Lys, 3) Ser/Tyr/Thr, 4) Leu/He/Val, 5) Asp/Glu, 6) Gln/Asn, and 7) Phe/Trp/Tyr, while other functional substitutions include, but are not limited to 8) Gly/Ala/Pro, 9) Tyr/His, 10) Arg/Lys/His, 11) Ser/Thr/Cys, 12) Leu/Ile/VaVMet, and 13) Met/Lys (special case under hydrophobic conditions). Various "broad conservative substations" include substitutions where amino acids replace other amino acids from the same biochemical or biophysical grouping. This is similarity at a basic level and stems from efforts to classify the original 20 natural amino acids. Such substitutions include 1) nonpolar side chains: Gly/AlaN al/Leu/Ile/Met/Pro/Phe/Trp, and/or 2) uncharged polar side chains Ser/Thr/Asn/Gln/Tyr/Cys. In certain embodiments broad-level substitutions can also occur as paired substitutions. For example, Any hydrophilic neutral pair [Ser, Thr, Gln, Asn, Tyr, Cys]+[Ser, Thr, Gln, Asn, Tyr, Cys] can may be replaced by a charge-neutral charged pair [Arg, Lys, His]+[Asp, Glu]. The following six groups each contain amino acids that, in certain embodiments, are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W). Where amino acid sequences are disclosed herein, amino acid sequences comprising, one or more of the above-identified conservative substitutions are also contemplated.

One skilled in the art knows that the exact boundaries of a fragment of a human monoclonal antibody are not important, so long as the fragment maintains a functional activity. Using well-known recombinant methods, one skilled in the art can engineer a polynucleotide sequence to express a functional fragment with any endpoints desired for a particular application. A functional fragment of the antibody may comprise or consist of fragment with substantially the same heavy and light chain variable regions as the human antibody.

Preferably, the functional fragment, with respect to the first aspect of the invention, is ROR2-specific. Hence, the functional fragment preferably includes fragments wherein at least one of the binding region sequences has substantially the same amino acid sequence as the binding region sequences of the antibody, more preferably the ROR2-specific human antibody. The functional fragment may comprise or consist of any of the fragments selected from a group consisting of VH, VL, Fd, Fv, Fab, Fab', scFv, F (ab')$_2$ and Fe fragment.

The functional fragment may comprise or consist of any one of the antigen binding region sequences of the VL, any one of the antigen binding region sequences of the VH, or a combination of VL and VH antigen binding regions of a human antibody. The appropriate number and combination of VH and VL antigen binding region sequences may be determined by those skilled in the art depending on the desired affinity and specificity and the intended use of the functional fragment. Functional fragments of antibodies may be readily produced and isolated using methods well known to those skilled in the art. Such methods include, for example, proteolytic methods, recombinant methods and chemical synthesis. Proteolytic methods for the isolation of functional fragments comprise using human antibodies as a starting material. Enzymes suitable for proteolysis of human immunoglobulins may include, for example, papain, and pepsin. The appropriate enzyme may be readily chosen by one skilled in the art, depending on, for example, whether monovalent or bivalent fragments are required. For example, papain cleavage results in two monovalent Fab' fragments that bind antigen and an Fc fragment. Pepsin cleavage, for example, results in a bivalent F (ab') fragment. An F (ab')$_2$. fragment of the invention may be further reduced using, for example, DTT or 2-mercaptoethanol to produce two monovalent Fab' fragments.

Functional fragments produced by proteolysis may be purified by affinity and column chromatographic procedures. For example, undigested antibodies and Fc fragments may be removed by binding to protein A. Additionally, functional fragments may be purified by virtue of their charge and size, using, for example, ion exchange and gel filtration chromatography. Such methods are well known to those skilled in the art.

The human antibody or functional fragment thereof may be produced by recombinant methodology. Preferably, one initially isolates a polynucleotide encoding desired regions of the antibody heavy and light chains. Such regions may include, for example, all or part of the variable region of the heavy and light chains. Preferably, such regions can particularly include the antigen binding regions of the heavy and light chains, preferably the antigen binding sites, most preferably the CDRs.

The polynucleotide encoding the human antibody or functional fragment of the invention may be produced using methods known to those skilled in the art. The polynucleotide encoding the antibody or a functional fragment thereof may be directly synthesized by methods of oligonucleotide synthesis known in the art. Alternatively, smaller fragments may be synthesized and joined to form a larger functional fragment using recombinant methods known in the art.

As used herein, the term "immunospecificity" can mean the binding region is capable of immunoreacting with a ROR2 protein, by specifically binding therewith. The antibody or functional fragment thereof can selectively interact with an antigen (e.g. ROR2 peptide) with an affinity constant of approximately $10^{-5}$ to $10^{-13}$ $M^{-1}$, preferably $10^{-6}$ to $10^{-9}$ $M^{-1}$, even more preferably, $10^{-10}$ to $10^{-12}$ $M^{-1}$.

As shown in Table 7, kinetic binding analysis confirmed specific binding of the full length IgG1 antibodies to hROR2-ECD, with an equilibrium dissociation constant ($K_D$) in the picomolar range. Thus, preferably the $K_D$ of the antibody or fragment thereof for ROR2 may be less than $1\times10^{-9}$, preferably less than $1\times10^{-10}$, more preferably less than $1\times10^{-11}$. The antibody or fragment thereof may exhibit an $IC_{50}$ for ROR2 of about $10^{-7}$ to $10^{-11}$ $M^{-1}$ or $10^{-7}$ to $10^{-9}$ $M^{-1}$. The IC50 may be calculated using a competition ELISA.

The term "immunoreact" can mean the binding region is capable of eliciting an immune response upon binding with a ROR2 protein, or an epitope thereof.

The term "epitope" can mean any region of an antigen with ability to elicit, and combine with, a binding region of the antibody or fragment thereof.

As shown in FIGS. 21 and 22, the antibody or fragment thereof according to the invention may be capable of mediating killing or shrinking ROR2-expressing tumour cells. The antibodies or fragments according to the invention may be used to assist Complement-Dependent Cytotoxicity (CDC) and/or via Antibody-Dependent Cellular Cytotoxicity (ADCC). The antibody or fragment may be capable of inhibiting cancer cell proliferation.

The term "ROR2" can refer to family 2 of the receptor tyrosine kinase-like orphan receptors. The DNA sequence encoding one embodiment of human ROR2 is provided herein as SEQ ID No.224, as follows:

[SEQ ID No. 224]
ATGGCCCGGGGCTCGGCGCTCCCGCGGCGGCCGCTGCTGTGCATCCCGGC

CGTCTGGGCGGCCGCCGCGCTTCTGCTCTCAGTGTCCCGGACTTCAGGTG

-continued
AAGTGGAGGTTCTGGATCCGAACGACCCTTTAGGACCCCTTGATGGGCAG

GACGGCCCGATTCCAACTCTGAAAGGTTACTTTCTGAATTTTCTGGAGCC

AGTAAACAATATCACCATTGTCCAAGGCCAGACGGCAATTCTGCACTGCA

AGGTGGCAGGAAACCCACCCCCTAACGTGCGGTGGCTAAAGAATGATGCC

CCGGTGGTGCAGGAGCCGCGGCGGATCATCATCCGGAAGACAGAATATGG

TTCACGACTGCGAATCCAGGACCTGGACACGACAGACACTGGCTACTACC

AGTGCGTGGCCACCAACGGGATGAAGACCATTACCGCCACTGGCGTCCTG

TTTGTGCGGCTGGGTCCAACGCACAGCCCAAATCATAACTTTCAGGATGA

TTACCACGAGGATGGGTTCTGCCAGCCTTACCGGGGAATTGCCTGTGCAC

GCTTCATTGGCAACCGGACCATTTATGTGGACTCGCTTCAGATGCAGGGG

GAGATTGAAAACCGAATCACAGCGGCCTTCACCATGATCGGCACGTCTAC

GCACCTGTCGGACCAGTGCTCACAGTTCGCCATCCCATCCTTCTGCCACT

TCGTGTTTCCTCTGTGCGACGCGCGCTCCCGGACACCCAAGCCGCGTGAG

CTGTGCCGCGACGAGTGCGAGGTGCTGGAGAGCGACCTGTGCCGCCAGGA

GTACACCATCGCCCGCTCCAACCCGCTCATCCTCATGCGGCTTCAGCTGC

CCAAGTGTGAGGCGCTGCCCATGCCTGAGAGCCCCGACGCTGCCAACTGC

ATGCGCATTGGCATCCCAGCCGAGAGGCTGGGCCGCTACCATCAGTGCTA

TAACGGCTCAGGCATGGATTACAGAGGAACGGCAAGCACCACCAAGTCAG

GCCACCAGTGCCAGCCGTGGGCCCTGCAGCACCCCCACAGCCACCACCTG

TCCAGCACAGACTTCCCTGAGCTTGGAGGGGGGCACGCCTACTGCCGGAA

CCCCGGAGGCCAGATGGAGGGCCCCTGGTGCTTTACGCAGAATAAAAACG

TACGCATGGAACTGTGTGACGTACCCTCGTGTAGTCCCCGAGACAGCAGC

AAGATGGGGATTCTGTACATCTTGGTCCCCAGCATCGCAATTCCACTGGT

CATCGCTTGCCTTTTCTTCTTGGTTTGCATGTGCCGGAATAAGCAGAAGG

CATCTGCGTCCACACCGCAGCGGCGACAGCTGATGGCCTCGCCCAGCCAA

GACATGGAAATGCCCCTCATTAACCAGCACAAACAGGCCAAACTCAAAGA

GATCAGCCTGTCTGCGGTGAGGTTCATGGAGGAGCTGGGAGAGGACCGGT

TTGGGAAAGTCTACAAAGGTCACCTGTTCGGCCCTGCCCCGGGGAGCAG

ACCCAGGCTGTGGCCATCAAAACGCTGAAGGACAAAGCGGAGGGGCCCCT

GCGGGAGGAGTTCCGGCATGAGGCTATGCTGCGAGCACGGCTGCAACACC

CCAACGTCGTCTGCCTGCTGGGCGTGGTGACCAAGGACCAGCCCCTGAGC

ATGATCTTCAGCTACTGTTCGCACGGCGACCTCCACGAATTCCTGGTCAT

GCGCTCGCCGCACTCGGACGTGGGCAGCACCGATGATGACCGCACGGTGA

AGTCCGCCCTGGAGCCCCCCGACTTCGTGCACCTTGTGGCACAGATCGCG

GCGGGGATGGAGTACCTATCCAGCCACCACGTGGTTCACAAGGACCTGGC

CACCCGCAATGTGCTAGTGTACGACAAGCTGAACGTGAAGATCTCAGACT

TGGGCCTCTTCCGAGAGGTGTATGCCGCCGATTACTACAAGCTGCTGGGG

AACTCGCTGCTGCCTATCCGCTGGATGGCCCCAGAGGCCATCATGTACGG

CAAGTTCTCCATCGACTCAGACATCTGGTCCTACGGTGTGGTCCTGTGGG

AGGTCTTCAGCTACGGCCTGCAGCCCTACTGCGGGTACTCCAACCAGGAT

GTGGTGGAGATGATCCGGAACCGGCAGGTGCTGCCTTGCCCCGATGACTG

-continued

```
TCCCGCCTGGGTGTATGCCCTCATGATCGAGTGCTGGAACGAGTTCCCCA

GCCGGCGGCCCCGCTTCAAGGACATCCACAGCCGGCTCCGAGCCTGGGGC

AACCTTTCCAACTACAACAGCTCGGCGCAGACCTCGGGGGCCAGCAACAC

CACGCAGACCAGCTCCCTGAGCACCAGCCCAGTGAGCAATGTGAGCAACG

CCCGCTACGTGGGGCCCAAGCAGAAGGCCCCGCCCTTCCCACAGCCCCAG

TTCATCCCCATGAAGGGCCAGATCAGACCCATGGTGCCCCGCCGCAGCT

CTACGTCCCCGTCAACGGCTACCAGCCGGTGCCGGCCTATGGGCCTACC

TGCCCAACTTCTACCCGGTGCAGATCCCAATGCAGATGGCCCCGCAGCAG

GTGCCTCCTCAGATGGTCCCCAAGCCCAGCTCACACCACAGTGGCAGTGG

CTCCACCAGCACAGGCTACGTCACCACGGCCCCCTCCAACACATCCATGG

CAGACAGGGCAGCCCTGCTCTCAGAGGGCGCTGATGACACACAGAACGCC

CCAGAAGATGGGGCCCAGAGCACCGTGCAGGAAGCAGAGGAGGAGGAGGA

AGGCTCTGTCCCAGAGACTGAGCTGCTGGGGGACTGTGACACTCTGCAGG

TGGACGAGGCCCAAGTCCAGCTGGAAGCTTGA
```

The polypeptide sequence of one embodiment of human ROR2 is provided herein as SEQ ID No. 225, as follows:

[SEQ ID No. 225]
```
MARGSALPRRPLLCIPAVWAAAALLLSVSRTSGEVEVLDPNDPLGPLDGQ

DGPIPTLKGYFLNFLEPVNNITIVQGQTAILHCKVAGNPPPNVRWLKNDA

PVVQEPRRIIIRKTEYGSRLRIQDLDTTDTGYYQCVATNGMKTITATGVL

FVRLGPTHSPNHNFQDDYHEDGFCQPYRGIACARFIGNRTIYVDSLQMQG

EIENRITAAFTMIGTSTHLSDQCSQFAIPSFCHFVFPLCDARSRTPKPRE

LCRDECEVLESDLCRQEYTIARSNPLILMRLQLPKCEALPMPESPDAANC

MRIGIPAERLGRYHQCYNGSGMDYRGTASTTKSGHQCQPWALQHPHSHHL

SSTDFPELGGGHAYCRNPGGQMEGPWCFTQNKNVRMELCDVPSCSPRDSS

KMGILYILVPSIAIPLVIACLFFLVCMCRNKQKASASTPQRRQLMASPSQ

DMEMPLINQHKQAKLKEISLSAVRFMEELGEDRFGKVYKGHLFGPAPGEQ

TQAVAIKTLKDKAEGPLREEFRHEAMLRARLQHPNVVCLLGVVTKDQPLS

MIFSYCSHGDLHEFLVMRSPHSDVGSTDDDRTVKSALEPPDFVHLVAQIA

AGMEYLSSHHVVHKDLATRNVLVYDKLNVKISDLGLFREVYAADYYKLLG

NSLLPIRWMAPEAIMYGKFSIDSDIWSYGVVLWEVFSYGLQPYCGYSNQD

VVEMIRNRQVLPCPDDCPAWVYALMIECWNEFPSRRPRFKDIHSRLRAWG

NLSNYNSSAQTSGASNTTQTSSLSTSPVSNVSNARYVGPKQKAPPFPQPQ

FIPMKGQIRPMVPPPQLYVPVNGYQPVPAYGAYLPNFYPVQIPMQMAPQQ

VPPQMVPKPSSHHSGSGSTSTGYVTTAPSNTSMADRAALLSEGADDTQNA

PEDGAQSTVQEAEEEEEGSVPETELLGDCDTLQVDEAQVQLEA
```

As described in the Examples, the inventors have created numerous embodiments of the antibody or functional fragment according to the first aspect of the invention. Indeed, as described in Example 1, the inventors have isolated a total of 199 antibodies, which are immunospecific for ROR2, 13 of which are most preferred, and which are described herein. These 13 preferred antibodies: (i) bind specifically to ROR2; (ii) have high ROR2-binding affinity; and (iii) form a pool that can be converted into full IgG molecules. All of the antibodies described herein can be developed for therapeutic and diagnostic uses.

Preferably, the antibody or functional fragment thereof corresponds to a clone selected from clone #016, #023, #024, #027, #084, #090, #093, #096, #121, #159, #173, #240 and #241. Sequence information about these 13 antibodies is provided in Example 2.

The inventors have determined that the amino acid sequence KTITATGVLFVRLGP, which is described herein as SEQ ID No. 228 (i.e. amino acids 109-123 of SEQ ID No.225) is an epitope for the antibody or functional fragment thereof according to the invention. This epitope can therefore be used to isolate or generate further antibodies according to the invention, as can other sub-fragments of the extracellular domain of ROR2. Other epitopes include TGYYQCVATNGMKTI, which is described herein as SEQ ID No. 226 (i.e. amino acids 97 to 111 of SEQ ID No. 233); RGIACARFIGNRTIY, which is described herein as SEQ ID No. 227 (i.e. amino acids 145 to 159 of SEQ ID No. 233); CQPYRGIACARFIGNRTIY, which is described herein as SEQ ID No. 229 (i.e. amino acids 141 to 159 of SEQ ID No. 233); QCSQFAIPSFCHFVFPLCD, which is described herein as SEQ ID No. 230 (i.e. amino acids 189 to 207 of SEQ ID No. 233); ELCRDECEVLESDLC, which is described herein as SEQ ID No. 231 (i.e. amino acids 217 to 231 of SEQ ID No. 233); and ANCMRIGIPAERLGR, which is described herein as SEQ ID No. 232 (i.e. amino acids 265 to 279 of SEQ ID No. 233). It will be appreciated that knowledge of these various epitopes can be used to generate novel ROR2-specific antibodies. These epitopes can also be located in the full length polypeptide sequence of SEQ ID No. 225.

Thus, in a second aspect, there is provided use of an epitope for generating an anti-Receptor Tyrosine Kinase-Like Orphan Receptor 2 (ROR2) antibody, or a functional fragment thereof, wherein the epitope comprises or consists of sequence selected from a group of epitopes consisting of TGYYQCVATNGMKTI (SEQ ID No. 226); RGIACARFIGNRTIY (SEQ ID No. 227); KTITATGVLFVRLGP (SEQ ID No. 228); CQPYRGIACARFIGNRTIY (SEQ ID No. 229); QCSQFAIPSFCHFVFPLCD (SEQ ID No. 230); ELCRDECEVLESDLC (SEQ ID No. 231); and ANCMRIGIPAERLGR (SEQ ID No. 232); and the rest of the sequence of the extracellular domain of ROR2 (i.e. SEQ ID No. 233); or a functional fragment or variant of any of these epitopes.

In one embodiment, the amino acid sequence of the extracellular domain of ROR2 is described herein as SEQ ID No. 233, as follows:

[SEQ ID No. 233]
```
EVEVLDPNDPLGPLDGQDGPIPTLKGYFLNFLEPVNNITIVQGQTAILHC

KVAGNPPPNVRWLKNDAPVVQEPRRIIIRKTEYGSRLRIQDLDTTDTGYY

QCVATNGMKTITATGVLFVRLGPTHSPNHNFQDDYHEDGFCQPYRGIACA

RFIGNRTIYVDSLQMQGEIENRITAAFTMIGTSTHLSDQCSQFAIPSFCH

FVFPLCDARSRTPKPRELCRDECEVLESDLCRQEYTIARSNPLILMRLQL

PKCEALPMPESPDAANCMRIGIPAERLGRYHQCYNGSGMDYRGTASTTKS

GHQCQPWALQHPHSHHLSSTDFPELGGGHAYCRNPGGQMEGPWCFTQNKN

VRMELCDVPSCSPRDSSKMG
```

The inventors have also determined the Complementarity Determining Regions (CDRs) of both the heavy and light chains of the ROR2-specific antibodies of the invention, and have found highly conserved motifs (see Tables 5 and 6—LCDR1, LCDR2 and LCDR3 being the three CDRs of the light chain, and HCDR1, HCDR2 and HCDR3 being the three CDRs of the heavy chain). Clearly, these conserved residues are important for defining the antibodies' binding specificity and affinity for the ROR2 protein, preferably the extracellular domain (ECD) thereof, and hence provide useful information for antibody engineering in order to modify and improve the binding profile of the antibody. The inventors have also determined the amino acid and DNA sequences of each of the variable region of each of the preferred 13 antibodies, which are described in Example 2.

CDRs Defined by Amino Acid Sequence

Thus, in one embodiment, the antibody or functional fragment thereof may comprise at least one antigen binding region comprising an amino acid sequence selected from a group consisting of:—(i) SEQ ID No. 1; (ii) SEQ ID No. 3; (iii) SEQ ID No. 5; (iv) SEQ ID No. 7; (v) SEQ ID No. 9; and (vi) SEQ ID No. 11. These six separate sequences correspond to the amino acid sequences of each of the CDRs of antibody clone #16.

In one embodiment, the antibody or functional fragment thereof may comprise at least one antigen binding region comprising an amino acid sequence selected from a group consisting of:—(i) SEQ ID No. 13; (ii) SEQ ID No. 15; (iii) SEQ ID No. 17; (iv) SEQ ID No. 19; (v) SEQ ID No. 21; and (vi) SEQ ID No. 23. These six separate sequences correspond to the amino acid sequences of each of the CDRs of antibody clone #23.

In one embodiment, the antibody or functional fragment thereof may comprise at least one antigen binding region comprising an amino acid sequence selected from a group consisting of:—(i) SEQ ID No. 25; (ii) SEQ ID No. 27; (iii) SEQ ID No. 29; (iv) SEQ ID No. 31; (v) SEQ ID No. 33; and (vi) SEQ ID No. 35. These six separate sequences correspond to the amino acid sequences of each of the CDRs of antibody clone #24.

In one embodiment, the antibody or functional fragment thereof may comprise at least one antigen binding region comprising an amino acid sequence selected from a group consisting of:—(i) SEQ ID No. 37; (ii) SEQ ID No. 39; (iii) SEQ ID No. 41; (iv) SEQ ID No. 43; (v) SEQ ID No. 45; and (vi) SEQ ID No. 47. These six separate sequences correspond to the amino acid sequences of each of the CDRs of antibody clone #27.

In one embodiment, the antibody or functional fragment thereof may comprise at least one antigen binding region comprising an amino acid sequence selected from a group consisting of:—(i) SEQ ID No. 49; (ii) SEQ ID No. 51; (iii) SEQ ID No. 53; (iv) SEQ ID No. 55; (v) SEQ ID No. 57, and (vi) SEQ ID No. 59. These six separate sequences correspond to the amino acid sequences of each of the CDRs of antibody clone #84.

In one embodiment, the antibody or functional fragment thereof may comprise at least one antigen binding region comprising an amino acid sequence selected from a group consisting of:—(i) SEQ ID No. 61; (ii) SEQ ID No. 63; (iii) SEQ ID No. 65; (iv) SEQ ID No. 67; (v) SEQ ID No. 69; and (vi) SEQ ID No. 71. These six separate sequences correspond to the amino acid sequences of each of the CDRs of antibody clone #90.

In one embodiment, the antibody or functional fragment thereof may comprise at least one antigen binding region comprising an amino acid sequence selected from a group consisting of:—(i) SEQ ID No. 73; (ii) SEQ ID No. 75; (iii) SEQ ID No. 77; (iv) SEQ ID No. 79; (v) SEQ ID No. 81; and (vi) SEQ ID No. 83. These six separate sequences correspond to the amino acid sequences of each of the CDRs of antibody clone #93.

In one embodiment, the antibody or functional fragment thereof may comprise at least one antigen binding region comprising an amino acid sequence selected from a group consisting of:—(i) SEQ ID No. 85; (ii) SEQ ID No. 87; (iii) SEQ ID No. 89; (iv) SEQ ID No. 91; (v) SEQ ID No. 93; and (vi) SEQ ID No. 95. These six separate sequences correspond to the amino acid sequences of each of the CDRs of antibody clone #96.

In one embodiment, the antibody or functional fragment thereof may comprise at least one antigen binding region comprising an amino acid sequence selected from a group consisting of:—(i) SEQ ID No. 97; (ii) SEQ ID No. 99; (iii) SEQ ID No. 101; (iv) SEQ ID No. 103; (v) SEQ ID No. 105; and (vi) SEQ ID No. 107. These six separate sequences correspond to the amino acid sequences of each of the CDRs of antibody clone #121.

In one embodiment, the antibody or functional fragment thereof may comprise at least one antigen binding region comprising an amino acid sequence selected from a group consisting of:—(i) SEQ ID No. 109; (ii) SEQ ID No. 111; (iii) SEQ ID No. 113; (iv) SEQ ID No. 115; (v) SEQ ID No. 117; and (vi) SEQ ID No. 119. These six separate sequences correspond to the amino acid sequences of each of the CDRs of antibody clone #159.

In one embodiment, the antibody or functional fragment thereof may comprise at least one antigen binding region comprising an amino acid sequence selected from a group consisting of:—(i) SEQ ID No. 121; (ii) SEQ ID No. 123; (iii) SEQ ID No. 125; (iv) SEQ ID No. 127; (v) SEQ ID No. 129; and (vi) SEQ ID No. 131. These six separate sequences correspond to the amino acid sequences of each of the CDRs of antibody clone #173.

In one embodiment, the antibody or functional fragment thereof may comprise at least one antigen binding region comprising an amino acid sequence selected from a group consisting of:—(i) SEQ ID No. 133; (ii) SEQ ID No. 135; (iii) SEQ ID No. 137; (iv) SEQ ID No. 139; (v) SEQ ID No. 141; and (vi) SEQ ID No. 143. These six separate sequences correspond to the amino acid sequences of each of the CDRs of antibody clone #240.

In one embodiment, the antibody or functional fragment thereof may comprise at least one antigen binding region comprising an amino acid sequence selected from a group consisting of:—(i) SEQ ID No. 145; (ii) SEQ ID No. 147; (iii) SEQ ID No. 149; (iv) SEQ ID No. 151; (v) SEQ ID No. 153; and (vi) SEQ ID No. 155. These six separate sequences correspond to the amino acid sequences of each of the CDRs of antibody clone #241.

CDRs Defined by DNA Sequence

In one embodiment, the antibody or functional fragment thereof may comprise at least one antigen binding region encoded by a nucleic acid comprising a nucleotide sequence selected from a group consisting of:—(i) SEQ ID No. 2; (ii) SEQ ID No. 4; (iii) SEQ ID No. 6; (iv) SEQ ID No. 8; (v) SEQ ID No. 10; and (vi) SEQ ID No. 12. These six separate sequences correspond to the nucleotide sequences encoding each of the CDRs of antibody clone #16.

In one embodiment, the antibody or functional fragment thereof may comprise at least one antigen binding region encoded by a nucleic acid comprising a nucleotide sequence selected from a group consisting of:—(i) SEQ ID No. 14; (ii) SEQ ID No. 16; (iii) SEQ ID No. 18; (iv) SEQ ID No. 20;

(v) SEQ ID No. 22; and (vi) SEQ ID No. 24. These six separate sequences correspond to the nucleotide sequences encoding each of the CDRs of antibody clone #23.

In one embodiment, the antibody or functional fragment thereof may comprise at least one antigen binding region encoded by a nucleic acid comprising a nucleotide sequence selected from a group consisting of:—(i) SEQ ID No. 26; (ii) SEQ ID No. 28; (iii) SEQ ID No. 30; (iv) SEQ ID No. 32; (v) SEQ ID No. 34; and (vi) SEQ ID No. 36. These six separate sequences correspond to the nucleotide sequences encoding each of the CDRs of antibody clone #24.

In one embodiment, the antibody or functional fragment thereof may comprise at least one antigen binding region encoded by a nucleic acid comprising a nucleotide sequence selected from a group consisting of:—(i) SEQ ID No. 38; (ii) SEQ ID No. 40; (iii) SEQ ID No. 42; (iv) SEQ ID No. 44; (v) SEQ ID No. 46; and (vi) SEQ ID No. 48. These six separate sequences correspond to the nucleotide sequences encoding each of the CDRs of antibody clone #27.

In one embodiment, the antibody or functional fragment thereof may comprise at least one antigen binding region encoded by a nucleic acid comprising a nucleotide sequence selected from a group consisting of:—(i) SEQ ID No. 50; (ii) SEQ ID No. 52; (iii) SEQ ID No. 54; (iv) SEQ ID No. 56; (v) SEQ ID No. 58; and (vi) SEQ ID No. 60. These six separate sequences correspond to the nucleotide sequences encoding each of the CDRs of antibody clone #84.

In one embodiment, the antibody or functional fragment thereof may comprise at least one antigen binding region encoded by a nucleic acid comprising a nucleotide sequence selected from a group consisting of:—(i) SEQ ID No. 62; (ii) SEQ ID No. 64; (iii) SEQ ID No. 66; (iv) SEQ ID No. 68; (v) SEQ ID No. 70; and (vi) SEQ ID No. 72. These six separate sequences correspond to the nucleotide sequences encoding each of the CDRs of antibody clone #90.

In one embodiment, the antibody or functional fragment thereof may comprise at least one antigen binding region encoded by a nucleic acid comprising a nucleotide sequence selected from a group consisting of:—(i) SEQ ID No. 74; (ii) SEQ ID No. 76; (iii) SEQ ID No. 78; (iv) SEQ ID No. 80; (v) SEQ ID No. 82; and (vi) SEQ ID No. 84. These six separate sequences correspond to the nucleotide sequences encoding each of the CDRs of antibody clone #93.

In one embodiment, the antibody or functional fragment thereof may comprise at least one antigen binding region encoded by a nucleic acid comprising a nucleotide sequence selected from a group consisting of:—(i) SEQ ID No. 86; (ii) SEQ ID No. 88; (iii) SEQ ID No. 90; (iv) SEQ ID No. 92; (v) SEQ ID No. 94; and (vi) SEQ ID No. 96. These six separate sequences correspond to the nucleotide sequences encoding each of the CDRs of antibody clone #96.

In one embodiment, the antibody or functional fragment thereof may comprise at least one antigen binding region encoded by a nucleic acid comprising a nucleotide sequence selected from a group consisting of:—(i) SEQ ID No. 98; (ii) SEQ ID No. 100; (iii) SEQ ID No. 102; (iv) SEQ ID No. 104; (v) SEQ ID No. 106; and (vi) SEQ ID No. 108. These six separate sequences correspond to the nucleotide sequences encoding each of the CDRs of antibody clone #121.

In one embodiment, the antibody or functional fragment thereof may comprise at least one antigen binding region encoded by a nucleic acid comprising a nucleotide sequence selected from a group consisting of:—(i) SEQ ID No. 110; (ii) SEQ ID No. 112; (iii) SEQ ID No. 114; (iv) SEQ ID No. 116; (v) SEQ ID No. 118; and (vi) SEQ ID No. 120. These six separate sequences correspond to the nucleotide sequences encoding each of the CDRs of antibody clone #159.

In one embodiment, the antibody or functional fragment thereof may comprise at least one antigen binding region encoded by a nucleic acid comprising a nucleotide sequence selected from a group consisting of:—(i) SEQ ID No. 122; (ii) SEQ ID No. 124; (iii) SEQ ID No. 126; (iv) SEQ ID No. 128; (v) SEQ ID No. 130; and (vi) SEQ ID No. 132. These six separate sequences correspond to the nucleotide sequences encoding each of the CDRs of antibody clone #173.

In one embodiment, the antibody or functional fragment thereof may comprise at least one antigen binding region encoded by a nucleic acid comprising a nucleotide sequence selected from a group consisting of:—(i) SEQ ID No. 134; (ii) SEQ ID No. 136; (iii) SEQ ID No. 138; (iv) SEQ ID No. 140; (v) SEQ ID No. 142; and (vi) SEQ ID No. 144. These six separate sequences correspond to the nucleotide sequences encoding each of the CDRs of antibody clone #240.

In one embodiment, the antibody or functional fragment thereof may comprise at least one antigen binding region encoded by a nucleic acid comprising a nucleotide sequence selected from a group consisting of:—(i) SEQ ID No. 146; (ii) SEQ ID No. 148; (iii) SEQ ID No. 150; (iv) SEQ ID No. 152; (v) SEQ ID No. 154; and (vi) SEQ ID No. 156. These six separate sequences correspond to the nucleotide sequences encoding each of the CDRs of antibody clone #241.

It will be appreciated that the antigen binding region comprises a Complementarity Determining Region (CDR) of the antibody, or functional fragment thereof, and that mutations may reside in framework regions between the CDRs of the antibody or functional fragment thereof. The recombinant immunoglobulin may comprise any, or all, of the antigen binding regions described herein for each embodiment be that defined by its amino acid sequence or its encoding nucleic acid sequence. The recombinant immunoglobulin may comprise an antigen binding site with which the antigen binds, preferably eliciting an immunological response. Preferably, the at least one antigen binding region forms at least part of the antigen binding site. The antibody or functional fragment thereof may comprise at least two, suitably at least three, and more suitably at least four antigen binding regions defined in the first aspect. Preferably, the antibody or functional fragment comprises at least five, and more preferably all six antigen binding regions. The antibody or fragment thereof may therefore comprise at least one, two, three, four, five or six amino acid sequences defined in (i) to (vi) in any embodiment of antibody described herein. Preferably, however, the antibody or fragment thereof comprises all of (i) to (vi) in any embodiment described herein.

In one embodiment of the antibody or a functional fragment thereof, the polypeptide sequence of the variable region of the light chain may comprise an amino acid sequence substantially as set out in SEQ ID Nos: 158, 162, 166, 170, 174, 178, 182, 186, 190, 194, 198, 202 or 206, or a functional variant or fragment thereof.

In one embodiment of the antibody or a functional fragment thereof, the polypeptide sequence of the variable region of the heavy chain may comprise an amino acid sequence substantially as set out in SEQ ID Nos: 160, 164, 168, 172, 176, 180, 184, 188, 192, 196, 200, 204 or 208, or a functional variant or fragment thereof.

The antibody or functional fragment thereof may comprise a light chain variable region (VL) and/or a heavy chain variable region (VH), the light chain variable region comprising an amino acid sequence which is substantially as set out in SEQ ID Nos: 158, 162, 166, 170, 174, 178, 182, 186, 190, 194, 198, 202 or 206, or a functional fragment or variant thereof, and the heavy chain variable region comprising the amino acid sequence which is substantially as set out in SEQ ID Nos: 160, 164, 168, 172, 176, 180, 184, 188, 192, 196, 200, 204 or 208, or a functional fragment or variant thereof.

In one embodiment of the antibody or a functional fragment thereof, the DNA sequence of the variable region of the light chain may comprise a nucleotide sequence substantially as set out in SEQ ID No: 157, 161, 165, 169, 173, 177, 181, 185, 189, 193, 197, 201 or 205, or a functional variant or fragment thereof.

In one embodiment of the antibody or a functional fragment thereof, the DNA sequence of the variable region of the heavy chain may comprise a nucleotide sequence substantially as set out in SEQ ID No: 159, 163, 167, 171, 175, 179, 183, 187, 191, 195, 199, 203 or 207, or a functional variant or fragment thereof.

The antibody or functional fragment thereof may comprise a light chain variable region (VL) and/or a heavy chain variable region (VH), the light chain variable region being encoded by a polynucleotide comprising a nucleotide sequence which is substantially as set out in SEQ ID. Nos. 157, 161, 165, 169, 173, 177, 181, 185, 189, 193, 197, 201 or 205, or a functional fragment or variant thereof, the heavy chain variable region being encoded by a polynucleotide comprising a nucleotide sequence which is substantially as set out in SEQ ID No: 159, 163, 167, 171, 175, 179, 183, 187, 191, 195, 199, 203 or 207, or a functional fragment or variant thereof.

The polypeptide sequence of the constant region of the light chain of one embodiment of the antibody of the invention may comprise or consist of an amino acid sequence which is substantially as set out in either SEQ ID No. 209 or SEQ ID No. 211, or a functional fragment or variant thereof. The polypeptide sequence of the constant region of the heavy chain of one embodiment of the antibody of the invention may comprise or consist of an amino acid sequence which is substantially as set out in SEQ ID No. 213, or a functional fragment or variant thereof.

The DNA sequence encoding the constant region of the light chain of one embodiment of the antibody of the invention may comprise or consist of a nucleotide sequence which is substantially as set out in either SEQ ID No. 210 or SEQ ID No. 212, or a functional fragment or variant thereof. The DNA sequence encoding the constant region of the heavy chain of one embodiment of the antibody of the invention may comprise or consist of a nucleotide sequence which is substantially as set out in SEQ ID No. 214, or a functional fragment or variant thereof.

According to a third aspect, there is provided an isolated peptide capable of binding to Receptor Tyrosine Kinase-Like Orphan Receptor 2 (ROR2) protein, the peptide comprising or consisting of an amino acid sequence selected from a group consisting of:—
  (i) SEQ ID No:1, 3, 5, 7, 9 and/or 11 (the CDRs of ab clone #16);
  (ii) SEQ ID No:13, 15, 17, 19, 21 and/or 23 (the CDRs of ab clone #23);
  (iii) SEQ ID No:25, 27, 29, 31, 33 and/or 35 (the CDRs of ab clone #24);
  (iv) SEQ ID No:37, 39, 41, 43, 45 and/or 47 (the CDRs of ab clone #27);
  (v) SEQ ID No:49, 51, 53, 55, 57 and/or 59 (the CDRs of ab clone #84);
  (vi) SEQ ID No:61, 63, 65, 67, 69 and/or 71 (the CDRs of ab clone #90);
  (vii) SEQ ID No:73, 75, 77, 79, 81 and/or 83 (the CDRs of ab clone #93);
  (viii) SEQ ID No:85, 87, 89, 91, 93 and/or 95 (the CDRs of ab clone #96);
  (ix) SEQ ID No:97, 99, 101, 103, 105 and/or 107 (the CDRs of ab clone #121);
  (x) SEQ ID No:109, 111, 113, 115, 117 and/or 119 (the CDRs of ab clone #159);
  (xi) SEQ ID No:121, 123, 125, 127, 129 and/or 131 (the CDRs of ab clone #173);
  (xii) SEQ ID No:133, 135, 137, 139, 141 and/or 143 (the CDRs of ab clone #240); and/or
  (xiii) SEQ ID No:145, 147, 149, 151, 153 and/or 155 (the CDRs of ab done #241).

The peptide of the third aspect is preferably capable of binding to an extracellular domain of ROR2 protein. Thus, the isolated peptide of the third aspect may be an anti-Receptor Tyrosine Kinase-Like Orphan Receptor 2 (ROR2) antibody, or a functional fragment thereof. The antibody may or may not be human. For example, the antibody or fragment thereof may be murine. It may also be recombinant. It will be appreciated that the amino acid sequences defined in each of (i) to (xiii) of the third aspect are the CDRs of the antibody or a functional fragment thereof of the first aspect. The isolated peptide may therefore comprise or consist of at least two, three, four, five or six amino acid sequences defined in any of (i) to (xiii). Preferably, the peptide comprises or consists of all of the amino acid sequences defined in any of (i) to (xiii).

The peptide may comprise or consist of an amino acid sequence substantially as set out in SEQ ID No: 158, 162, 166, 170, 174, 178, 182, 186, 190, 194, 198, 202 or 206, or a functional variant or fragment thereof. The peptide may comprise or consist of an amino acid sequence substantially as set out in SEQ ID No: 160, 164, 168, 172, 176, 180, 184, 188, 192, 196, 200, 204 or 208, or a functional variant or fragment thereof.

The peptide may comprise or consist of an amino acid sequence which is substantially as set out in SEQ ID No: 209, 211 or 213, or a functional variant or fragment thereof.

While the various peptides described herein may be shown with no protecting groups, in certain embodiments they can bear one, two, three, four, or more protecting groups. In various embodiments, the protecting groups can be coupled to the C and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus. Examples of such protected peptides include acetyl, amide, 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethylbenzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-di-axocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Born), t-butoxycarbonyl (Boc), cyclohexyloxy (cHxO), t-butoxymethyl (Burn), t-butoxy (tBuO), t-Butyl (tBu), Trifluoroacetyl (TFA) or combinations thereof. The protecting group can be can be eliminated and/or substituted with another protecting group as described herein.

Without being bound by a particular theory, it was discovered that addition of a protecting group, particularly to the carboxyl and in certain embodiments the amino terminus can improve the stability and efficacy of the peptide.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propionyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g., groups having the formula: CH3-(CH2)n-CO— where n ranges from about 1 to about 20, preferably from about 1 to about 16 or 18, more preferably from about 3 to about 13, and most preferably from about 3 to about 10.

In certain embodiments, the protecting groups include, but are not limited to alkyl chains as in fatty acids, propionyl, formyl, and others. Particularly preferred carboxyl protecting groups include amides, esters, and ether-forming protecting groups. In one embodiment, an acetyl group is used to protect the amino terminus and/or an amino group is used to protect the carboxyl terminus (i.e., amidated carboxyl terminus). In certain embodiments blocking groups include alkyl groups of various lengths, e.g., groups having the formula: CH3-(CH2)n-CO— where n ranges from about 3 to about 20, preferably from about 3 to about 16, more preferably from about 3 to about 13, and most preferably from about 3 to about 10.

In certain embodiments, the acid group on the C-terminal can be blocked with an alcohol, aldehyde or ketone group and/or the N-terminal residue can have the natural amide group, or be blocked with an acyl, carboxylic acid, alcohol, aldehyde, or ketone group.

Other protecting groups include, but are not limited to Fmoc, tbutoxycarbonyl (t-BOC), 9-fluoreneacetyl group, 1-fluorenecarboxylic group, 9-florenecarboxylic group, 9-fluorenone-1-carboxylic group, benzyloxycarbonyl, xanthyl(Xan), trityl (Trt), 4-methyltrityl (Mtt), 4-methoxytrityl (Mrnt), 4-methoxy-2,3,6-trimethylbenzenesulphonyl (Mtr), Mesitylene-2-sulphonyl (Mts), 4,4-dimethoxybenzhydryl (Mbh), Tosyl (Tos), 2,2,5,7,8-pentamethyl chrornan-6-sulphonyl (Prnc), 4-methylbenzyl(M), 4-ethylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Born), cyclohexyloxy (cHxO), tbutoxyrnethyl (Burn), t-butoxy (tBuO), t-Butyl (tBu), Acetyl (Ac), and Trifluoroacetyl(TFA). Protecting/blocking groups are well known to those of skill as are methods of coupling such groups to the appropriate residue(s) comprising the peptides of this invention (see, e.g., Greene et al., (1991) *Protective Groups in Organic Synthesis,* 2nd ed., John Wiley & Sons, Inc. Somerset, N.J.).

According to a fourth aspect, there is provided an isolated nucleic acid encoding a peptide capable of binding to Receptor Tyrosine Kinase-Like Orphan Receptor 2 (ROR2) protein, the nucleic acid comprising or consisting of a nucleotide sequence selected from a group consisting of:—

(i) SEQ ID No:2, 4, 6, 8, 10 and/or 12 (the CDRs of ab clone #16);
(ii) SEQ ID No:14, 16, 18, 20, 22 and/or 24 (the CDRs of ab clone #23);
(iii) SEQ ID No:26, 28, 30, 32, 34 and/or 36 (the CDRs of ab clone #24);
(iv) SEQ ID No:38, 40, 42, 44, 46 and/or 48 (the CDRs of ab clone #27);
(v) SEQ ID No:50, 52, 54, 56, 58 and/or 60 (the CDRs of ab clone #84);
(vi) SEQ ID No:62, 64, 66, 68, 70 and/or 72 (the CDRs of ab clone #90);
(vii) SEQ ID No:74, 76, 78, 80, 82 and/or 84 (the CDRs of ab clone #93);
(viii) SEQ ID No:86, 88, 90, 92, 94 and/or 96 (the CDRs of ab clone #96);
(ix) SEQ ID No:98, 100, 102, 104, 106 and/or 108 (the CDRs of ab clone #121);
(x) SEQ ID No:110, 112, 114, 116, 118 and/or 120 (the CDRs of ab clone #159);
(xi) SEQ ID No:122, 124, 126, 128, 130 and/or 132 (the CDRs of ab clone #173);
(xii) SEQ ID No:134, 136, 138, 140, 142 and/or 144 (the CDRs of ab clone #240); and/or
(xiii) SEQ ID No:146, 148, 150, 152, 154 and/or 156 (the CDRs of ab clone #241).

Preferably, the nucleic acid may encode an anti-Receptor Tyrosine Kinase-Like Orphan Receptor 1 (ROR2) antibody, or a functional fragment thereof. The antibody may or may not be human. For example, the antibody may be murine. It may also be recombinant. It will be appreciated that the nucleotide sequences defined in each of (i) to (xiv) of the fourth aspect encode the CDRs of the antibody or a functional fragment thereof of the first aspect. Thus, the nucleic acid may comprise or consist of at least two, three, four, five or six nucleotide sequences defined in any of (i) to (xiii). Preferably, the nucleic acid comprises or consist of all of the nucleotide sequences defined in any of (i) to (vi). Preferably, the nucleic acid comprises a nucleotide sequence substantially encoding an amino acid sequence of at least one antigen binding region of the human antibody, or functional fragment thereof.

The nucleic acid may comprise or consists of a nucleotide sequence substantially as set out in SEQ ID No: 157, 161, 165, 169, 173, 177, 181, 185, 189, 193, 197, 201 or 205, or a functional variant or fragment thereof. The nucleic acid may comprise or consist of a nucleotide sequence substantially as set out in 159, 163, 167, 171, 175, 179, 183, 187, 191, 195, 199, 203 or 207, or a functional variant or fragment thereof.

The nucleic acid may comprise or consist of a nucleotide sequence which is substantially as set out in SEQ ID No: 210, 212 or 214, or a functional fragment or variant thereof.

The inventors have also discovered that some of the ROR2 antibodies according to the invention also bind to ROR1. Each of these dual binding antibodies is capable of binding to distinct epitopes found on both the ROR1 and the ROR2 protein with surprisingly high affinity. Antibody clones that exhibit dual specificity (i.e. bind to ROR1 and ROR2; see FIG. 5, Table 3) should have utility for tumours that co-express these antigens (e.g. Neuroblastoma and small cell lung cancer), or tumors with mixed clones, i.e. clones that carry ROR1 and clones that carry ROR2. Therefore, in another embodiment of the invention, the antibody, or functional fragment thereof may also be capable of binding to Receptor Tyrosine Kinase-Like Orphan Receptor 1 (ROR1).

The term "ROR1" can refer to family 1 of the receptor tyrosine kinase-like orphan receptors (mRNA: NM_005012.2, protein: NP_005003.2). The DNA sequence encoding one embodiment of human ROR1 is provided herein as SEQ ID No. 222, as follows:

[SEQ ID No. 222]
atgcaccggccgcgccgccgcgggacgcgcccgccgctcctggcgctgct ggccgcgctgctgctggccgcacgcggggctgctgcccaagaaacagagc tgtcagtcagtgctgaattagtgcctacctcatcatggaacatctcaagt gaactcaacaaagattcttacctgaccctcgatgaaccaatgaataacat caccacgtctctgggccagacagcagaactgcactgcaaagtctctggga atccacctccaccatccgctggttcaaaaatgatgctcctgtggtccag gagccccggaggctctcctttcggtccaccatctatggctctcggctgcg gattagaaacctcgacaccacagacacaggctacttccagtgcgtggcaa caaacggcaaggaggtggtttcttccactggagtcttgtttgtcaagttt ggccccctcccactgcaagtccaggatactcagatgagtatgaagaaga tggattctgtcagccatacagagggattgcatgtgcaagatttattggca accgcaccgtctatatggagtctttgcacatgcaaggggaaatagaaaat cagatcacagctgccttcactatgattggcacttccagtcacttatctga taagtgttctcagttcgccattccttccctgtgccactatgccttcccgt actgcgatgaaacttcatccgtcccaaagcccgtgacttgtgtcgcgat gaatgtgaaatcctggagaatgtcctgtgtcaaacagagtacatttttgc aagatcaaatcccatgattctgatgaggctgaaactgccaaactgtgaag atctccccagccagagagcccagaagctgcgaactgtatccggattgga attcccatggcagatcctataaataaaaatcacaagtgttataacagcac aggtgtggactaccggggaccgtcagtgtgaccaaatcagggcgccagt gccagccatggaattcccagtatcccacacacacactttcaccgcccttt cgtttcccagagctgaatggaggccattcctactgccgcaacccagggaa tcaaaaggaagctcccctggtgcttcaccttggatgaaaactttaagtctg atctgtgtgacatcccagcgtgcgattcaaaggattccaaggagaagaat aaaatggaaatcctgtacatactagtgccaagtgtggccattcccctggc cattgctttactcttcttcatttgcgtctgtcggaataaccagaagt catcgtcggcaccagtccagaggcaaccaaaaacacgtcagaggtcaaaat gtagagatgtcaatgctgaatgcatataaacccaagagcaaggctaaga gctacctctttctgctgtacgcttatggaagaattgggtgagtgtgcct ttggaaaaatctataaaggccatctctatctcccaggcatggaccatgct cagctggttgctatcaagaccttgaaagactataacaaccccccagcaatg gacggaatttcaacaagaagcctccctaatggcagaactgcaccaccca atattgtctgccttctaggtgccgtcactcaggaacaacctgtgtgcatg cttttgagtatattaatcaggggatctccatgagttcctcatcatgag atccccacactctgatgttggctgcagcagtgatgaagatgggactgtga aatccagcctggaccacggagattttctgcacattgcaattcagattgca gctggcatggaatacctgtctagtcacttctttgtccacaaggaccttgc agctcgcaatatttttaatcggagagcaacttcatgtaaagatttcagact tggggctttccagagaaatttactccgctgattactacagggtccagagt aagtccttgctgcccattcgctggatgccccctgaagccatcatgtatgg caaattctcttctgattcagatatctggtcctttggggttgtcttgtggg agattttcagttttggactccagccatattatggattcagtaaccaggaa gtgattgagatggtgagaaaacgggcagctcttaccatgctctgaagactg cccacccagaatgtacagcctcatgacagagtgctggaatgagattcctt ctaggagaccaagatttaaagatattcacgtccggcttcggtcctgggag ggactctcaagtcacacaagctctactactccttcaggggggaaatgccac cacacagacaacctccctcagtgccagcccagtgagtaatctcagtaacc ccagatatcctaattacatgttcccgagccagggtattacaccacagggc cagattgctggttcattggcccgccaatacctcagaaccagcgattcat tcccatcaatggatacccaatacctcctggatatgcagcgtttccagctg cccactaccagccaacaggtcctcccagagtgattcagcactgcccacct cccaagagtcggtccccaagcagtgccagtgggtcgactagcactggcca tgtgactagcttgccctcatcaggatccaatcaggaagcaaatattcctt tactaccacacatgtcaattccaaatcatcctggtggaatgggtatcacc gtttttggcaacaaatctcaaaaaccctacaaaattgactcaaagcaagc atctttactaggagacgccaatattcatggacacaccgaatctatgattt ctgcagaactgtaa The polypeptide sequence of one embodiment of human ROR1 is provided herein as SEQ ID No. 223, as follows:

[SEQ ID No. 223]
MHRPRRRGTRPPLLALLAALLLAARGAAAQETELSVSAELVPTSSWNISS

ELNKDSYLTLDEPMNNITTSLGQTAELHCKVSGNPPPTIRWFKNDAPVVQ

EPRRLSFRSTIYGSRLRIRNLDTTDTGYFQCVATNGKEVVSSTGVLFVKF

GPPPTASPGYSDEYEEDGFCQPYRGIACARFIGNRTVYMESLHMQGEIEN

QITAAFTMIGTSSHLSDKCSQFAIPSLCHYAFPYCDETSSVPKPRDLCRD

ECEILENVLCQTEYIFARSNPMILMRLKLPNCEDLPQPESPEAANCIRIG

IPMADPINKNHKCYNSTGVDYRGTVSVTKSGRQCQPWNSQYPHTHTFTAL

RFPELNGGHSYCRNPGNQKEAPWCFTLDENFKSDLCDIPACDSKDSKEKN

KMEILYILVPSVAIPLAIALLFFFICVCRNNQKSSSAPVQRQPKHVRGQN

VEMSMLNAYKPKSKAKELPLSAVRFMEELGECAFGKIYKGHLYLPGMDHA

QLVAIKTLKDYNNPQQWTEFQQEASLMAELHHPNIVCLLGAVTQEQPVCM

-continued

```
LFEYINQGDLHEFLIMRSPHSDVGCSSDEDGTVKSSLDHGDFLHIAIQIA

AGMEYLSSHFFVHKDLAARNILIGEQLHVKISDLGLSREIYSADYYRVQS

KSLLPIRWMPPEAIMYGKFSSDSDIWSFGVVLWEIFSFGLQPYYGFSNQE

VIEMVRKRQLLPCSEDCPPRMYSLMTECWNEIPSRRPRFKDIHVRLRSWE

GLSSHTSSTTPSGGNATTQTTSLSASPVSNLSNPRYPNYMFPSQGITPQG

QIAGFIGPPIPQNQRFIPINGYPIPPGYAAFPAAHYQPTGPPRVIQHCPP

PKSRSPSSASGSTSTGHVTSLPSSGSNQEANIPLLPHMSIPNHPGGMGIT

VFGNKSQKPYKIDSKQASLLGDANIHGHTESMISAEL*
```

As described in Example 1, the inventors have identified 199 antibody clones. 37 of these antibody clones have been identified as being capable of binging to both ROR1 and ROR2. Four of these 37 antibody clones are most preferred, and are described herein as antibody clone #016, #084, #121 and #159. Preferably, therefore the antibody or functional fragment thereof corresponds to a clone selected from clone #016, #084, #121, and #159.

The amino acid sequence of the CDRs for clone #16 are preferably SEQ ID No:1, 3, 5, 7, 9 and/or 11. The nucleotide sequence encoding the clone #16 CDRs are preferably SEQ ID No:2, 4, 6, 8, 10 and/or 12.

The amino acid sequence of the CDRs for clone #84 are preferably SEQ ID No:49, 51, 53, 55, 57 and/or 59. The nucleotide sequence encoding the clone #84 CDRs are preferably SEQ ID No:50, 52, 54, 56, 58 and/or 60.

The amino acid sequence of the CDRs for clone #121 are preferably SEQ ID No:97, 99, 101, 103, 105 and/or 107. The nucleotide sequence encoding the clone #121 CDRs are preferably SEQ ID No:98, 100, 102, 104, 106 and/or 108.

The amino acid sequence of the CDRs for clone #159 are preferably SEQ ID No:109, 111, 113, 115, 117 and/or 119. The nucleotide sequence encoding the clone #159 CDRs are preferably SEQ ID No:110, 112, 114, 116, 118 and/or 120.

These four preferred dual binding ROR1/ROR2 antibodies: (i) bind specifically to ROR1 and ROR2; (ii) have high ROR1- and ROR2-binding affinity; and (iii) form a pool that can be converted into full IgG molecules. All of the antibodies described herein can be developed for therapeutic and diagnostic uses.

Advantageously, the antibody or functional fragment thereof, according to the first aspect of the invention, has utility of a therapeutic agent in its own right, and is a significant improvement on therapies which use antibodies comprising a non-human region (e.g. murine), Fc fragment (i.e. framework regions), or at least one murine antigen binding region or Complementarity Determining Region (CDR). However, in addition, technologies to maximize drug efficacy have been evaluated, including glycosylation engineering to enhance the ADCC (Antibody-Dependent Cell-Mediated Cytotoxicity) and/or CDC (Complement-Dependent Cytotoxicity) activity of the antibody or functional fragment thereof, conjugation to a cytotoxic moiety, such as radiation, a cytotoxic drug or toxin, and generation of a bispecific antibody with one arm targeting a tumour cell, and the other arm attracting cytotoxic T cells.

Thus, in a fifth aspect, there is provided an antibody-drug conjugate (ADC) comprising the antibody or a functional fragment thereof of the first aspect, and a cytotoxic moiety.

Antibody-drug conjugates (ADC) can be used to deliver a potent cytotoxic drug selectively to a target cell via an antibody. Such methods, when applied to a tumour antigen target, can enhance the anti-tumour activity of antibodies and improve the tumour-to-normal tissue selectivity of chemotherapy. One key parameter for ADC development is that the antibody may be capable of being endocytosed upon binding to the target antigen, such as ROR2. Therefore, endocytosed antibody may deliver the conjugated drug into target cancer cells.

In some embodiments, ADCs may comprise antibodies or fragments thereof comprising or consisting of the sequences selected from the group consisting of (i) SEQ ID No:1, 3, 5, 7, 9 and/or 11; (ii) SEQ ID No:13, 15, 17, 19, 21 and/or 23; (iii) SEQ ID No:25, 27, 29, 31, 33 and/or 35; (iv) SEQ ID No:37, 39, 41, 43, 45 and/or 47, (v) SEQ ID No:49, 51, 53, 55, 57 and/or 59; (vi) SEQ ID No:61, 63, 65, 67, 69 and/or 71; (vii) SEQ ID No:73, 75, 77, 79, 81 and/or 83; (viii) SEQ ID No:85, 87, 89, 91, 93 and/or 95; (ix) SEQ ID No:97, 99, 101, 103, 105 and/or 107; (x) SEQ ID No:109, 111, 113, 115, 117 and/or 119; (xi) SEQ ID No:121, 123, 125, 127, 129 and/or 131; (xii) SEQ ID No:133, 135, 137, 139, 141 and/or 143; and/or (xiii) SEQ ID No:145, 147, 149, 151, 153 and/or 155, conjugated to a therapeutic agent (such as a cytotoxic agent).

The cytotoxic moiety may be a toxin, such as monomethyl auristatin E (MMAE), monomethyl auristatin F (MMAF) or maytansine. The drug moiety may be an alpha-emitting radionucleotide, such as a 225Ac label. These toxins can be linked to the antibody or functional fragment thereof (i.e. an antigen-binding fragment thereof) via a cleavable linker, such as a disulfide bond, a hydrazone linker or a peptide linker, or via a non-cleavable linkers, such as a thioether bond using a SMCC (N-succinimidyl-4-(N-maleimidomethyl)-cyclohexane-1-carboxylate) linker.

According to a sixth aspect, there is provided an antibody or a functional fragment thereof as defined in the first aspect, a peptide as defined in the third aspect, a nucleic acid as defined in the fourth aspect, or an antibody-drug conjugate as defined in the fifth aspect, each being optionally derivatised, for use in therapy or in diagnosis.

The antibody or functional fragment thereof as defined in the first aspect, the peptide as defined in the third aspect, the nucleic acid as defined in the fourth aspect, or the antibody-drug conjugate as defined in the fifth aspect, may be used as a medicament, which is preferably adapted for use in the treatment, amelioration or prevention of cancer.

Therefore, according to a seventh aspect, there is provided an antibody or a functional fragment thereof as defined in the first aspect, a peptide as defined in the third aspect, a nucleic acid as defined in the fourth aspect, or an antibody-drug conjugate as defined in the fifth aspect, each being optionally derivatised, for use in treating, preventing or ameliorating cancer.

According to an eighth aspect, there is provided a method of treating, preventing or ameliorating cancer in a subject, the method comprising administering, to a patient in need of such treatment, a therapeutically effective amount of an antibody or a functional fragment thereof as defined in the first aspect, a peptide as defined in the third aspect, a nucleic acid as defined in the fourth aspect, or an antibody-drug conjugate as defined in the fifth aspect, each being optionally derivatised.

The term "derivatised" can mean that the antibody or functional fragment thereof, peptide, nucleic acid or conjugate may be modified prior to use, preferably to produce a derivative or variant thereof. Examples of derivatisation may include PEGylated antibodies or PEGylated antibody fragments, or antibody-cytokine fusion proteins. However, in some embodiments, the antibody or functional fragment thereof, peptide, nucleic acid or conjugate may not be derivatised.

ROR2 is expressed in a wide range of human cancer types, and so the antibody or functional fragment thereof, peptide, a nucleic acid or conjugate may be used in the treatment, prevention, amelioration or diagnosis of a ROR2-positive cancer type. Examples of ROR2-positive cancers which may be treated may include chronic OS,[14] renal cell carcinoma, gastric cancer, malignant melanoma, oral squamous cell carcinoma, prostate cancer, osteosarcoma, and neuroblastoma. In a preferred embodiment, however, the antibody or fragment thereof may be used for treating or diagnosing neuroblastoma or osteosarcoma.

It will be appreciated that antibodies, fragments, peptides, nucleic acids and conjugates according to the invention (collectively referred to herein as "agents") may be used in a monotherapy (e.g. the use of an antibody or fragment thereof alone, or the use of the antibody-drug conjugate alone), for treating, ameliorating or preventing cancer. Alternatively, agents according to the invention may be used as an adjunct to, or in combination with, known therapies for treating, ameliorating, or preventing cancer, preferably neuroblastoma or osteosarcoma.

The agents according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the agents across the blood-brain barrier.

Medicaments comprising agents of the invention may be used in a number of ways. For instance, oral administration may be required, in which case the agents may be contained within a composition that may, for example, be ingested orally in the form of a tablet, capsule or liquid. Compositions comprising agents and medicaments of the invention may be administered by inhalation (e.g. intranasally). Compositions may also be formulated for topical use. For instance, creams or ointments may be applied to the skin.

Agents and medicaments according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with agents used according to the invention is required and which would normally require frequent administration (e.g. at least daily injection).

In a preferred embodiment, agents and medicaments according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the antibodies, fragments, peptides and nucleic acids (i.e. agent) that is required is determined by its biological activity and bioavailability, which in turn depends on the mode of administration, the physiochemical properties of the agent, and whether it is being used as a monotherapy or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the bacterial infection. Additional factors depending on the particular subject being treated will result in a need to adjust dosages, including subject age, weight, gender, diet, and time of administration.

Generally, a daily dose of between 0.001 µg/kg of body weight and 10 mg/kg of body weight of agent according to the invention may be used for treating, ameliorating, or preventing cancer, depending upon which agent. More preferably, the daily dose of agent is between 0.01 µg/kg of body weight and 1 mg/kg of body weight, more preferably between 0.1 µg/kg and 100 µg/kg body weight, and most preferably between approximately 0.1 µg/kg and 10 µg/kg body weight.

The agent may be administered before, during or after onset of cancer. Daily doses may be given as a single administration (e.g. a single daily injection). Alternatively, the agent may require administration twice or more times during a day. As an example, agents may be administered as two (or more depending upon the severity of the cancer infection being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agents according to the invention to a patient without the need to administer repeated doses. Known procedures, such as those conventionally employed by the pharmaceutical industry (e.g. in vivo experimentation, clinical trials, etc.), may be used to form specific formulations of the agents according to the invention and precise therapeutic regimes (such as daily doses of the agents and the frequency of administration).

In a ninth aspect of the invention, there is provided a pharmaceutical composition comprising an antibody or a functional fragment thereof as defined in the first aspect, a peptide as defined in the third aspect, a nucleic acid as defined in the fourth aspect, or an antibody-drug conjugate as defined in the fifth aspect, each being optionally derivatised; and optionally a pharmaceutically acceptable vehicle.

The composition may be an anti-cancer composition. The term "anti-cancer composition" can mean a pharmaceutical formulation used in the therapeutic amelioration, prevention or treatment of cancer in a subject.

The antibody or a functional fragment thereof, peptide or a nucleic acid may not be derivatised.

The invention also provides in a tenth aspect, a process for making the pharmaceutical composition according to the ninth aspect, the process comprising combining a therapeutically effective amount of an antibody or a functional fragment thereof as defined in the first aspect, a peptide as defined in the third aspect, a nucleic acid as defined in the fourth aspect, or an antibody-drug conjugate as defined in the fifth aspect, each being optionally derivatised, with a pharmaceutically acceptable vehicle.

The antibody or fragment thereof may be as defined with respect to the first aspect.

A "subject" may be a vertebrate, mammal, or domestic animal. Hence, medicaments according to the invention may be used to treat any mammal, for example livestock (e.g. a horse), pets, or may be used in other veterinary applications. Most preferably, the subject is a human being.

Preferably, the subject is a child or adolescent, i.e. less than 15 or to years old.

A "therapeutically effective amount" of the antibody or fragment thereof is any amount which, when administered to a subject, is the amount of agent that is needed to treat the cancer, or produce the desired effect.

For example, the therapeutically effective amount of antibody or fragment thereof used may be from about 0.001 ng to about 1 mg, and preferably from about 0.01 ng to about 100 ng. It is preferred that the amount of antibody or fragment is an amount from about 0.1 ng to about to ng, and most preferably from about 0.5 ng to about 5 ng.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The agent may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The invention also provides a kit for diagnosing patients suffering from cancer.

Hence, according to an eleventh aspect of the invention, there is provided a kit for diagnosing a subject suffering from cancer, or a pre-disposition thereto, or for providing a prognosis of the subject's condition, the kit comprising detection means for detecting the concentration of antigen present in a sample from a test subject, wherein the detection means comprising an antibody or functional fragment thereof as defined by the first aspect, a peptide as defined by the third aspect, or a nucleic acid as defined by the fourth aspect, each being optionally derivatised, wherein presence of antigen in the sample suggests that the subject suffers from cancer.

According to a twelfth aspect, there is provided a method for diagnosing a subject suffering from cancer, or a pre-disposition thereto, or for providing a prognosis of the subject's condition, the method comprising detecting the concentration of antigen present in a sample obtained from a subject, wherein the detection is achieved using an antibody or functional fragment thereof as defined by the first aspect, a peptide as defined by the third aspect, or a nucleic acid as defined by the fourth aspect, each being optionally derivatised, and wherein presence of antigen in the sample suggests that the subject suffers from cancer.

Preferably, the antigen comprises or consists of ROR2 protein, or an epitope common to ROR1 and ROR2, more preferably an extracellular domain thereof. The sample may comprise blood, urine, tissue etc.

Preferably, the kit or method is used to identify the presence or absence of ROR1- and/or ROR2-positive cells in the sample, or determine the concentration thereof in the sample. The term "ROR2-positive cells" can mean a cell expressing ROR2 on its surface. Similarly, the term "ROR1-positive cells" can mean a cell expressing ROR1 on its surface. The detection means may comprise an assay adapted to detect the presence and/or absence of ROR1- and/or ROR2-positive cells in the sample. The kit or method may comprise the use of a positive control and/or a negative control against which the assay may be compared. For example, the kit may comprise a reference for the concentration of ROR1- and/or ROR2-positive cells in a sample from an individual who does (i.e. positive control) or does not (i.e. a negative control) suffer from cancer.

The kit may further comprise a label which may be detected. The term "label" can mean a moiety that can be attached to the antibody, fragment, peptide or nucleic acid. Moieties can be used, for example, for therapeutic or diagnostic procedures. Therapeutic labels include, for example, moieties that can be attached to an antibody or fragment thereof of the invention and used to monitor the binding of the antibody to a ROR1 and/or a ROR2 protein.

Diagnostic labels include, for example, moieties which can be detected by analytical methods. Analytical methods include, for example, qualitative and quantitative procedures. Qualitative analytical methods include, for example, immunohistochemistry and indirect immunofluorescence. Quantitative analytical methods include, for example, immunoaffinity procedures such as radioimmunoassay, ELISA or FACS analysis. Analytical methods also include both in vitro and in vivo imaging procedures. Specific examples of diagnostic labels that can be detected by analytical means include enzymes, radioisotopes, fluorochromes, chemiluminescent markers, and biotin.

A label can be attached directly to an antibody of the invention, fragment thereof, peptide or nucleic acid, or be attached to a secondary binding agent that specifically binds a molecule of the invention. Such a secondary binding agent can be, for example, a secondary antibody. A secondary antibody can be either polyclonal or monoclonal, and of human, rodent or chimeric origin.

As described in Example 3, the inventors have demonstrated how a recombinant full length IgG1 human monoclonal antibody of the invention may be made. For example, the antibody or functional fragment thereof may be produced by a bacteriophage expression system. Preferably, the bacteriophage expression system comprises a phage display library.

A useful procedure for isolating the polynucleotide which encodes the antibody or functional fragment thereof begins with isolation of cDNA which can be reverse-transcribed from RNA isolated from an individual suffering from cancer, such as CLL. This disease state is characterised by the presence of antibodies with immunospecificity against ROR2. Methods for cDNA synthesis are well known in the art. A cDNA encoding an antibody or functional fragment thereof including a heavy or light chain can be amplified using, for example, the polymerase chain reaction (PCR), preferably reverse transcription PCR (RT-PCR).

Suitable primers for PCR may be determined by those skilled in the art using conserved sequences which flank the particular functional fragment of a heavy or light chain. Suitable PCR conditions may be determined by those skilled in the art.

Preferably, the PCR is adapted to amplify the heavy chain, more preferably the VH CH-1 fragment, and even more preferably, the heavy chain variable fragment (VH). Alternatively, or additionally, the PCR may be adapted to amplify the light chain, more preferably the VL CL fragment, and even more preferably, the light chain variable fragment (VL). Preferably, the PCR products are cloned into a suitable expression vector, more preferably a phage expression vector, one embodiment of which is illustrated in FIGS. 9*a* and 9*b*.

Preferably, the vector is introduced into a suitable host, for example, Chinese hamster ovary (CHO) cells, for expression of the heavy and preferably, the light fragment, to occur. A suitable vector and host cell system can allow, for example, co-expression and assembly of functional fragments of the heavy and light chains. Preferably, the vector is introduced into the host by electroporation. Other suitable systems for the expression of antibody fragments can be determined by those skilled in the art and include, for example, M13 phage expression vectors. Recombinant monoclonal antibodies or functional fragments thereof can be substantially purified using methods known in the art, and which depend on the particular vector and host expression system used.

In a thirteenth aspect, there is provided a genetic construct comprising the nucleic acid of the fourth aspect.

Genetic constructs of the invention may be in the form of an expression cassette, which may be suitable for expression of the encoded polypeptide in a host cell. The genetic construct may be introduced in to a host cell without it being incorporated in a vector. For instance, the genetic construct, which may be a nucleic acid molecule, may be incorporated within a liposome or a virus particle. Alternatively, a purified nucleic acid molecule (e.g. histone-free DNA, or naked DNA) may be inserted directly into a host cell by suitable means, e.g. direct endocytotic uptake. The genetic construct may be introduced directly in to cells of a host subject (e.g. a bacterial cell) by transfection, infection, electroporation, microinjection, cell fusion, protoplast fusion or ballistic bombardment. Alternatively, genetic constructs of the invention may be introduced directly into a host cell using a particle gun. Alternatively, the genetic construct may be harboured within a recombinant vector, for expression in a suitable host cell.

Therefore, in a fourteenth aspect, there is provided a recombinant vector comprising the genetic construct according to the thirteenth aspect.

The recombinant vector may be a plasmid, cosmid or phage. Such recombinant vectors are useful for transforming host cells with the genetic construct of the thirteenth aspect, and for replicating the expression cassette therein. The skilled technician will appreciate that genetic constructs of the invention may be combined with many types of backbone vector for expression purposes. Examples of suitable backbone vectors include those shown in FIGS. 9*a* and 9*b*. Recombinant vectors may include a variety of other functional elements including a suitable promoter to initiate gene expression. For instance, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. Alternatively, the selectable marker gene may be in a different vector to be used simultaneously with vector containing the gene of interest. The vector may also comprise DNA involved with regulating expression of the coding sequence, or for targeting the expressed polypeptide to a certain part of the host cell.

In another embodiment, there is provided a vector substantially as represented in FIG. 9*a* or 9*b*.

In a fifteenth aspect, there is provided a host cell comprising the genetic construct according to the thirteenth aspect, or the recombinant vector according to the fourteenth aspect.

The host cell may be a bacterial cell. The host cell may be an animal cell, for example a mouse or rat cell. It is preferred that the host cell is not a human cell. The host cell may be transformed with genetic constructs or vectors according to the invention, using known techniques. Suitable means for introducing the genetic construct into the host cell will depend on the type of cell.

According to a sixteenth aspect, there is provided a method of preparing a recombinant antibody or functional fragment thereof, the method comprising—(i) culturing at least one cell defined in the fifteenth aspect capable of expressing the required antibody or functional fragment thereof; and (ii) isolating the antibody or functional fragment thereof.

As described herein, antibodies according to the first aspect of the invention can bind to ROR2. However, the inventors realise that the antibody or functional fragment thereof of the invention may be used to act as a framework for the development of antibodies showing immunospecificity against other members of the ROR family. For example, through introducing mutations into the CDRs of the ROR2-specific antibodies described herein, it is possible to isolate antibodies that can recognize ROR1 in one embodiment, or both ROR1 and ROR2 in another embodiment (see FIG. 5).

Hence, according to a seventeenth aspect there is provided a method of isolating an antibody or a functional fragment thereof having ability to bind to Receptor Tyrosine Kinase-Like Orphan Receptor 1 (ROR1), the method comprising:
  (i) mutating an antibody or functional fragment thereof as defined in the first aspect to produce a mutant; and
  (ii) selecting the mutant for immunospecificity against ROR1.

The mutant may be specific for ROR1, or for both ROR1 and ROR2.

In a first embodiment, said mutating step may comprise random mutagenesis, for example using degenerative PCR. For example, cDNA for the antibody is used as a template in a PCR reaction which may be doped with a mutagen, such as a mutagenic nucleoside triphosphate, for example dP and 8oxo-2'deoxyguanosine. Advantageously, this allows the introduction of mutations in a highly controlled manner throughout the cDNA to produce a mutant library. The resultant library of mutants may be displayed on the surface of a phage, and antibodies may then be selected against ROR1.

The resultant library of mutant antibodies may be selected against ROR1 using biopanning. For example, an ELISA plate may be coated with ROR1, such as with 100 μl of a 1 pgml$^{-1}$ solution of ROR1 in bicarbonate buffer pH 8.6, and incubated overnight at 4° C. The plate may then be washed with buffer, such as TBS. The plate may then be blocked, for example with 5% BSA in PBS and incubated for one hour at 37° C. After two further washes, 100 μl phage suspensions may be added to each well and the plate may be incubated for two hours at 37° C.

The phage may be removed and the wells filled with TBS 0.05% Tween 20 (TBST) and pipetted vigorously. After 5 minutes, the TBST may be removed, and for a first round of panning, the plate may be washed by this method once. In a second round of panning, 5 washes may be used, and in a third and subsequent rounds to washes may be used. The phage may then be eluted with 50 pl of elution buffer per well and incubated at room temperature for to minutes. After vigorous pipetting, eluted phage may be removed and neutralised with 3 pl of 2M Tris base.

In a second embodiment, said mutating may comprise introducing at least one ligand having immunospecificity against ROR1 into at least one antigen binding region of the antibody of the first aspect. The at least one ligand may comprise or consist of at least one of the six CDRs of a ROR1-specific antibody, for example any one of the dual binding ROR1/ROR2 dual binding antibodies described herein, i.e. clone #16, #84, #121 or #159. For example, the CDRs from clone #84 may be used. The amino acid sequence of the CDRs for clone #84 are preferably SEQ ID No:49, 51, 53, 55, 57 and/or 59. The nucleotide sequence encoding the clone #84 CDRs are preferably SEQ ID No:50, 52, 54, 56, 58 and/or 60. These sequences are shown in Table 1 or 2:

TABLE 1

The DNA sequence of the conserved CDR motifs of ROR$_1$ antibodies

| Light Chain CDR$_1$ (SEQ ID Nos. in parenthesis) | Light Chain CDR$_2$ (SEQ ID Nos. in parenthesis) | Light Chain CDR$_3$ (SEQ ID Nos. in parenthesis) | Heavy Chain CDR$_1$ (SEQ ID Nos. in parenthesis) | Heavy Chain CDR$_2$ (SEQ ID Nos. in parenthesis) | Heavy Chain CDR$_3$ (SEQ ID Nos. in parenthesis) |
|---|---|---|---|---|---|
| Caaagcctcgttca cagtgatggaaaca cctac (56) | Aaagtttct (58) | Atgcaaacc acacactggc ctccgacg (60) | Ggattca cctttagt agctattg g (50) | Ataaagcaa gatggaagt gagaaa (52) | Gcgcgcggttctt tctcttacgacagt gatctg (54) |

TABLE 2

The amino acid sequence of the conserved CDR motifs of ROR$_1$ antibodies

| Light Chain CDR$_1$ (SEQ ID Nos. in parenthesis) | Light Chain CDR$_2$ (SEQ ID Nos. in parenthesis) | Light Chain CDR$_3$ (SEQ ID Nos. in parenthesis) | Heavy Chain CDR$_1$ (SEQ ID Nos. in parenthesis) | Heavy Chain CDR$_2$ (SEQ ID Nos. in parenthesis) | Heavy Chain CDR$_3$ (SEQ ID Nos. in parenthesis) |
|---|---|---|---|---|---|
| QSLVHSDG NTY (55) | KVS (57) | MQTTHWPPT (59) | GFTFSSY W (49) | IKQDGS EK (51) | ARGSFSYD SDL (53) |

The at least one antigen binding region may be in the heavy and/or light chain variable fragment. Preferably, the at least one ligand is introduced into any of the antigen binding regions in the heavy chain of the immunoglobulin or functional fragment thereof.

The ligand may be inserted by restriction enzyme digestion at an appropriate site determined by a variety of techniques including molecular modelling. A polynucleotide sequence encoding the ligand peptide sequence may be ligated into the cut restriction site, the exact details of this depending on the nature of ligand and the CDR being used.

According to an eighteenth aspect, there is provided a library or panel of recombinant antibodies or functional fragments thereof, generated using the method defined in the seventeenth aspect.

According to a nineteenth aspect of the invention, there is provided a chimeric antigen receptor (CAR) that comprises an ectodomain comprising the human anti-Receptor Tyrosine Kinase-Like Orphan Receptor 2 (ROR2) antibody, or a functional fragment thereof according to the first aspect, or the isolated peptide of the third aspect.

The ectodomain may further comprise one chimeric chain or two chimeric chains. In embodiments where there are two chimeric chains, the chains may be bound to each other by a disulphide bond. It will be appreciated that one or both chimeric chains of the ectodomain comprise an antigen binding moiety. The chimeric chain or chains of the ectodomain may be selected from:—a T cell receptor alpha chain, a T cell receptor beta chain, a T cell receptor gamma chain, a T cell receptor delta chain and a CD28 ectodomain. The ectodomain may alternatively comprise part of a T cell receptor chain, such as the constant region of the T cell receptor chain.

Preferably, the CAR comprises a transmembrane domain. The transmembrane domain may comprise a CD3-zeta domain, a CD28 domain, a CD4 domain a CD8 domain or a T cell receptor domain. It will be appreciated that in embodiments where the transmembrane domain is CD3-zeta domain, a CD28 domain, a CD8 domain or a T cell receptor domain, the transmembrane domain may comprise a single transmembrane chain or two separate transmembrane chains. Preferably, the or each chain of the transmembrane domain is connected to an ectodomain comprising the isolated peptide of the third aspect or an antibody, or a functional fragment thereof according to the first aspect.

Preferably, the CAR comprises an endodomain. The endodomain may comprise one or more signalling domains. The signalling domain may comprise a CD3-zeta signalling domain, a CD28 signalling domain, a CD137 signalling domain or an OX-40 signalling domain. It will be appreciated that the CD3-zeta signalling domain, the CD28 signalling domain, the CD137 signalling domain and the OX-40 signalling domain may comprise one or more separate chains. Preferably, the or each chain of the transmembrane domain is connected to a single chain of the CD3-zeta signalling domain, the CD28 signalling domain, the CD137 signalling domain or the OX-40 signalling domain.

According to a twentieth aspect of the invention, there is provided an effector cell comprising the CAR of the nineteenth aspect.

According to a twenty-first aspect of the invention, there is provided an effector cell according to the twentieth aspect, for use in therapy or diagnosis.

According to a twenty-second aspect of the invention, there is provided an effector cell according to the twentieth aspect, for use in treating, preventing or ameliorating cancer.

The effector cell according to the twentieth, the twenty-first or the twenty-second aspect may be a somatic cell or a leukocyte. The leukocyte may be a lymphocyte, a natural killer cell, a monocyte, a macrophage, an eosinophil, a basophil or a neutrophil. The lymphocyte may be a T lymphocyte or a B lymphocyte. Preferably, the effector cell is a T lymphocyte. Hence, in one preferred embodiment, the effector cell is a chimeric antigen receptor T cell (CAR-T).

According to a twenty-third aspect, there is provided a method of treating, preventing or ameliorating cancer in a subject, the method comprising administering, to a patient in need of such treatment, a therapeutically effective amount of an effector cell according to the twentieth aspect.

The cancer may be neuroblastoma or osteosarcoma.

According to a twenty-fourth aspect of the invention, there is provided a genetic construct encoding the CAR of the nineteenth aspect.

According to a twenty-fifth aspect of the invention, there is provided a recombinant vector comprising the genetic construct of the twenty-fourth aspect.

According to a twenty-sixth aspect of the invention, there is provided a method of creating a CAR according to the nineteenth aspect, the method comprising transforming an effector cell with the genetic construct of the twenty-fourth aspect or the recombinant vector of the twenty-fifth aspect.

The effector cell may be a somatic cell or a leukocyte. The leukocyte may be a lymphocyte, a natural killer cell, a monocyte, a macrophage, an eosinophil, a basophil or a neutrophil. The lymphocyte may be a T lymphocyte or a B lymphocyte. Preferably, the effector cell is a T lymphocyte.

It will be appreciated that the invention extends to any nucleic acid or peptide or variant, derivative or analogue thereof, which comprises or consists of substantially the amino acid or nucleic acid sequences of any of the sequences referred to herein, including functional variants or functional fragments thereof. The terms "substantially the amino acid/nucleotide/peptide sequence", "functional variant" and "functional fragment", can be a sequence that has at least 40% sequence identity with the amino acid/nucleotide/peptide sequences of any one of the sequences referred to herein, for example 40% identity with the sequence identified as SEQ ID No:225 (i.e. the polypeptide sequence of one embodiment of human ROR2) or the nucleotide identified as SEQ ID No. 224 (i.e. the DNA sequence encoding one embodiment of human ROR2), and so on.

Amino acid/polynucleotide/polypeptide sequences with a sequence identity which is greater than 50%, more preferably greater than 65%, 70%, 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. blosum62, pam250, gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=-1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. hence, a most preferred method for calculating percentage identity between two sequences comprises (i) preparing a sequence alignment using the clustalw program using a suitable set of parameters, for example, as set out above; and (ii) inserting the values of n and t into the following formula:—sequence identity=(N/T)*100.

Alternative methods for identifying similar sequences will be known to those skilled in the art. For example, a substantially similar nucleotide sequence will be encoded by a sequence which hybridizes to any of the nucleic acid sequences shown herein, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×ssc/0.1% SDS at approximately 20-65° C. Alternatively, a substantially similar polypeptide may differ by at least 1, but less than 5, 10, 20, 50 or too amino acids from the sequences shown herein.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

EMBODIMENTS

In one aspect of the invention, there is provided a human anti-Receptor Tyrosine Kinase-Like Orphan Receptor 2 (ROR2) antibody, or a functional fragment thereof. In an embodiment, the functional fragment comprises a fragment selected from a group consisting of VH, VL, Fd, Fv, Fab, Fab', scFv, F (ab')$_2$ and Fc fragment. In an embodiment, the antibody or functional fragment thereof selectively interacts with ROR2 peptide with an affinity constant of approximately $10^{-5}$ to $10^{-13}$ $M^{-1}$, preferably $10^{-6}$ to $10^{-9}$ $M^{-1}$, even more preferably, 10–10 to $10^{-12}$ $M^{-1}$. In an embodiment, the antibody or fragment exhibits an $IC_{50}$ for ROR2 of about $10^{-7}$ to $10^{-11}$ $M^{-1}$ or $10^{-7}$ to $10^{-9}$ $M^{-1}$, wherein the IC50 is calculated using a competition ELISA.

In an embodiment, the antibody or fragment thereof is capable of mediating killing or shrinking ROR2-expressing tumour cells, or inhibiting cancer cell proliferation. In an embodiment, the antibody of fragment thereof is capable of being endocytosed upon binding to ROR2. In an embodiment, the antibody or fragment thereof is capable of binding to one or more the following epitopes, or a fragment or variant thereof, selected from a group of epitopes consisting of:

```
                                    (SEQ ID No. 226)
          TGYYQCVATNGMKTI;

(SEQ ID No. 227)
          RGIACARFIGNRTIY;

(SEQ ID No. 228)
          KTITATGVLFVRLGP;

(SEQ ID No. 229)
          CQPYRGIACARFIGNRTIY;

(SEQ ID No. 230)
          QCSQFAIPSFCHFVFPLCD;

(SEQ ID No. 231)
          ELCRDECEVLESDLC;

(SEQ ID No. 232)
          ANCMRIGIPAERLGR;
``` and
the rest of the sequence of the extracellular domain of ROR2 (i.e. SEQ ID No. 233), or a functional fragment or variant of any of these epitopes.

In an embodiment, the antibody or functional fragment thereof comprises at least one antigen binding region comprising an amino acid sequence, or a fragment or variant thereof, selected from a group consisting of:—
  (i) SEQ ID No:1, 3, 5, 7, 9 and/or 11;
  (ii) SEQ ID No:13, 15, 17, 19, 21 and/or 23;
  (iii) SEQ ID No:25, 27, 29, 31, 33 and/or 35;

(iv) SEQ ID No:37, 39, 41, 43, 45 and/or 47;
(v) SEQ ID No:49, 51, 53, 55, 57 and/or 59;
(vi) SEQ ID No:61, 63, 65, 67, 69 and/or 71;
(vii) SEQ ID No:73, 75, 77, 79, 81 and/or 83;
(viii) SEQ ID No:85, 87, 89, 91, 93 and/or 95;
(ix) SEQ ID No:97, 99, lot, 103, 105 and/or 107;
(x) SEQ ID No:109, 111, 113, 115, 117 and/or 119;
(xi) SEQ ID No:121, 123, 125, 127, 129 and/or 131;
(xii) SEQ ID No:133, 135, 137, 139, 141 and/or 143; and/or
(xiii) SEQ ID No:145, 147, 149, 151, 153 and/or 155.

In an embodiment, the antibody or functional fragment thereof comprises at least one antigen binding region encoded by a nucleotide sequence, or a fragment or variant thereof, selected from a group consisting of:—
(i) SEQ ID No:2, 4, 6, 8, 10 and/or 12;
(ii) SEQ ID No:14, 16, 18, 20, 22 and/or 24;
(iii) SEQ ID No:26, 28, 30, 32, 34 and/or 36;
(iv) SEQ ID No:38, 40, 42, 44, 46 and/or 48;
(v) SEQ ID No:50, 52, 54, 56, 58 and/or 60;
(vi) SEQ ID No:62, 64, 66, 68, 70 and/or 72;
(vii) SEQ ID No:74, 76, 78, 80, 82 and/or 84;
(viii) SEQ ID No:86, 88, 90, 92, 94 and/or 96;
(ix) SEQ ID No:98, 100, 102, 104, 106 and/or 108;
(x) SEQ ID No:110, 112, 114, 116, 118 and/or 120;
(xi) SEQ ID No:122, 124, 126, 128, 130 and/or 132;
(xii) SEQ ID No:134, 136, 138, 140, 142 and/or 144; and/or
(xiii) SEQ ID No:146, 148, 150, 152, 154 and/or 156.

In an embodiment, the antibody or functional fragment thereof comprises at least two, three, four, five or six amino acid sequences defined in any of (i) to (xiii). In an embodiment, the antibody of functional fragment thereof comprises a light chain variable region (VL) and/or a heavy chain variable region (VH), the light chain variable region comprising an amino acid sequence which is substantially as set out in SEQ ID Nos: 158, 162, 166, 170, 174, 178, 182, 186, 190, 194, 198, 202 or 206, or a functional fragment or variant thereof, and the heavy chain variable region comprising the amino acid sequence which is substantially as set out in SEQ ID Nos: 160, 164, 168, 172, 176, 180, 184, 188, 192, 196, 200, 204 or 208, or a functional fragment or variant thereof.

In an embodiment, the antibody of functional fragment thereof comprises a light chain variable region (VL) and/or a heavy chain variable region (VH), the light chain variable region being encoded by a polynucleotide comprising a nucleotide sequence which is substantially as set out in SEQ ID. Nos. 157, 161, 165, 169, 173, 177, 181, 185, 189, 193, 197, 201 or 205, or a functional fragment or variant thereof, the heavy chain variable region being encoded by a polynucleotide comprising a nucleotide sequence which is substantially as set out in SEQ ID. No: 159, 163, 167, 171, 175, 179, 183, 187, 191, 195, 199, 203 or 207, or a functional fragment or variant thereof.

In an embodiment, the antibody or functional fragment thereof corresponds to a clone selected from clones #016, #023, #024, #027, #084, #090, #093, #096, #121, #159, #173, #240 and #241. In an embodiment, the antibody or functional fragment thereof is also capable of binding to Receptor Kinase-Like Orphan Receptor 1 (ROR1). In an embodiment, the antibody or functional fragment thereof corresponds to a clone selected from clones #016, #084, #121, and #159.

In another aspect, a peptide comprises or consists of an amino acid sequence, or a fragment or variant thereof, selected from a group consisting of:—

(i) SEQ ID No:1, 3, 5, 7, 9 and/or 11;
(ii) SEQ ID No:13, 15, 17, 19, 21 and/or 23;
(iii) SEQ ID No:25, 27, 29, 31, 33 and/or 35;
(iv) SEQ ID No:37, 39, 41, 43, 45 and/or 47;
(v) SEQ ID No:49, 51, 53, 55, 57 and/or 59;
(vi) SEQ ID No:61, 63, 65, 67, 69 and/or 71;
(vii) SEQ ID No:73, 75, 77, 79, 81 and/or 83;
(viii) SEQ ID No:85, 87, 89, 91, 93 and/or 95;
(ix) SEQ ID No:97, 99, lot, 103, 105 and/or 107;
(x) SEQ ID No:109, 111, 113, 115, 117 and/or 119;
(xi) SEQ ID No:121, 123, 125, 127, 129 and/or 131;
(xii) SEQ ID No:133, 135, 137, 139, 141 and/or 143; and/or
(xiii) SEQ ID No:145, 147, 149, 151, 153 and/or 155.

In an embodiment, the isolated peptide is an anti-Receptor Tyrosine Kinase-Like Orphan Receptor 2 (ROR2) antibody, or a functional fragment thereof. In an embodiment, the isolated peptide comprises or consists of at least two, three, four, five or six amino acid sequences defined in any of (i) to (xiii).

In an embodiment, the peptide comprises or consists of an amino acid sequence substantially as set out in SEQ ID No: 158, 162, 166, 170, 174, 178, 182, 186, 190, 194, 198, 202 or 206, or a functional variant or fragment thereof, or an amino acid sequence substantially as set out in SEQ ID No: 160, 164, 168, 172, 176, 180, 184, 188, 192, 196, 200, 204 or 208, or a functional variant or fragment thereof.

In an embodiment, said peptide is chemically synthesized. In an embodiment, the peptide further comprises one or more protecting groups. In an embodiment, the one or more protecting groups are selected from the group consisting of acetyl, amide, 3 to 20 carbon alkyl groups, Fmoc, Tboc, 9-fluoreneacetyl group, 1-fluorenecarboxylic group, 9-florenecarboxylic group, 9-fluoronone-1-carboxylic group, benzyloxycarbonyl, Xanthyl(Xan), Trityl (Trt), 4-methyltrityl (Mtt), 4-methoxytrityl (Mmt), 4-methoxy-2,3,6-trimethylbenzenesulphonyl(Mtr), Mesitylene-2-sulphonyl (Mts), 4,4-dimethoxybenzhydryl(Mbh), Tosyl (Tos), 2,2,5,7,8-pentamethyl chroman-6-sulphonyl (Pmc), 4-methylbenzyl(MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Born), t-butoxycarbonyl (Boc), cyclohexyloxy (cHxO), t-butoxymethyl (Burn), t-butoxy (tBuO), t-Butyl (tBu), and Trifluoroacetyl (TFA). In an embodiment, the peptide is modified with a polymer to increase serum half-life. In an embodiment, the polymer comprises polyethylene glycol and/or cellulose or modified cellulose.

In another aspect, an isolated nucleic acid encodes a peptide capable of binding to Receptor Tyrosine Kinase-Like Orphan Receptor 2 (ROR2) protein, the nucleic acid comprising or consisting of a nucleotide sequence, or a fragment or variant thereof, selected from a group consisting of:—

(i) SEQ ID No:2, 4, 6, 8, 10 and/or 12;
(ii) SEQ ID No:14, 16, 18, 20, 22 and/or 24;
(iii) SEQ ID No:26, 28, 30, 32, 34 and/or 36;
(iv) SEQ ID No:38, 40, 42, 44, 46 and/or 48;
(v) SEQ ID No:50, 52, 54, 56, 58 and/or 60;
(vi) SEQ ID No:62, 64, 66, 68, 70 and/or 72;
(vii) SEQ ID No:74, 76, 78, 80, 82 and/or 84;
(viii) SEQ ID No:86, 88, 90, 92, 94 and/or 96;
(ix) SEQ ID No:98, 100, 102, 104, 106 and/or 108;
(x) SEQ ID No:110, 112, 114, 116, 118 and/or 120;

(xi) SEQ ID No:122, 124, 126, 128, 130 and/or 132;
(xii) SEQ ID No:134, 136, 138, 140, 142 and/or 144; and/or
(xiii) SEQ ID No:146, 148, 150, 152, 154 and/or 156.

In an embodiment, the nucleic acid encodes an anti-Receptor Tyrosine Kinase-Like Orphan Receptor 2 (ROR2) antibody, or a functional fragment thereof, optionally, wherein the nucleic acid comprises or consists of at least two, three, four, five or six nucleotide sequences defined in any of (i) to (xiii).

In an embodiment, the nucleic acid comprises or consists of a nucleotide sequence substantially as set out in SEQ ID No: 157, 161, 165, 169, 173, 177, 181, 185, 189, 193, 197, 201 or 205, or a functional variant or fragment thereof, or a nucleic acid may comprise a nucleotide sequence Jo substantially as set out in 159, 163, 167, 171, 175, 179, 183, 187, 191, 195, 199, 203 or 207, or a functional variant or fragment thereof.

In another aspect, an antibody-drug conjugate (ADC) comprises the antibody or a functional fragment thereof described herein, and a cytotoxic moiety. In an embodiment, the cytotoxic moiety is a toxin selected from monomethyl auristatin E (MMAE), monomethyl auristatin F (MMAF) or maytansine.

In another aspect, a chimeric antigen receptor (CAR) comprises an ectodomain comprising the human anti-Receptor Tyrosine Kinase-Like Orphan Receptor 2 (ROR2) antibody, or a functional fragment thereof described herein, or the isolated peptide described herein.

In an embodiment, the receptor comprises a transmembrane domain. In an embodiment, the transmembrane domain comprises a CD3-zeta domain, a CD28 domain, a CD4 domain, a CD8 domain, or a T cell receptor domain. In an embodiment, the receptor comprises an endodomain. In an embodiment, the endodomain comprises one or more signalling domains. In an embodiment, the signalling domain comprises a CD3-zeta signalling domain, a CD28 signalling domain, a CD137 signalling domain, or an OX-40 signalling domain.

In another aspect, an effector cell comprises the chimeric antigen receptor described herein.

In another aspect, there is provided an effector cell as described herein, for use in therapy or diagnosis.

In another aspect, there is provided an effector cell as described herein, for use in treating, preventing or ameliorating cancer. In an embodiment, the effector cell is a leukocyte. In an embodiment, wherein the leukocyte is a lymphocyte. In an embodiment, the lymphocyte is a chimeric antigen receptor T cell (CAR-T).

In another aspect, a method of treating, preventing or ameliorating cancer in a subject, comprises administering, to a patient in need of such treatment, a therapeutically effective amount of an effector cell as described herein. In an embodiment, the cancer is neuroblastoma or osteosarcoma.

In another aspect, a genetic construct encodes the CAR as described herein.

In another aspect, a recombinant vector comprises the genetic construct described herein.

In another aspect, a method of creating a CAR as described herein comprises transforming an effector cell with the recombinant vector described herein.

In another aspect, a method of treating, preventing or ameliorating cancer in a subject comprises administering, to a patient in need of such treatment, a therapeutically effective amount of an antibody or a functional fragment thereof, a peptide, a nucleic acid, an antibody-drug conjugate, or an effector cell, each being optionally derivatised, as described herein.

In an embodiment, the antibody or functional fragment thereof, peptide, a nucleic acid or conjugate may be used in the treatment, prevention, amelioration or diagnosis of a ROR2-positive cancer type. In an embodiment, the cancer is chronic OS, renal cell carcinoma, gastric cancer, malignant melanoma, oral squamous cell carcinoma, prostate cancer, osteosarcoma, and neuroblastoma.

In another aspect, a pharmaceutical composition comprises an antibody or a functional fragment thereof, a peptide, a nucleic acid, an antibody-drug conjugate, or an effector cell as described herein, each being optionally derivatised; and optionally a pharmaceutically acceptable vehicle.

In an embodiment, wherein the composition is an anti-cancer composition.

In another aspect, a process for making the composition comprises combining a therapeutically effective amount of an antibody or a functional fragment thereof, a peptide, a nucleic acid, an antibody-drug conjugate, or an effector cell as described herein, each being optionally derivatised, with a pharmaceutically acceptable vehicle.

In another aspect, a kit for diagnosing a subject suffering from cancer, or a pre-disposition thereto, or for providing a prognosis of the subject's condition, comprises detection means for detecting the concentration of antigen present in a sample from a test subject, wherein the detection means comprises an antibody or functional fragment thereof, a peptide, a nucleic acid, or an effector cell, as described herein, each being optionally derivatised, wherein presence of antigen in the sample suggests that the subject suffers from cancer.

In an embodiment, the antigen comprises ROR2 protein, or preferably an extracellular domain thereof. In an embodiment, the kit is used to identify the presence or absence of ROR2-positive cells in the sample, or determine the concentration thereof in the sample. In an embodiment, the kit comprises a positive control and/or a negative control against which the assay is compared. In an embodiment, wherein the kit further comprises a label which may be detected.

In another aspect, a method for diagnosing a subject suffering from cancer, or a pre-disposition thereto, or for providing a prognosis of the subject's condition, comprises detecting the concentration of antigen present in a sample obtained from a subject, wherein the detection is achieved using an antibody or functional fragment thereof, a peptide, a nucleic acid, or an effector cell as described herein, each being optionally derivatised, and wherein presence of antigen in the sample suggests that the subject suffers from cancer.

In another aspect, a genetic construct comprises the nucleic acid as described herein.

In another aspect, a recombinant vector comprises the genetic construct.

In another aspect, a host cell comprises the genetic construct.

In another aspect, a method of preparing a recombinant antibody or functional fragment thereof, comprises:—(i) culturing at least one cell described herein capable of expressing the required antibody or functional fragment thereof; and (ii) isolating the antibody or functional fragment thereof.

In another aspect, there is provided use of an epitope for generating an anti-Receptor Tyrosine Kinase-Like Orphan Receptor 2 (ROR2) antibody, or a functional fragment thereof, wherein the epitope comprises or consists of sequence selected from the group of epitopes consisting of: TGYYQCVATNGMKTI (SEQ ID No. 226); RGIACARFIGNRTIY (SEQ ID No. 227); KTITATGVLFVRLGP (SEQ ID No. 228); CQPYRGIACARFIGNRTIY (SEQ ID No. 229); QCSQFAIPSFCHFVFPLCD (SEQ ID No. 230); ELCRDECEVLESDLC (SEQ ID No. 231); and ANCMRIGIPAERLGR (SEQ ID No. 232); and the rest of the sequence of the extracellular domain of ROR2 (i.e. SEQ ID No. 233); or a functional fragment or variant of any of these epitopes.

All of the features described herein (including any accompanying claims, abstract and drawings), and/or all of the steps of any method or process so disclosed, may be combined with any of the above aspects in any combination, except combinations where at least some of such features and/or steps are mutually exclusive.

The following examples illustrate various aspects of the invention. The examples should, of course, be understood to be merely illustrative of only certain embodiments of the invention and not to constitute limitations upon the scope of the invention.

EXAMPLES

FIG. 1 is a Kaplan Meier curve showing that high expression levels of ROR2 correlate significantly with poorer overall survival among neuroblastoma cancer patients. This finding led the inventors to develop an antibody that can be used in the therapy and/or diagnosis of neuroblastoma.

Example 1—Generation of Candidates of Therapeutic Human mAbs Specific for Human ROR2 Extracellular Domain (ECD)

Through panning against the human ROR2 extracellular domain protein (ECD) using a fully-human antibody phage library, multiple ROR2-specific antibodies with a wide range of affinity were identified. FIG. 2 is a flow chart, which describes the process used to identify ROR2-specific antibodies present within 70 different phage display libraries.

A total of 1552 single chain Fv (scFv) phage antibodies were screened from enriched panning pools using ELISAs and flow cytometry against the ROR2 positive human colorectal cancer cell line, HCT116, in order to identify antibodies that recognize the native conformation of human ROR2.

ELISA

Using ELISAs, the inventors selected 199 unique clones exhibiting positive binding to human ROR2 ECD-Fc fusion protein and negative binding to control Fc-fusion protein and blank control (see FIG. 3). Table 3 is a summary of phage panning results. P-302

TABLE 3

Summary of phage panning results

| Time line | Number of Libraries | Number of Campaigns | Clones Screened | Human ROR2 positive Clones | Number of Unique Clones ROR2-specific | ROR1 and ROR2 dual binding |
|---|---|---|---|---|---|---|
| Feb. 22, 2011 to Sep. 30, 2011 | 70 | 42 | 1552 | 570 | 162 | 37 |

70 independent human antibody phage libraries were used in 42 parallel panning campaigns. 1552 individual phage clones from the enriched panning pools were screened by plate ELISA. Among them, 570 clones were ELISA positive. DNA sequence analysis indicated that there were 199 unique antibody clones, 162 were ROR2 specific clones, and 37 were dual specific clones (ROR1 and ROR2).

Binding affinity of 131 unique ELISA positive phage clones were estimated by competitive phage-binding ELISA. A diagram demonstrating the design of ROR2 competitive ELISA is shown in FIG. 4. Purified phage antibodies were first diluted serially in PBST buffer, and tested for binding to a ROR2-coated plate. The dilution that gave 50-80% saturating signal was used in the solution binding assay in which phage were first incubated with increasing concentration of ROR2 for one to two hours and then transferred to ROR2-coated plate for 10-15 minutes to capture the unbound phage. $IC_{50}$ was calculated as the concentration of ROR2 in solution-binding stage that inhibited 50% of the phage from binding to immobilized ROR2. Multiple antibodies with sub-nanomolar binding affinity as monovalent phage antibodies were identified through phage display (see Table 4).

TABLE 4

Summary of competitive ELISA results used to determine the binding affinity of 131 scFv of the ROR2-specific clones

| $IC_{50}$ (nM) | ≤1.0 | 1.0-10.0 | 10.0-100.0 | >100.0 | N.A |
|---|---|---|---|---|---|
| Number of clones | 7 | 17 | 35 | 5 | 67 |

37 (of the 1552) phage display antibodies were identified, by ELISA, as being capable of binding to human ROR1-ECD and human ROR2-ECD (see Table 3 and FIG. 5).

Flow Cytometry

Phage clones, with an IC50 greater than 10 nM against ROR2-ECD or which bind to both ROR1-ECD and ROR2-ECD, were screened further for cell-surface ROR2 recognition via flow cytometry. 13 clones were found to recognize ROR2-positive cancer cells, HCT116, but not ROR2 negative T lymphocyte cancer cells, Jurkat (see FIGS. 6 and 7).

FIG. 8 shows the binding of HCT116 and Jurkat cells to commercial anti-human ROR1 and anti-human ROR2 antibodies.

Example 2—Summary of the Preferred ROR2 Specific Antibodies

The inventors isolated 199 antibodies according to the invention. However, 13 of these 199 antibodies in particular are believed to be particularly valuable, and may be developed for therapeutic or diagnostic use. These 13 antibodies are selected by the following criteria:

1. They bind specifically to ROR2 (i.e. clone #023, #024, #027, #090, #093, #096, #173, #240 and #241) or bind specifically to both ROR1 and ROR2 (i.e. clone #016, #084, #121 and #159);
2. They have high ROR2-binding affinity; and
3. They form the pool that is likely to be converted into full IgG molecules for further analysis.

For each antibody, the information is organized as following:

1. Name of antibody;
2. Light chain variable region DNA sequence;
3. Light chain variable region protein sequence;
4. Heavy chain variable region DNA sequence; and
5. Heavy chain variable region protein sequence.

```
1) Antibody ROR2 clone #016
016-Lambda light chain variable region (DNA sequence)
                                                        [SEQ ID No. 157]
Tcttctgagctgactcaggaccctgctgtgtctgtggccttgggacagacagtcaggatcacatgccaag gagacagcctcagaagctattatgcaagctggtaccagcagaagccaggacaggcccctgtacttgtcat ctatggtaaaaacaaccggccctcagggatcccagaccgattctctggctccagctcaggaaacacagct tccttgaccatcactgggctcaggcggaagatgaggctgactattactgtaactcccgggacagcagtg gtaaccatctggtattcggcggagggaccaagctgaccgtcctagg 016-Lambda light chain variable region (amino acid sequence)
                                                        [SEQ ID No. 158]
SSELTQDPAVSVALGQTVRITCQGDSLRSYYASWYQQKPGQAPVLVIYGKNNRPSGIPDRFSGSSSGNTA

SLTITGAQAEDEADYYCNSRDSSGNHLVFGGGTKLTVLG

016-Heavy chain variable region (DNA sequence)
                                                        [SEQ ID No. 159]
Gaggtccagctggtacagtctggggctgaggtgaagaagcctggggcctcagtgaaggtctcctgcaagg cttctggatacaccttcaccgactactatatacactgggtgcggcaggcccctggacaagggctggagtg gatgggatggatgaaccctaacagtgggaactcagtctctgcacagaagttccagggcagagtcaccatg accagggatacctccataaacacagcctacatggagctgagcagcctgacatctgacgacacggccgtgt attactgtgcgcgcaactctgaatggcatccgtggggttactacgattactggggtcaaggtactctggt gaccgtctcctca 016-Heavy chain variable region (amino acid sequence)
                                                        [SEQ ID No. 160]
EVQLVQSGAEVKKPGASVKVSCKASGYTFTDYYIHWVRQAPGQGLEWMGWMNPNSGNSVSAQKFQGRVTM

TRDTSINTAYMELSSLTSDDTAVYYCARNSEWHPWGYYDYWGQGTLVTVSS

2) Antibody ROR2 clone #023
023-Kappa light chain variable region (DNA sequence)
                                                        [SEQ ID No. 161]
Gaaacgacactcacgcagtctccaggcaccctgtctgtgtctccaggggaaagagccaccctctcctgca gggccagtcagagtgttagcagcaacttagcctggtaccagcagaaacgtggccaggctcccaggctcct catctatggtgcgtctacccgggccactggtatcccagtcaggttcagtggcagtggtctgggacagag ttcactctcaccatcagcagattggagcctgaagattttgcagtgtattactgtcagcagtatggtaggt caccgctcactttcggcggagggaccaaagtggatatcaaacgt 023-Kappa light chain variable region (amino acid sequence)
                                                        [SEQ ID No. 162]
ETTLTQSPGTLSVSPGERATLSCRASQSVSSNLAWYQQKRGQAPRLLIYGASTRATGIPVRFSGSGSGTE

FTLTISRLEPEDFAVYYCQQYGRSPLTFGGGTKVDIKR
```

-continued

023-Heavy chain variable region (DNA sequence)
[SEQ ID No. 163]
gaagtgcagctggtgcagtctggagcagaggtgaaaaagcccggggagtctctgaagatctcctgtcagg gttctggatacaggttcagcaagtactggatcggctgggtgcgccagatgcccgggaaaggcctggagtg gatgggatcatctatcctggtgactctgataccagatacagcccgtccttccaaggccaggtcaccatc tcagccgacaagtccatcagcaccgcctacctgcagtggagcagcctgaaggcctcggacaccgccatgt attactgtgcgcgctctttctcttctttcatctacgattactggggtcaaggtactctggtgaccgtctc ctca 023-Heavy chain variable region (amino acid sequence)
[SEQ ID No. 164]
EVQLVQSGAEVKKPGESLKISCQGSGYRFSKYWIGWVRQMPGKGLEWMGIIYPGDSDTRYSPSFQGQVTI

SADKSISTAYLQWSSLKASDTAMYYCARSFSSFIYDYWGQGTLVTSS

3) Antibody ROR2 clone #024
024-Kappa light chain variable region (DNA sequence)
[SEQ ID No. 165]
Gaaattgtgatgacacagtctccagccaccctgtctgtgtctccaggggaaagtgccaccctctcctgca gggccagtcagggtgttggcatcaacttagcctggtaccagcagagacctggccagcctcccaggctcct catctatgatgcatccaacagggccactggcatcccagccaggttcagtggcagtgggtctgggacagat ttcactctcaccatcagcagcctgcaggctgaagatgtggcagtctattactgtcagcaatactatagtt ttccgtggacgttcggccaggggaccaaggtggaaatcaaacgt 024-Kappa light chain variable region (amino acid sequence)
[SEQ ID No. 166]
EIVMTQSPATLSVSPGESATLSCRASQGVGINLAWYQQRPGQPPRLLIYDASNRATGIPARFSGSGSGTD

FTLTISSLQAEDVAVYYCQQYYSFPWTFGQGTKVEIKR

024-Heavy chain variable region (DNA sequence)
[SEQ ID No. 167]
Gaggtgcagctggtgcagtctggggcagaggtgaaaaagcccggggagtctctgaaaatctcctgtaagg cttctggatacagctttagcaactactggatcggctgggtgcgccagatgcccgggaaaggcctggagtg gatgggatcatctatcctgatgactctgataccagatacagcccgtccgtccaaggccaggtcaccatc tcagccgacaagtccatcagcaccgcctacctgcagtggtacagcctgaaggtcgcggacaccgccaaat attactgtgtgcgccctaggggggcttttgatatctggggccaagggaccacggtcaccgtctcctca 024-Heavy chain variable region (amino acid sequence)
[SEQ ID No. 168]
EVQLVQSGAEVKKPGESLKISCKASGYSFSNYWIGWVRQMPGKGLEWMGIIYPDDSDTRYSPSVQGQVTI

SADKSISTAYLQWYSLKVADTAKYYCVRPRGAFDIWGQGTTVTSS

4) Antibody ROR2 clone #027
027-Light chain variable region (DNA sequence)
[SEQ ID No. 169]
Cagtctgtgctgacgcagccgccctcagtgtctggggcccccagggcagagggtcacgatctcctgcactg ggagtagctccaacatggggcaggtcatgctgtacactggtaccagcaacttccaggaacagcccccaa actcctcatctatgataacgccaatcggccctcaggggtccctgaccgattctctggctcccagtctggc acttcagcctccctggccatcaccggactccagactggggacgaggccgattattactgcggaacatggg atgacagcccgagtgcttatgtcttcggaactgggaccaaggtcaccgtcctaggt 027-Light chain variable region (amino acid sequence)
[SEQ ID No. 170]
QSVLTQPPSVSGAPGQRVTISCTGSSSNIGAGHAVHWYQQLPGTAPKLLIYDNANRPSGVPDRFSGSQSG

TSASLAITGLQTGDEADYYCGTWDDSPSAYVFGTGTKVTVLG

027-Heavy chain variable region (DNA sequence)
[SEQ ID No. 171]
Caggtgcagctggtggagtctggggcagaggtgaaaaagcccggggagtctctgaaaatctcctgtaagg cttctggatacagctttagcaactactggatcggctgggtgcgccagatgcccgggaaaggcctggagtg

```
gatggggatcatctatcctgatgactctgataccagatacagcccgtccttccaaggccaggtcaccatc tcagccgacaagtccatcagcaccgcctacctgcagtggtacagcctgaaggtcgcggacaccgccaat attactgtgtgcgccctagggggctttgatatctggggccaagggaccacggtcaccgtctcctca
```

027-Heavy chain variable region (amino acid sequence)
[SEQ ID No. 172]
QVQLVESGAEVKKPGESLKISCKASGYSFSNYWIGWVRQMPGKGLEWMGIIYPDDSDTRYSPSFQGQVTI

SADKSISTAYLQWYSLKVADTAKYYCVRPRGAFDIWGQGTTVTVSS

5) Antibody ROR2 clone #084
084-Kappa light chain variable region (DNA sequence)
[SEQ ID No. 173]
```
gatgttgtgatgactcagtctccactctccctgcccgtcaccctggacagccggcctccatctcctgca ggtctagtcaaagcctcgttcacagtgatggaaacacctacttgaattggtttcagcagaggccaggcca atctccaaggcgcctaatttataaagtttctagccgggactctggggtcccagatagattcagcggcact gggtcaggcactgatttcacactgaaaatcagcagggtggaggctgaagatgttggcgtttattactgca tgcaaaccacacactggcctccgacgttcggccaagggaccaaggtggagatcaaacgt
```
084-Kappa light chain variable region (amino acid sequence)
[SEQ ID No. 174]
DVVMTQSPLSLPVTLGQPASISCRSSQSLVHSDGNTYLNWFQQRPGQSPRRLIYKVSSRDSGVPDRFSGT

GSGTDFTLKISRVEAEDVGVYYCMQTTHWPPTFGQGTKVEIKR

084-Heavy chain variable region (DNA sequence)
[SEQ ID No. 175]
```
caggtgcagctggtggagtctgggggaggcttggtccagcctggggggtccctgagactctcctgtgcag cctctggattcaccttagtagctattggatgagctgggtccgccaggctccagggaaagggctggagtg ggtggccaacataaagcaagatggaagtgagaaatactatgtggactctgtgaggggccgattcaccatc tccagagacaacgccaagaactcactgtatctgcaaatgaacagcctgagagccgaggacaccgccatgt attactgtgcgcgcggttctttctcttacgacagtgatctgtggggtcaaggtactctggtgaccgtctc ctca
```
084-Heavy chain variable region (amino acid sequence)
[SEQ ID No. 176]
QVQLVESGGGLVQPGGSLRLSCAASGFTFSSYWMSWVRQAPGKGLEWVANIKQDGSEKYYVDSVRGRFTI

SRDNAKNSLYLQMNSLRAEDTAMYYCARGSFSYDSDLWGQGTLVTVSS

6) Antibody ROR2 clone #90
090-Light chain variable region (DNA sequence)
[SEQ ID No. 177]
```
cagcctgtgctgactcagccaccctcagcgtctgggaccccgggcagagggtcaccatctcttgttctg gaagcagctccaacatcgggagtgattatgtatcctggtaccaacagctcccaggaacggcccccaaact cctcatctataggaatgatcagcggccctcaggggtccctgaccgattctctggctccaagtctggcacc tcagcctccctggccatcagtgggctccggtccgaggatgaggctgattattactgtgtagcatgggatg acagcctgagtggttatgtcttcggaagtgggaccaaggtcaccgtcctaggt
```
090-Light chain variable region (amino acid sequence)
[SEQ ID No. 178]
QPVLTQPPSASGTPGQRVTISCSGSSSNIGSDYVSWYQQLPGTAPKLLIYRNDQRPSGVPDRFSGSKSGT

SASLAISGLRSEDEADYYCVAWDDSLSGYVFGSGTKVTVLG

090-Heavy chain variable region (DNA sequence)
[SEQ ID No. 179]
```
gaggtgcagctggtggagtctggcccaggactggtgaagccttcacagaccctgtccctcacctgcactg tctctggtggctccatcagcagtggtggttactactggagctggatccgccagcacccagggaagggcct ggagtggattgggtacatctattacagtgggagcacctactacaacccgtccctcaagagtcgagttacc atatcagtagacacgtccaagaaccagttctccctgaagctgagctctgtgaccgctgcggacaccgcca
```

-continued tgtattactgtgcgcgcggtggtctgtactggacttactctcaggatgtttggggtcaaggtactctggt gaccgtctcctca 090-Heavy chain variable region (Amino acid sequence)
[SEQ ID No. 180]
EVQLVESGPGLVKPSQTLSLTCTVSGGSISSGGYYWSWIRQHPGKGLEWIGYIYYSGSTYYNPSLKSRVT

ISVDTSKNQFSLKLSSVTAADTAMYYCARGGLYWTYSQDVWGQGTLVTVSS

7) Antibody ROR2 clone #093
093-Kappa light chain variable region (DNA sequence)
[SEQ ID No. 181]
gaaattgtgatgacgcagtctccagccaccctgtctttgtctccaggggaaagagccaccctctcctgcg gggccagtcagagtgttagcagcagctacttagcctggtaccagcagaaacctggcctggcgcccaggct cctcatctatgatacatccagaagggccactggcatcccagacaggttcagtggcagtgggtctgggaca gacttcactctcaccatcagcagactggagccggaagattttgcagtgtattactgtcttcactatggtc gctcacctccggtcactttcggcggagggaccaaggtggagatcaaacgt 093-Kappa light chain variable region (amino acid sequence)
[SEQ ID No. 182]
EIVMTQSPATLSLSPGERATLSCGASQSVSSSYLAWYQQKPGLAPALLIYDTSRRATGIPDRFSGSGSGT

DFTLTISRLEPEDFAVYYCLHYGRSPPVTFGGGTKVEIKR

093-Heavy chain variable region (DNA sequence)
[SEQ ID No. 183]
Cagatgcagctggtgcagtctgggggaggcgtggtccagcctgggaggtccctgagactctcctgtgcag cctctggattcaccttcagtaactatgacatgcactgggtccgccgggctccaggcaaggggctggagtg ggtggcagttatatcatatgatggaagtaataattactatgcagactccgtgaagggccgattcaccatc tccagagacaattccaagaacacgctgtatctgcaaatgaacagcctgagagctgaggacacggccgtgt attactgtgcgcgctcttctgcttgggttggtggtggtttcctgtctggtactgatgactggggtcaagg tactctggtgaccgtctcctca 093-Heavy chain variable region (amino acid sequence)
[SEQ ID No. 184]
QMQLVQSGGGVVQPGRSLRLSCAASGFTFSNYDMHWVRRAPGKGLEWVAVISYDGSNNYYADSVKGRFTI

SRDNSKNTLYLQMNSLRAEDTAVYYCARSSAWVGGGFLSGTDDWGQGTLVTVSS

8) Antibody ROR2 clone #096
096-Light chain variable region (DNA sequence)
[SEQ ID No. 185]
gaaattgtgctgactcagtctccactctccctgcccgtcacccttggacagccggcctccatctcctgca ggtctagtcaaagcctcgcatacagtgatggaaacacctacttgaattggtttcaccagaggccaggcca atctccaaggcgcctaatctataaggtttctaagcgggactctggggtcccagacagattcagcggcagt gggtcaggcactgatttcacactgagaatcagcagggtggaggctgaggatgttgggatttattactgca tgcaaggtacacactggcctcacactttcggccctgggaccaaagtggatatcaaacgt 096-Light chain variable region (amino acid sequence)
[SEQ ID No. 186]
EIVLTQSPLSLPVTLGQPASISCRSSQSLAYSDGNTYLNWFHQRPGQSPRRLIYKVSKRDSGVPDRFSGS

GSGTDFTLRISRVEAEDVGIYYCMQGTHWPHTFGPGTKVDIKR

096-Heavy chain variable region (DNA sequence)
[SEQ ID No. 187]
Gaagtgcagctggtgcagtctgggggaggcttggtccagcctggagggtccctgagactctcctgtgcag cctctggattcagcctcaatgactattacatggactgggtccgccaggctccaggggaggggctggagtg ggttggccgtattagagacaaagctcacggtgacaccacagaatacatcgcgtctgtgaaagacagattt atcgtctcaagagatgactccaagaactcactgtatctgcaaatgaacagcctgaaaaccgaggacaccg ccatgtattactgtgcgcgctgggttgacgactaccagggttactggatctggtcttaccacgatttctg gggtcaaggtactctggtgaccgtctcctca 096-Heavy chain variable region (amino acid sequence)

[SEQ ID No. 188]

EVQLVQSGGGLVQPGGSLRLSCAASGFSLNDYYMDWVRQAPGEGLEWVGRIRDKAHGDTTEYIASVKDRF

IVSRDDSKNSLYLQMNSLKTEDTAMYYCARWVDDYQGYWIWSYHDFWGQGTLVTVSS

9) Antibody ROR2 clone #121
121-Light chain variable region (DNA sequence)

[SEQ ID No. 189]

tcctatgtgctgactcagccaccctcagtgtccgtgtccccaggacagacagccagcgtcacctgttctg gatatagattgagagagaagtatgtttcctggtatcaacagaggccaggccactcccctgtcttggtcat ctatgaagatactaagaggccttcagggatccctgagcgattctctggctccaattctggggacacagcc actctgaccatcagagggacccaggctatagatgaggctgactattactgtcaggcgtgggacagcagcg tgattttcggcggagggaccaagctgaccgtcctaggt 121-Light chain variable region (amino acid sequence)

[SEQ ID No. 190]

SYVLTQPPSVSVSPGQTASVTCSGYRLREKYVSWYQQRPGHSPVLVIYEDTKRPSGIPERFSGSNSGDTA

TLTIRGTQAIDEADYYCQAWDSSVIFGGGTKLTVLG

121-Heavy chain variable region (DNA sequence)

[SEQ ID No. 191]

caggtgcagctggtgcagtctgggggaggcttggtacagcctggggggtccctgagactctcctgtgcag ccactggattcacctttagcagctatgccatgagttgggtccgccaggctccagggaaggggctggagtg ggtctcagttattagtggtagtggtggtagcacatactacgcagactccgtgaagggccggttcaccatc tccagagacaattccaagaacacgttgtatctgcaaatgaacagcctgagagccgacgacactgccgtgt attactgtgcgcgccattactactcttctgattcttggggtcaaggtactctggtgaccgtctcctca 121-Heavy chain variable region (amino acid sequence)

[SEQ ID No. 192]

QVQLVQSGGGLVQPGGSLRLSCAATGFTFSSYAMSWVRQAPGKGLEWVSVISGSGGSTYYADSVKGRFTI

SRDNSKNTLYLQMNSLRADDTAVYYCARHYYSSDSWGQGTLVTVSS

10) Antibody ROR2 clone #159
159-Light chain variable region (DNA sequence)

[SEQ ID No. 193]

caatctgccctgactcagcctgcctccgtgtctgggtctcctggacagtcgatcaccatctcctgcactg gaaccagcagtgacgttggtggttataactatgtctcttggtaccaacagcacccaggcaaagcccccaa attcatgatttatgatgtcagtaagcggccctcaggtgtttctaatcgcttctctggctccaagtctggc aacacggcctccctgaccatctctgggctccaggctgaggacgaggctgattattactgcggctcatttta caagcagcatcacttatgtcttcggaactgggaccaaggtcaccgtcctaggt 159-Light chain variable region (amino acid sequence)

[SEQ ID No. 194]

QSALTQPASVSGSPGQSITISCTGTSSDVGGYNYVSWYQQHPGKAPKFMIYDVSKRPSGVSNRFSGSKSG

NTASLTISGLQAEDEADYYCGSFTSSITYVFGTGTKVTVLG

159-Heavy chain variable region (DNA sequence)

[SEQ ID No. 195]

cagatgcagctggtgcagtctggggctgaggtgaagaagcctggggcctcagtgaaggtttcctgcaagg catctggatacaccttcaccagctactatatgcactgggtgcgacaggcccctggacaagggcttgagtg gatgggaataatcaaccctagtggtggtagcacaagctacgcacagaagttccagggcagagtcaccatg accagggacacgtccacgagcacagtctacatggagctgagcagcctgagatctgaggacactgccgtgt attactgtgcgcgcggtggttacactggttggtctccgtctgatccgtggggtcaaggtactctggtgac cgtctcctca -continued 159-Light chain variable region (amino acid sequence)
[SEQ ID No. 196]
QMQLVQSGAEVKKPGASVKVSCKASGYTFTSYYMHWVRQAPGQGLEWMGIINPSGGSTSYAQKFQGRVTM

TRDTSTSTVYMELSSLRSEDTAVYYCARGGYTGWSPSDPWGQGTLVTVSS

11) Antibody ROR2 clone #173
173-Lambda light chain variable region (DNA sequence)
[SEQ ID No. 197]
Cagtctgtgttgactcagccaccctcagtgtcagtggccccaggaaagacggccaggattacctgtggtg gagacaacattggacgtaaaagtgtgcactggtaccagcagaagccaggccaggcccctgtgctggtcat ctattatgatagcgaccggccctcagggatccctgagcgattctctggctccacctctgggaacacggcc accctgaccatcagtagggtcgaagccggggatgaggccgactattactgtcaggtgtgggatcgtagta gtgacctttatgtcttcggaactgggaccaaggtcaccgtcctaggt 173-Lambda light chain variable region (amino acid sequence)
[SEQ ID No. 198]
QSVLTQPPSVSVAPGKTARITCGGDNIGRKSVHWYQQKPGQAPVLVIYYDSDRPSGIPERFSGSTSGNTA

TLTISRVEAGDEADYYCQVWDRSSDLYVFGTGTKVTVLG

173-Heavy chain variable region (DNA acid sequence)
[SEQ ID No. 199]
Caggtgcagctggtgcagtctggggctgaggtgaagaagcctggggcctcagtgaaggtctcctgcaagg cttctggttacaccttaccagctatggtatcagctgggtgcgacaggcccctggacaagggcttgagtg gatgggatggatcagcgcttacaatggtaacacaaactatgcacagaagctccagggcagagtcaccatg accacagacacatccacgagcacagcctatggagctgaggagcctgagatctgacgacacggctgtgt attactgtgcgcgccatctgggtccgatgggtatgtacgactggtctttcgataaatggggtcaaggtac tctggtgaccgtctcctca 173-Heavy chain variable region (amino acid sequence)
[SEQ ID No. 200]
QVQLVQSGAEVKKPGASVKVSCKASGYTFTSYGISWVRQAPGQGLEWMGWISAYNGNTNYAQKLQGRVTM

TTDTSTSTAYMELRSLRSDDTAVYYCARHLGPMGMYDWSFDKWGQGTLVTVSS

12) Antibody ROR2 clone #240
240-Light chain variable region (DNA acid sequence)
[SEQ ID No. 201]
caatctgccctgactcagcctgcctccgtgtctgggtctcctggacagtcgatcaccatctcctgcactg gaaccagcggtgacgttggcggttataactatgtctcctggtaccaacaccacccaggcaaagcccccaa actcataatttatgatgtcaataagcggccctcaggttttctgatcggttctctggctccaagtctggc aacacggcctccctgacaatctctgggctccaggctgaggacgaggctgattattactgcagctcatata caagcaccagcaccgtcttcggcggagggaccaagctgaccgtcctaggt 240-Light chain variable region (amino acid sequence)
[SEQ ID No. 202]
QSALTQPASVSGSPGQSITISCTGTSGDVGGYNYVSWYQHHPGKAPKLITYDVNKRPSGESDRFSGSKSG

NTASLTISGLQAEDEADYYCSSYTSTSTVFGGGTKLTVLG

240-Heavy chain variable region (DNA acid sequence)
[SEQ ID No. 203]
cagatcaccttgaaggagtctggtcctgagctggtgaaacccacacagaccctcacactgacctgcacct ttctgggttctcactcagcactagtggaatgtctgtgagctggatccgtcagcccccagggaaggccct ggagtggcttgcacgcattgattgggatgatgataaatactacagcacatctctgaagaccaggctcacc atctccaaggacacctccaaaaaccaggtggtccttacaatgaccaacacggaccctgtggacacagcca cgtattactgtgcgcgcggtttctacctggcttacggttcttacgattcttggggtcaaggtactctggt gaccgtctcctca 240-Heavy chain variable region (amino acid sequence)
[SEQ ID No. 204]
QITLKESGPELVKPTQTLTLTCTFSGFSLSTSGMSVSWIRQPPGKALEWLARIDWDDDKYYSTSLKTRLT

ISKDTSKNQVVLTMTNTDPVDTATYYCARGFYLAYGSYDSWGQGTLVTVSS

13) Antibody ROR2 clone #241
241-Light chain variable region (DNA acid sequence)
[SEQ ID No. 205]
tcctatgagctgactcagccactctcagtgtcagtggccctgggacagacggccaggattacctgtgggg gaaacaacattggaagtaaaaatgtgcactggtaccagcagaagccaggccaggcccctgtgctggtcat ctatagggatagcaaccggccctctgggatccctgagcgattctctggctccaactcggggaacacggcc accctgaccatcagcagagcccaagccggggatgaggctgactattactgtcaggtgtgggacagcagta ttgtggtattcggcggagggaccaagctgaccgtcctaggt 241-Light chain variable region (amino acid sequence)
[SEQ ID No. 206]
SYELTQPLSVSVALGQTARITCGGNNIGSKNVHWYQQKPGQAPVLVIYRDSNRPSGIPERFSGSNSGNTA

TLTISRAQAGDEADYYCQVWDSSIVVFGGGTKLTVLG

241-Heavy chain variable region (DNA acid sequence)
[SEQ ID No. 207]
Gaagtgcagctggtgcagtctggggctgaggtgaagaagcctggggcctcagtgaaggtttcctgcaagg catctggatacaccttcaccaattactatatacactgggtgcgacaggcccctggacaagggcttgagtg gatgggaataatcaaccctacaagtggtaggacaaggtacgcacagaggttccagggcagagtcaccatg accagggacacgtccacgaacacagtctacatggacctgagcagcctgagatctgaagacaccgccatgt attactgtgcgcgctctggttactactggggtgttaacggtgatcagtggggtcaaggtactctggtgac cgtctcctca 241-Heavy chain variable region (amino acid sequence)
[SEQ ID No. 208]
EVQLVQSGAEVKKPGASVKVSCKASGYTFTNYYIHWVRQAPGQGLEWMGIINPTSGRTRYAQRFQGRVTM

TRDTSTNTVYMDLSSLRSEDTAMYYCARSGYYWGVNGDQWGQGTLVTVSS

TABLE 5

The amino acid sequence of the conserved CDR motifs of anti-ROR$_2$ clones

| Antibody clone # | HCDR$_1$ (SEQ ID No. in parenthesis) | HCDR2 (SEQ ID No. in parenthesis) | HCDR$_3$ (SEQ ID No. in parenthesis) | LCDR$_1$ (SEQ ID No. in parenthesis) | LCDR$_2$ (SEQ ID No. in parenthesis) | LCDR$_3$ (SEQ ID No. in parenthesis) |
|---|---|---|---|---|---|---|
| ROR2-16 | GYTFTDYY (1) | MNPNSGNS (3) | ARNSEWHPWGYYDY (5) | SLRSYY (7) | GKN (9) | NSRDSSGNHLV (11) |
| ROR2-23 | GYRFSKYW (13) | IYPGDSDT (15) | ARSFSSFIYDY (17) | QSVSSN (19) | GAS (21) | QQYGRSPLT (23) |
| ROR2-24 | GYSFSNYW (25) | IYPDDSDT (27) | VRPRGAFDI (29) | QGVGIN (31) | DAS (33) | QQYYSFPWT (35) |
| ROR2-27 | GYSFSNYW (37) | IYPDDSDT (39) | VRPRGAFDI (41) | SSNIGAGHA (43) | DNA (45) | GTWDDSPSAYV (47) |
| ROR2-84 | GFTFSSYW (49) | IKQDGSEK (51) | ARGSFSYDSDL (53) | QSLVHSDGNTY (55) | ICVS (57) | MQTTHWPPT (59) |
| ROR2-90 | GGSISSGGY (61) | IYYSGST (63) | ARGGLYWTYSQDV (65) | SSNIGSDY (67) | RND (69) | VAWDDSLSGYV (71) |
| ROR2-93 | GFTFSNYD (73) | ISYDGSNN (75) | ARSSAWVGGGFLSGTDD (77) | QSVSSSY (79) | DTS (81) | LHYGRSPPVT (83) |

TABLE 5-continued

The amino acid sequence of the conserved CDR motifs of anti-ROR₂ clones

| Antibody clone # | HCDR₁ (SEQ ID No. in parenthesis) | HCDR2 (SEQ ID No. in parenthesis) | HCDR₃ (SEQ ID No. in parenthesis) | LCDR₁ (SEQ ID No. in parenthesis) | LCDR₂ (SEQ ID No. in parenthesis) | LCDR₃ (SEQ ID No. in parenthesis) |
| --- | --- | --- | --- | --- | --- | --- |
| ROR2-96 | GFSLNDYY (85) | IRDKAHGMT (87) | ARWVDDYQGYWIWSYHDF (89) | QSLAYSDGNTY (91) | KVS (93) | MQGTHWPHT (95) |
| ROR2-121 | GFTFSSYA (97) | ISGSGGST (99) | ARHYYSSDS (101) | RLREICY (103) | EDT (105) | QAWDSSVI (107) |
| ROR2-159 | GYTFTSYY (109) | INPSGGST (111) | ARGGYTGWSPSDP (113) | SSDVGGYNY (115) | DVS (117) | GSFTSSITYV (119) |
| ROR2-173 | GYTFTSYG (121) | ISAYNGNT (123) | ARHLGPMGMYDWSFDK (125) | NIGRKS (127) | YDS (129) | QVWDRSSDLYV (131) |
| ROR2-240 | GFSLSTSGMS (133) | IDWDDDK (135) | ARGFYLAYGSYDS (137) | SGDVGGYNY (139) | DVN (141) | SSYTSTSTV (143) |
| ROR2-241 | GYTFTNYY (145) | INPTSGRT (147) | ARSGYYWGVNGDQ (149) | NIGSICN (151) | RDS (153) | QVWDSSIVV (155) |

TABLE 6

The DNA sequence of the conserved CDR motifs of anti-ROR₂ clones

| Antibody clone # | HCDR₁ (SEQ ID No. in parenthesis) | HCDR₂ (SEQ ID No. in parenthesis) | HCDR₃ (SEQ ID No. in parenthesis) | LCDR₁ (SEQ ID No. in parenthesis) | LCDR₂ (SEQ ID No. in parenthesis) | LCDR₃ (SEQ ID No. in parenthesis) |
| --- | --- | --- | --- | --- | --- | --- |
| ROR2-16 | ggatacaccttcaccgactactat (2) | Atgaaccctaacagtgggaactca (4) | Gcgcgcaactctgaatggcatccgtggggttactacgattac (6) | Agcctcagaagctattat (8) | Ggtaaaaac (10) | Aactcccgggacagcagtggtaaccatctggta (12) |
| ROR2-23 | Ggatacaggttcagcaagtactgg (14) | Atctatcctggtgactctgatacc (16) | Gcgcgctctttctcttcttcatctacgattac (18) | Cagagtgttagcagcaac (20) | Ggtgcgtct (22) | Cagcagtatggtagtcaccgctcact (24) |
| ROR2-24 | Ggatacagcttagcaactactgg (26) | Atctatcctgatgactctgatacc (28) | Gtgcgccctaggggggcttttgatatc (30) | Cagggtgttggcatcaac (32) | Gatgcatcc (34) | Cagcaatactatagttttccgtggacg (36) |
| ROR2-27 | Ggatacagcttagcaactactgg (38) | Atctatcctgatgactctgatacc (40) | Gtgcgccctaggggggcttttgatatc (42) | Agctccaacatcggggcaggtcatgct (44) | Gataacgcc (46) | Ggaacatgggatgacagcccgagtgcttatgtc (48) |
| ROR2-84 | Ggattcaccttagtagctattgg (50) | Ataaagcaagatggaagtgagaaa (52) | Gcgcgcggttctttctcttacgacagtgatctg (54) | Caaagcctcgttcacagtgatggaaacacctac (56) | Aaagtttct (58) | Atgcaaaccacacactggcctccgacg (60) |
| ROR2-90 | Ggtggctccatcagcagtggtggttactac (62) | Atctattacagtgggagcacc (64) | Gcgcgcggtggtctgtactggacttactctcaggatgt (66) | Agctccaacatcgggagtgattat (68) | Aggaatgat (70) | Gtagcatgggatgacagcctgagtggttatgtc (72) |
| ROR2-93 | Ggattcaccttcagtaactatgac (74) | Atatcatatgatggaagtaataat (76) | Gcgcgctcttctgcttgggttggtggtttcctgtctggtactgatgac (78) | Cagagtgttagcagcagctac (80) | Gatacatcc (82) | Cttcactatggtcgctcacctccggtcact (84) |

TABLE 6-continued

The DNA sequence of the conserved CDR motifs of anti-ROR₂ clones

| Antibody clone # | HCDR₁ (SEQ ID No. in parenthesis) | HCDR₂ (SEQ ID No. in parenthesis) | HCDR₃ (SEQ ID No. in parenthesis) | LCDR₁ (SEQ ID No. in parenthesis) | LCDR₂ (SEQ ID No. in parenthesis) | LCDR₃ (SEQ ID No. in parenthesis) |
|---|---|---|---|---|---|---|
| ROR2-96 | Ggattcag cctcaatga ctattac (86) | Attagagac aaagctcacg gtgacaccac a (88) | Gcgcgctgggtt gacgactaccag ggttactggatct ggtataccacga tttc (90) | Caaagcctcgc atacagtgatg gaaacacctac (92) | Aaggtt tct (94) | Atgcaaggtacaca ctggcctcacact (96) |
| ROR2-121 | Ggattcac ctttagcag ctatgcc (98) | Attagtggta gtggtggtag caca (100) | Gcgcgccattact actcttctgattct (102) | Agattgagaga gaagtat (104) | Gaaga tact (106) | Caggcgtgggacag cagcgtgatt (108) |
| ROR2-159 | Ggatacac cttcaccag ctactat (110) | Atcaaccta gtggtggtag caca (112) | Gcgcgcggtggt tacactggttggt ctccgtctgatcc g (114) | Agcagtgacgt tggtggttataa ctat (116) | Gatgtc agt (118) | Ggctcattlacaagc agcatcacttatgtc (120) |
| ROR2-173 | Ggttacac ctttaccag ctatggt (122) | Atcagcgctt acaatggtaa caca (124) | Gcgcgccatctg ggtccgatgggta tgtacgactggtc tttcgataaa (126) | Aacattggacg taaaagt (128) | Tatgat agc (130) | Caggtgtgggatcgt agtagtgacctttatg tc (132) |
| ROR2-240 | Gggttctc actcagca ctagtgga atgtct (134) | Attgattggg atgatgataa a (136) | Gcgcgcggtttct acctggcttacgg ttcttacgattct (138) | Agcggtgacgt tggcggttataa ctat (140) | Gatgtc aat (142) | Agctcatatacaagc accagcaccgtc (144) |
| ROR2-241 | Ggatacac cttcaccaa ttactat (146) | Atcaaccta caagtggtag gaca (148) | Gcgcgctctggtt actactggggtgt taacggtgatcag (150) | Aacattggaag taaaaat (152) | Aggga tagc (154) | Caggtgtgggacag cagtattgtggta (156) |

Example 3—Engineering Full Length Monoclonal Antibodies Using the Selected scFv Fragments Although the phage display technology allows for the rapid selection and production of antigen-specific scFv fragments, the complete mAbs with Fc domains have a number of advantages over the scFv. First, only Fc carrying antibodies exert immunological functions, such as complement-dependent cytotoxicity (CDC) and antibody-dependent cellular cytotoxicity (ADCC). Second, bivalent monoclonal antibodies (mAbs) offer stronger antigen-binding avidity than monomeric Fab or scFv Abs. Third, plasma half-life and renal clearance is much faster for Fab or scFv compared to full length IgG. Fourth, bivalent mAb may be internalized at a faster rate compared to that of the corresponding univalent Fab or scFv. Although alpha emitters conjugated to the Fc region may not need to be internalized to kill the targets, many drugs and toxins will benefit from internalization of the immune complex.

Based on the affinity ranking result obtained through competitive ELISA (see Table 4) and the cell-surface binding against ROR2 positive cancer cell line determined using flow cytometry, five phage display clones with high ROR2 binding affinity that specifically recognize ROR2 were selected. The scFv of these selected clones were reconstructed into full-length human IgG1 recombinant antibodies and characterized further.

The selected scFv were converted into full length monoclonal IgG using HEK293 cells using the method of Tomomatsu et al[57]. Antibody variable regions were subcloned into the mammalian expression vectors shown in FIGS. 9a and 9b together with matching Kappa or lambda light chain constant and IgG1 subclass Fc using conventional techniques known in the art. et al The polypeptide sequence of one embodiment of the lambda light chain constant region of hIgG1 is provided herein as SEQ ID No. 209, as follows:

[SEQ ID No. 209]
QPKANPTVTLFPPSSEELQANKATLVCLISDFYPGAVTVAWKADGSPVK
AGVETTKPSKQSNNKYAASSYLSLTPEQWKSHRSYSCQVTHEGSTVEKT
VAPTECS

The coding sequence encoding one embodiment of the lambda light chain constant region of hIgG1 is provided herein as SEQ ID No. 210, as follows:

[SEQ ID No. 210]
Cagcctaaggccaaccctaccgtgaccctgttcccccatcctccgagga actgcaggccaacaaggccaccctcgtgtgcctgatctccgacttctacc ctggcgccgtgaccgtggcctggaaggctgatggatctcctgtgaaggcc ggcgtggaaaccaccaagcctccaagcagtccaacaacaaatacgccgc ctcctcctacctgtccctgacccctgagcagtggaagtcccaccggtcct acagctgccaagtgacccacgagggctccaccgtggaaaagaccgtggct cctaccgagtgctcctag The polypeptide sequence of one embodiment of the kappa light chain constant region of hIgG1 is provided herein as SEQ ID No. 211, as follows:

[SEQ ID No. 211]

```
TVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC
```

The coding sequence encoding one embodiment of the kappa light chain constant region of hIgG1 is provided herein as SEQ ID No. 212, as follows:

[SEQ ID No. 212]

```
accgtggccgctccctccgtgttcatcttcccaccttccgacgagcagctgaagtccggcaccgcttctg
tcgtgtgcctgctgaacaacttctaccccgcgaggccaaggtgcagtggaaggtggacaacgccctgca
gagcggcaactcccaggaatccgtgaccgagcaggactccaaggacagcacctactccctgtcctccacc
ctgaccctgtccaaggccgactacgagaagcacaaggtgtacgcctgcgaagtgacccaccagggcctgt
ctagccccgtgaccaagtctttcaaccggggcgagtgctag
```

The polypeptide sequence of one embodiment of the heavy chain constant region of hIgG1 is provided herein as SEQ ID No. 213, as follows:

[SEQ ID No. 213]

```
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

The coding sequence encoding one embodiment of the heavy chain constant region of hIgG1 is provided herein as SEQ ID No. 214, as follows:

```
gtctcctcagcttccaccaagggcccatcggtcttccccctggcaccctcctccaagagcacctctgggg
gcacagcggccctgggctgcctggtcaaggactacttccccgaaccggtgacggtgtcgtggaactcagg
cgccctgaccagcggcgtgcacaccttcccggccgtcctacagtcctcaggactctactccctcagcagc
gtggtgaccgtgccctccagcagcttgggcacccagacctacatctgcaacgtgaatcacaagcccagca
acaccaaggtggacaagaaggttgagcccaaatcttgtgacaaaactcacacatgcccaccgtgcccagc
acctgaactcctggggggaccgtcagtcttcctcttccccccaaaacccaaggacaccctcatgatctcc
cggacccctgaggtcacatgcgtggtggtggacgtgagccacgaagaccctgaggtcaagttcaactggt
acgtggacggcgtggaggtgcataatgccaagacaaagccgcgggaggagcagtacaacagcacgtaccg
tgtggtcagcgtcctcaccgtcctgcaccaggactggctgaatggcaaggagtacaagtgcaaggtctcc
aacaaagccctcccagcccccatcgagaaaaccatctccaaagccaaagggcagccccgagaaccacagg
```

[SEQ ID No. 214]

```
tgtacaccctgccccatcccgggaggagatgaccaagaaccaggtcagcctgacctgcctggtcaaagg
cttctatcccagcgacatcgccgtggagtgggagagcaatgggcagccggagaacaactacaagaccacg
cctcccgtgctggactccgacggctccttcttcctctacagcaagctcaccgtggacaagagcaggtggc
agcaggggaacgtcttctcatgctccgtgatgcatgaggctctgcacaaccactacacgcagaagagcct
ctccctgtctccgggtaaatga
```

Purified full length IgG1 antibodies exhibit the expected molecular weight under both reducing and non-reducing conditions (see FIG. 10). Kinetic binding analysis confirmed specific binding of full length IgG1 antibodies to human ROR2-ECD, with an equilibrium dissociation constant (KD) in the picomolar range (see Table 7).

TABLE 7

Association constant, dissociation constant and equilibrium dissociation constant of full length ROR2 antibodies

| Clone | Ka (1/Ms) | Kd (1/S) | KD (M) |
|---|---|---|---|
| ROR2-23 | 2.634E+6 | 4.325E−4 | 1.642E−10 |
| ROR2-27 | 8.511E+5 | 6.085E−4 | 7.150E−10 |
| ROR2-90 | 1.025E+6 | 1.669E−4 | 1.629E−10 |
| ROR2-240 | 7.059E+5 | 4.445E−5 | 6.297E−11 |
| ROR2-241 | 1.736E+6 | 5.384E−4 | 3.102E−10 |

Example 4—Epitope Mapping of the Full Length ROR2-Specific IgG1 Monoclonal Antibodies To better understand the structural basis of the ROR2-specific antibody as a drug candidate, a standard epitope mapping was performed by ELISA against a ROR2 peptide array. The peptide array covers the whole length of the ROR2 protein through 96 overlapping peptides (11 amino acids each with 4 amino acids worth of space between them). The peptides were biotinylated at the N-terminal to immobilize them onto streptavidin ELISA plates. A spacer (SGSG) was used to provide flexibility. The space was inserted at the N-terminal biotin-SGSG-15 amino acids. ELISA assays were performed with the full length ROR2 antibodies as the primary antibody and an anti-human Fc AP-conjugated antibody was used for detection. An ELISA example is shown in FIG. 11, antibody #90 binds to a linear epitope KTITATGVLFVRLGP (SEQ ID No. 228). FIG. 12 indicates the epitope position in ROR2 primary structure. This sequence is not shared by ROR1 and not found in human proteins by PBLAST.

Example 5—Binding Properties of the Full Length ROR2-Specific IgG1 Monoclonal Antibodies Binding specificity of the five purified full length IgG1 antibodies (ROR2-23, ROR2-27, ROR2-90, ROR2-240 and ROR2-241) was confirmed by ELISA. ELISA assays were carried out as follows: 20 ng of ROR2 ECD recombinant protein were coated onto 96-well ELISA plates overnight at 4° C. Full length anti-ROR2 IgG1s were incubated at different dilutions in the antigen wells for 1 hour at room temperature. Bound IgG1s were detected with anti-human Fc-HRP antibody (1:10,000, BD Biosciences). The 2,2′-azino-bis-(3-ethylbenzthiazoline-6-sulfonic acid) substrate (Sigma-Aldrich) was added and the reaction was read at 490 nm. These ELISAs confirmed that the full length antibodies also bind to ROR2 ECD (see FIG. 13). These full length antibodies were stable after multiple freeze-and-thaw cycles (F&T), demonstrated by ROR2 ECD ELISA (see FIG. 13).

Binding of the hIgG1 mAbs to the cell surface ROR2 was determined by flow cytometry using the ROR2 positive human erythroleukemic cancer cell line, K562. The full length antibodies recognized ROR2 expressed on the surface of K562 (see FIG. 14).

Example 6—Binding Intensity of the Full Length ROR2-Specific IgG1 Monoclonal Antibodies Human tumour cell lines were authenticated using short tandem repeat (STR) analysis. They were cultured in RPMI1640 (Cellgro) supplemented with 10% fetal bovine serum (FBS, Life Technologies) at 37° C. in a 5% $CO_2$ humidified incubator. They were harvested, washed in PBS and reacted with ROR2-IgG at 1 ug/$10^6$ tumour cells on ice for an hour. #901-IgG was used as a negative control at the same dose. After washing, a secondary PE-conjugated goat anti-human IgG, Fcγ fragment specific (1:100, Jackson ImmunoResearch) was added for another 30 min incubation. Staining was analyzed on a FACSCalibur (BD Biosciences). ROR2 (full length) antibody binding towards multiple cancer cell lines were compared with Rituxan and Herceptin antibodies. The cancer cell lines were derived from breast cancer, colorectal cancer, mesothelioma, hepatocellular carcinoma, ovarian cancer, osteosarcoma, neuroblastoma, etc. ROR2 #90 antibody could recognize most of the tumour cells tested, and in some cases, the binding intensity was higher than Herceptin (see Tables 8 to 10).

TABLE 8

Antibody binding intensity against various carcinoma cell lines

| Name of cell line | Tumor | Rituxan | ROR2 23 | ROR2 27 | ROR2 90 | ROR2 240 | ROR2 241 | Herceptin |
|---|---|---|---|---|---|---|---|---|
| HTB132 | breast CA | 5 | 5 | 8 | 5 | 4 | 45 | 6 |
| HTB26 (MDA-MB-231) | breast CA | 5 | 11 | 7 | 19 | 4 | 23 | 77 |
| AU565 | breast CA | 5 | 102 | 8 | 211 | 4 | 83 | 3817 |
| SKBR3 | breast CA | 5 | 48 | 15 | 98 | 5 | 27 | 1231 |

TABLE 8-continued

Antibody binding intensity against various carcinoma cell lines

| Name of cell line | Tumor | Rituxan | ROR2 23 | ROR2 27 | ROR2 90 | ROR2 240 | ROR2 241 | Herceptin |
|---|---|---|---|---|---|---|---|---|
| HTB27 | breast CA | 5 | 58 | 11 | 125 | 7 | 24 | 1448 |
| MCF7 | breast CA | 5 | 52 | 27 | 115 | 3 | 21 | 177 |
| MCF7-Luc | breast CA | 5 | 111 | 74 | 190 | 39 | 42 | 296 |
| CCL-227 SW620 | CRC | 5 | | | 26 | | | 61 |
| HTB37-Caco2 | CRC | 5 | 37 | 13 | 91 | 6 | 24 | 268 |
| COLO 205 | CRC | 5 | 26 | 7 | 44 | 4 | 24 | 304 |
| SKHEP-1 | HCC | 5 | 42 | 23 | 74 | 21 | 53 | 88 |
| HEP G2 | HCC | 5 | 30 | 11 | 49 | 4 | 36 | 255 |
| NCI-H2052 | mesothelioma | 5 | 65 | 46 | 101 | 8 | 43 | 71 |
| OVCAR3 | ovarian CA | 5 | 35 | 7 | 48 | 4 | 22 | 146 |
| SKOV3 | ovarian CA | 5 | 116 | 36 | 246 | 5 | 42 | 2005 |

TABLE 9

Antibody binding intensity against various sarcoma cell lines

| Name of cell line | Tumor | Rituxan | ROR2 23 | ROR2 27 | ROR2 90 | ROR2 240 | ROR2 241 | Herceptin |
|---|---|---|---|---|---|---|---|---|
| OUMS 27 | chondrosarcoma | 5 | 71 | 48 | 78 | 6 | 53 | 64 |
| JN DSRCT | DSRCT | 5 | 50 | 5 | 84 | 3 | 27 | 236 |
| CHP100 | EW/PNET | 5 | 30 | 18 | 57 | 7 | 16 | 87 |
| TC32 | EW/PNET | 6 | 37 | 20 | 70 | 4 | 17 | 125 |
| TC71 | EW/PNET | 5 | 46 | 21 | 68 | 10 | 12 | 91 |
| SKES-1 | EW/PNET | 5 | 22 | 12 | 28 | 5 | 12 | 146 |
| U2OS | osteosarcoma | 5 | 52 | 29 | 94 | 39 | 60 | 90 |
| CRL1427 | osteosarcoma | 5 | 30 | 11 | 45 | 4 | 54 | 108 |
| RG187 | osteosarcoma | 5 | 44 | 19 | 79 | 4 | 29 | 240 |

TABLE 10

Antibody binding intensity against various cancerous cells

| Name of cell line | Tumor | Rituxan | ROR2 23 | ROR2 27 | ROR2 90 | ROR2 240 | ROR2 241 | Herceptin |
|---|---|---|---|---|---|---|---|---|
| U251 LUC | Glioma | 5 | 14 | 9 | 27 | 5 | 120 | 94 |
| SKMEL-5 | melanoma | 5 | 7 | 2 | 8 | 1 | 5 | 21 |
| M14 | melanoma | 5 | 9 | 5 | 17 | 4 | 12 | 57 |
| SKMEL28 | melanoma | 5 | 20 | 8 | 26 | 4 | 20 | 147 |
| HTB63 | melanoma | 5 | 16 | 8 | 27 | 5 | 16 | 156 |
| OCM1 | melanoma | 5 | 10 | 6 | 18 | 3 | 19 | 66 |
| LAN-1 | neuroblastoma | 5 | 34 | 28 | 48 | 37 | 68 | 2 |
| BE(2)S | neuroblastoma | 5 | 26 | 21 | 40 | 26 | 58 | 4 |
| IMR32 | neuroblastoma | 5 | 24 | 16 | 51 | 29 | 50 | 5 |
| BE(1)N | neuroblastoma | 5 | 273 | 244 | 302 | 279 | 352 | 2 |
| SKNSH | neuroblastoma | 5 | 170 | 8 | 105 | 113 | 141 | 174 |
| SKNMM | neuroblastoma | 6 | 77 | 69 | 117 | 84 | 126 | 7 |
| SKNJB | neuroblastoma | 5 | 182 | 141 | 254 | 199 | 238 | 20 |
| NMB7 | neuroblastoma | 5 | 35 | 23 | 47 | 33 | 58 | 12 |
| NB5 | neuroblastoma | 5 | 32 | 20 | 47 | 17 | 56 | 88 |
| H345 | SCLC | 5 | 34 | 26 | 48 | 36 | 49 | 6 |
| H69 | SCLC | 4 | 9 | 24 | 15 | 9 | 131 | 10 |
| H524 | SCLC | 5 | 28 | 16 | 20 | 7 | 32 | 14 |

Example 7—Engineering of Bispecific Antibodies (BsAb Antibody)

Bispecific antibodies (BsAb) are single-chain bispecific antibodies comprising ROR2 specific antibodies in the scFv format, at the N-terminal end and an anti-human CD3ε scFv mouse monoclonal antibody at the C-terminal end.[58] The DNA fragments coding for the ROR2 scFv antibody and the anti-human CD3ε scFv antibody (SEQ ID No. 220) were synthesized by Genewiz and subcloned into Eureka's mammalian expression vector pGSN-Hyg using standard DNA technology. A hexhistamine tag is inserted downstream of the ROR2 BsAb antibodies at the C-terminal end for antibody purification and detection. HEK293 cells were transfected with the ROR2 BsAb expression vector. HEK293 cell supernatants containing secreted ROR2 BsAb molecules were collected. ROR2 BsAb was purified using HisTrap HP column (GE healthcare) by FPLC AKTA system. Briefly, CHO cell culture was clarified and loaded to the column with low imidazole concentration (20 mM), and then an isocratic high imidazole concentration elution buffer (500 mM) was used to elute the bound ROR2 BsAb proteins. Molecular weight of the purified ROR2 BsAb antibodies were measured under non-reducing conditions by electrophoresis (see FIG. 15).

The following is an example of the sequences used to engineer a ROR2 Antibody BsAb sequence using clone #241 and an anti-human CD3ε scFv antibody (see tables 3 and 4, and Example 2 above).

The BsAb antibody comprises the light chain variable region of antibody clone #241 (SEQ ID No. 206) joined to the N-terminus of linker 1 (SEQ ID No. 216). The C-terminus of linker 1 is joined to the N-terminus of the heavy chain variable region of antibody clone #241 (SEQ ID No. 208). The C-terminus of the heavy chain variable region of antibody clone #241 is joined to the N-terminus of linker 2 (SEQ ID No. 218). The C-terminus of linker 2 is joined to the N-terminus of anti-human CD3ε scFv, which has a His tag at its C-terminus (SEQ ID No. 220). The full polypeptide sequence of one embodiment of the BsAb antibody is provided herein as SEQ ID No. 215, as follows:

[SEQ ID No. 215]
SYELTQPLSVSVALGQTARITCGGNNIGSKNVHWYQQKPGQAPVLVIYRDSNRPSGIPERFSGSNSGNTA

TLTISRAQAGDEADYYCQVWDSSIVVFGGGTKLTVLGSRGGGGSGGGGSGGGGSLEMAEVQLVQSGAEVK

KPGASVKVSCKASGYTFTNYYIHWVRQAPGQGLEWMGIINPTSGRTRYAQRFQGRVTMTRDTSTNTVYMD

LSSLRSEDTAMYYCARSGYYWGVNGDQWGQGTLVTVSSGGGGSDVQLVQSGAEVKKPGASVKVSCKASGY

TFTRYTMHWVRQAPGQGLEWIGYINPSRGYTNYADSVKGRFTITTDKSTSTAYMELSSLRSEDTATYYCA

RYYDDHYCLDYWGQGTTVTVSSGEGTSTGSGGSGGSGGADDIVLTQSPATLSLSPGERATLSCRASQSVS

YMNWYQQKPGKAPKRWIYDTSKVASGVPARFSGSGSGTDYSLTINSLEAEDAATYYCQQWSSNPLTFGGG

TKVEIKHHHHHH

The polypeptide sequence of one embodiment of linker 1 is provided herein as SEQ ID No. 216, as follows:

[SEQ ID No. 216]
SRGGGGSGGGGSGGGGSLEMA

The coding sequence encoding one embodiment of linker 1 is provided herein as SEQ ID No. 217, as follows:

[SEQ ID No. 217]
ctagaggtggtggtggtagcggcggcggcggctctggtggtggtggatcc

The polypeptide sequence of one embodiment of the heavy chain of the Ror2 antibody clone #241 is provided above as SEQ ID No. 208. The coding sequence encoding one embodiment of the heavy chain of the Ror2 antibody clone #241 is provided above as SEQ ID No. 207.

The polypeptide sequence of one embodiment of linker 2 is provided herein as SEQ ID No. 218, as follows:

[SEQ ID No. 218]
GGGGS

The coding sequence encoding one embodiment of linker 2 is provided herein as SEQ ID No. 219, as follows:

[SEQ ID No. 219]
ggcggggaggatcc

The polypeptide sequence of one embodiment of the AntiCD3 scFv-his tag is provided herein as SEQ ID No. 220, as follows:

[SEQ ID No. 220]
DVQLVQSGAEVKKPGASVKVSCKASGYTFTRYTMHWVRQAPGQGLEWIGY

INPSRGYTNYADSVKGRFTITTDKSTSTAYMELSSLRSEDTATYYCARYY

DDHYCLDYWGQGTTVTVSSGEGTSTGSGGSGGSGGADDIVLTQSPATLSL

SPGERATLSCRASQSVSYMNWYQQKPGKAPKRWIYDTSKVASGVPARFSG

SGSGTDYSLTINSLEAEDAATYYCQQWSSNPLTFGGGTKVEIKHHHHHH

The coding sequence encoding one embodiment of the AntiCD3 scFv-his tag is provided herein as SEQ ID No. 221, as follows:

[SEQ ID No. 221]
gacgtgcagctggtgcagagcggagctgaagtgaagaaacctggcgcctc cgtgaaggtgtcctgcaaagctagcggctataccttcacccggtacacca tgcactgggtgcgccaggcacctggacagggactggaatggatcggctac atcaaccctcccggggctacaccaactacgccgactctgtgaagggccg gttcaccatcaccaccgataagtccaccagcaccgcttacatggaactgt cctccctgagatccgaggacaccgctacctactattgcgcccggtactac gacgaccactactgcctggactactggggacagggaaccacagtgaccgt gtcctctggcgagggcacctctactggatctgggggaagtggtggttctg gcggcgctgacgacatcgtgctgacccagtctccagccaccctgtctctg agcccaggcgagagagctaccctgtcctgcagagcctcccagtccgtgtc ctacatgaattggtatcagcagaagcctggcaaggcccctaagcggtgga tctacgacacctccaaggtggcctctggcgtgccagcccggttttccgga tctggctctggcaccgactactccctgaccatcaacagcctggaagccga ggacgctgccacctattactgccagcagtggtcctccaaccccctgacct ttggaggcggcaccaaggtggaaatcaagcaccaccatcatcaccactga Example 8—In Vitro T Cell Killing Assay in the Presence of ROR2 BsAb Full length ROR2 BsAb antibodies killed cancer cells in a ROR2-dependent manner. Tumour cytotoxicity was assayed by $^{51}$Cr release as previously described (Cheng M, Ahmed M, Xu H, Cheung N K. Structural design of disialoganglioside GD2 and CD3-bispecific antibodies to redirect T cells for tumor therapy. Int J Cancer. 2014), and EC50 was calculated using SigmaPlot software. Effector T cells were purified from human PBMC using Pan T cell isolation kit, and then activated and expanded with CD3/CD28 Dynabeads (Invitrogen) according to manufacturer's protocol. Activated T cells (ATC) were cultured and maintained in F10 medium plus 30 U/ml IL-2, and used at day 14-21. CD3+ T cells were above 99% by FACS analysis. The antibodies killed multiple ROR2 positive cancer cell lines (U2OS, BE(1)N, LAN-1 and AU565) efficiently in the in vitro T cell killing assays, but none of the ROR2 BsAb antibodies killed the ROR2 negative cancer cell line M14 (see FIGS. 16-20).

Example 9—In Vivo Human Neuroblastoma and Human Breast Cancer Mouse Xenograft Models to Test ROR2 BsAb (SSK)

Full length ROR2 BsAb antibodies were tested in vivo against the breast cancer model, MCF7, and the neuroblastoma model, SKBE(2)S, xenografted in immune deficient mice, BALB-Rag2-KO/IL-2R-γc-KO (DKO for double knockout), which can be engrafted with human lymphocytes. In both models, ROR2 BsAb antibodies eliminated the tumor burden in DKO mice very efficiently, see FIGS. 21 and 22 for the results in relation to full length antibody #90. Although MCF7 exhibits low expression of Her2, and the high affinity mAb, Herceptin, fails to kill MCF7 cells in vivo. However, ROR2 antibodies killed MCF7 cancer cells and inhibited the tumor growth (see FIG. 21). Clone #90 was superior to clone #240 in vivo despite it's less favorable Kd.

Example 10—In Vitro Assessment of Retroviral Constructs pMSCV-602-90GA-BBz-ires-EGFP CAR and pMSCV-901scFv-BBz-ires-EGFP CAR This Example relates to proof-of-concept experiments for ROR2 antibody CAR-T therapy. ROR2 #90 antibody was engineered into chimeric antibody receptor and expressed on the surface of T cells via a retroviral mammalian expression system. The inventors confirmed the expression of ROR2 #90 CAR on the surface of T cells, as shown in FIG. 23. Furthermore, the ROR2 #90 CAR-T cells can kill ROR2 positive cancer cells in a dose-dependent manner, but control 901 CAR-T cells didn't kill cancer cells specifically, as shown in FIG. 24.

1. Transduction Procedure

PG13 (GaLV pseudotyped) packaging cell line was used for transfection of pMSCV plasmids. Human T-cells were used for transduction after 4-day stimulation and expansion with CD3/CD28 beads (Dynabeads®, Invitrogen) in the presence of interleukine-2 at 30 U/ml. Cell free supernatant was filtered and applied on T-cells in Retronectin (Takara) coated 6-well plates at 48 and 72 hours after PG13 virus producer cell line transfection.

2. In Vitro Characterization

Transduction efficiency was assessed by FACS using biotinylated Protein-L (primary) antibody (GeneScript) and PE-conjugated (secondary) antibody (BD Biosciences). Repeat FACS analyses were done at 72 hours and every 3-4 days thereafter. Level of transduction was about 50% for both constructs (see FIG. 23). Of note, detected GFP expression was miniscule (1-3%).

Functional assessment of the transduced T cells was performed using 40-hour $^{51}$Cr release assay. T cells transduced with pMSCV 3F8-BBz-CAR served as control effectors. Effector-to-target ratios were 5:1, 10:1, 25:1. Two neuroblastoma cell lines with ROR2 expression were used as targets: SKNMM with 71% ROR2 positivity and SKNSH with 99% positivity by FACS.

Clone #90-CAR T cells exhibited higher level of cytotoxicity against SKNSH as compared to 901 control CAR T cells at E:T ratios 10:1 and 25:1 (see FIG. 26).

Example 11—Investigate ROR2 Expression in Normal Human Tissues

Endogenous ROR2 expression in normal human tissues was investigated using quantitative PCR. Total RNA from normal tissues and normal peripheral blood mononuclear cells (PBMC) was isolated using Trizol Reagent (Invitrogen) according to the manufacturer's instructions. One μl of cDNA synthesized from 1 ug of total RNA was used for real-time qPCR using Applied Biosystems (ABI) Sequence Detection System 7300. β2 microglobulin (β2M) was used as the endogenous control, and neuroblastoma cell line NMB7 as the positive control. Gene expression assays were from ABI:ROR2:Hs00896176_m1; and β2M: 4326319E. Each sample was quantified using the ΔΔCT method as a relative fold-difference when compared with normal spleen tissue. Low to medium expression of ROR2 mRNA were detected in testes, ileum and sigmoid colon (see Table 11). ROR2 expression in healthy PBMC was low in all the samples examined using spleen as reference (see Table 12).

TABLE 11

Transcript of ROR2 in human tissues

| Tissue Name | SAMPLE | CT-ROR2 | CT-B2M | Relative quantitation normalized with B2M ROR2 |
|---|---|---|---|---|
| NMB7 - NB cell line | 705S | 24.23 | 20.20 | 86 |
| ILEUM | 9396 | 40.00 | 26.65 | 0 |
| PONS | 9401 | 37.11 | 25.38 | 0 |
| PANCREAS | 9406 | 34.38 | 24.07 | 1 |
| HEART | 9408 | 31.42 | 21.08 | 1 |
| SKELETAL MUSCLE | 10192 | 35.25 | 22.43 | 0 |
| CEREBELLUM | 10193 | 33.70 | 22.93 | 1 |
| FRONTAL LOBE | 10194 | 32.86 | 24.69 | 5 |
| LIVER | 10199 | 35.23 | 25.35 | 1 |
| LUNG | 10201 | 32.56 | 22.95 | 2 |
| ADRENAL | 10202 | 29.63 | 21.69 | 6 |
| SPLEEN | 10204 | 35.52 | 25.07 | 1 |
| KIDNEY | 10206 | 35.37 | 22.90 | 0 |
| TESTES | 10207 | 27.69 | 22.84 | 49 |
| STOMACH | 9404 | 31.12 | 23.72 | 8 |
| ILEUM | 10191 | 30.26 | 24.64 | 28 |
| SIGMOID COLON | 10203 | 28.86 | 22.53 | 17 |

TABLE 12

Transcript of ROR2 in human PBMCs

| NAME | SAMPLE | CT-ERBB2 | CT-ROR1 | CT-ROR2 | CT-B2M | Relative quantitation normalized with B2M ROR2 |
|---|---|---|---|---|---|---|
| NMB7 | 7058 | 27.46 | 26.55 | 25.25 | 21.17 | 83.14 |
| PBMC#1 | 11295 | 36.90 | 40.00 | 40.00 | 22.74 | 0.00 |
| PBMC#2 | 11118 | 35.51 | 39.11 | 40.00 | 20.78 | 0.00 |
| PBMC#3 | 11047 | 29.69 | 31.22 | 34.09 | 17.93 | 0.02 |
| PBMC#4 | 11051 | 30.14 | 34.14 | 33.74 | 19.00 | 0.05 |
| PBMC#5 | 11056 | 29.27 | 33.03 | 31.26 | 18.50 | 0.20 |
| PBMC#6 | 11688 | 35.77 | 39.18 | 40.00 | 22.23 | 0.00 |
| PBMC#7 | 11702 | 31.15 | 36.09 | 36.42 | 20.85 | 0.03 |
| SPLEEN | 10204 | 36.11 | 35.69 | 35.52 | 25.07 | 1.00 |

REFERENCES

1. Ottaviani G, Jaffe N: The epidemiology of osteosarcoma. Cancer Treat Res 152:3-13, 2009
2. Janeway K A, Grier H E: Sequelae of osteosarcoma medical therapy: a review of rare acute toxicities and late effects. Lancet Oncol 11:670-8, 2010
3. Hameed M, Dorfman H: Primary malignant bone tumors-recent developments. Semin Diagn Pathol 28:86-101, 2011
4. PosthumaDeBoer J, Witlox M A, Kaspers G J, et al: Molecular alterations as target for therapy in metastatic osteosarcoma: a review of literature. Clin Exp Metastasis 28:493-503, 2011
5. Gilchrist G S, Ivins J C, Ritts R E, Jr., et al: Adjuvant therapy for nonmetastatic osteogenic sarcoma: an evaluation of transfer factor versus combination chemotherapy. Cancer Treat Rep 62:289-94, 1978
6. Muller C R, Smeland S, Bauer H C, et al: Interferon-alpha as the only adjuvant treatment in high-grade osteosarcoma: long term results of the Karolinska Hospital series. Acta Oncol 44:475-80, 2005
7. Kleinerman E S, Gano J B, Johnston D A, et al: Efficacy of liposomal muramyl tripeptide (CGP 19835A) in the treatment of relapsed osteosarcoma. Am J Clin Oncol 18:93-9, 1995
8. Rao R D, Anderson P M, Arndt C A, et al: Aerosolized granulocyte macrophage colony-stimulating factor (GM-CSF) therapy in metastatic cancer. Am J Clin Oncol 26:493-8, 2003
9. Duan X, Jia S F, Koshkina N, et al: Intranasal interleukin-12 gene therapy enhanced the activity of ifosfamide against osteosarcoma lung metastases. Cancer 106:1382-8, 2006
10. Heiner J P, Miraldi F, Kallick S, et al: Localization of GD2-specific monoclonal antibody 3F8 in human osteosarcoma. Cancer Res 47:5377-81, 1987
11. Bruland O S, Hoifodt H, Hall K S, et al: Bone marrow micrometastases studied by an immunomagnetic isolation procedure in extremity localized non-metastatic osteosarcoma patients. Cancer Treat Res 152:509-15, 2009
12. Ullenhag G J, Spendlove I, Watson N F, et al: T-cell responses in osteosarcoma patients vaccinated with an anti-idiotypic antibody, 105AD7, mimicking CD55. Clin Immunol 128:148-54, 2008
13. Geller D S, Gorlick R: HER-2 targeted treatment of osteosarcoma: the challenges of developing targeted therapy and prognostic factors for rare malignancies. Expert Opin Pharmacother 11:51-61, 2010
14. Morioka K, Tanikawa C, Ochi K, et al: Orphan receptor tyrosine kinase ROR2 as a potential therapeutic target for osteosarcoma. Cancer Sci 100:1227-33, 2009
15. Yu A L, Gilman A L, Ozkaynak M F, et al: Anti-GD2 antibody with GM-CSF, interleukin-2, and isotretinoin for neuroblastoma. N Engl J Med 363:1324-34, 2010
16. Maris J M, Hogarty M D, Bagatell R, et al: Neuroblastoma. Lancet 369:2106-20, 2007
17. Pearson A D, Craft A W, Pinkerton C R, et al: High-dose rapid schedule chemotherapy for disseminated neuroblastoma. Eur J Cancer 28A:1654-9, 1992
18. Kushner B H, LaQuaglia M P, Bonilla M A, et al: Highly effective induction therapy for stage 4 neuroblastoma in children over 1 year of age. J Clin Oncol 12:2607-13, 1994
19. LaQuaglia M P, Kushner B H, Heller G, et al: Stage 4 neuroblastoma diagnosed at more than one year of age: gross total resection and clinical outcome. J Pediatr Surg 29:1162-1166, 1994
20. Franks L M, Bollen A, Seeger R C, et al: Neuroblastoma in adults and adolescents: an indolent course with poor survival. Cancer 79:2028-35, 1997
21. Kushner B, Kramer K, LaQuaglia M, et al: Neuroblastoma in adolescents and adults: The Memorial Sloan-Kettering experience. Med Pediatr Oncol: in press, 2003
22. Kushner B H, Wolden S, LaQuaglia M P, et al: Hyperfractionated low-dose radiotherapy for high-risk neuroblastoma after intensive chemotherapy and surgery. J Clin Oncol 19:2821-8, 2001
23. Pearson A D, Pinkerton C R, Lewis I J, et al: High-dose rapid and standard induction chemotherapy for patients aged over 1 year with stage 4 neuroblastoma: a randomised trial. Lancet Oncol 9:247-56, 2008
24. Boyiadzis M, Foon K A: Approved monoclonal antibodies for cancer therapy. Expert Opin Biol Ther 8:1151-8, 2008
25. Yan L, Hsu K, Beckman R A: Antibody-based therapy for solid tumors. Cancer J 14:178-83, 2008
26. Cheung N K, Walter E I, Smith-Mensah W H, et al: Decay-accelerating factor protects human tumor cells from complement-mediated cytotoxicity in vitro. J Clin Invest 81:1122-8, 1988
27. Chen S, Caragine T, Cheung N K, et al: CD59 expressed on a tumor cell surface modulates decay-accelerating factor expression and enhances tumor growth in a rat model of human neuroblastoma. Cancer Res 60:3013-8, 2000
28. Kushner B H, Cheung N K: Absolute requirement of CD11/CD18 adhesion molecules, FcRII and the phosphatidylinositol-linked FcRIII for monoclonal antibody-mediated neutrophil antihuman tumor cytotoxicity. Blood 79:1484-90, 1992
29. Metelitsa I S, Gillies S D, Super M, et al: Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis. Blood 99:4166-73, 2002
30. Modak S, Cheung N K: Disialoganglioside directed immunotherapy of neuroblastoma. Cancer Invest 25:67-77, 2007
31. Cheung N K, Saarinen U M, Neely J E, et al: Monoclonal antibodies to a glycolipid antigen on human neuroblastoma cells. Cancer Res 45:2642-9, 1985
32. Mujoo K, Kipps T J, Yang H M, et al: Functional properties and effect on growth suppression of human neuroblastoma tumors by isotype switch variants of monoclonal antiganglioside GD2 antibody 14.18. Cancer Res 49:2857-61, 1989
33. Gillies S D, Lo K M, Wesolowski J: High-level expression of chimeric antibodies using adapted cDNA variable region cassettes. J Immunol Methods 125:191-202, 1989
34. Barker E, Mueller B M, Handgretinger R, et al: Effect of a chimeric anti-ganglioside GD2 antibody on cell-mediated lysis of human neuroblastoma cells. Cancer Res 51:144-9, 1991
35. Barker E, Reisfeld R A: A mechanism for neutrophil-mediated lysis of human neuroblastoma cells. Cancer Res 53:362-7, 1993
36. Mueller B M, Reisfeld R A, Gillies S D: Serum half-life and tumor localization of a chimeric antibody deleted of the CH2 domain and directed against the disialoganglioside GD2. Proc. Natl Acad Sci, USA 87:5702-5705, 1990
37. Mueller B M, Romerdahl C A, Gillies S D, et al: Enhancement of antibody-dependent cytotoxicity with a chimeric anti-GD2 antibody. J Immunol 144:1382-1386, 1990
38. Al-Shawi R, Ashton S V, Underwood C, et al: Expression of the Ror1 and Ror2 receptor tyrosine kinase genes during mouse development. Dev Genes Evol 211:161-71, 2001
39. Forrester W C: The Ror receptor tyrosine kinase family. Cell Mol Life Sci 59:83-96, 2002
40. Green J L, Kuntz S G, Sternberg P W: Ror receptor tyrosine kinases: orphans no more. Trends Cell Biol 18:536-44, 2008
41. Oishi I, Suzuki H, Onishi N, et al: The receptor tyrosine kinase Ror2 is involved in non-canonical Wnt5a/JNK signalling pathway. Genes Cells 8:645-54, 2003
42. Nishita M, Enomoto M, Yamagata K, et al: Cell/tissue-tropic functions of Wnt5a signaling in normal and cancer cells. Trends Cell Biol 20:346-54, 2010
43. Takeuchi S, Takeda K, Oishi I, et al: Mouse Ror2 receptor tyrosine kinase is required for the heart development and limb formation. Genes Cells 5:71-8, 2000
44. DeChiara T M, Kimble R B, Poueymirou W T, et al: Ror2, encoding a receptor-like tyrosine kinase, is required for cartilage and growth plate development. Nat Genet 24:271-4, 2000
45. Nomi M, Oishi I, Kani S, et al: Loss of mRor1 enhances the heart and skeletal abnormalities in mRor2-deficient mice: redundant and pleiotropic functions of mRor1 and mRor2 receptor tyrosine kinases. Mol Cell Biol 21:8329-35, 2001
46. Yoda A, Oishi I, Minami Y: Expression and function of the Ror-family receptor tyrosine kinases during development: lessons from genetic analyses of nematodes, mice, and humans. J Recept Signal Transduct Res 23:1-15, 2003
47. Afzal A R, Jeffery S: One gene, two phenotypes: ROR2 mutations in autosomal recessive Robinow syndrome and autosomal dominant brachydactyly type B. Hum Mutat 22:1-11, 2003
48. Afzal A R, Rajab A, Fenske C D, et al: Recessive Robinow syndrome, allelic to dominant brachydactyly type B, is caused by mutation of ROR2. Nat Genet 25:419-22, 2000
49. Wright T M, Brannon A R, Gordan J D, et al: Ror2, a developmentally regulated kinase, promotes tumor growth potential in renal cell carcinoma. Oncogene 28:2513-23, 2009
50. Kubo T, Kuroda Y, Shimizu H, et al: Resequencing and copy number analysis of the human tyrosine kinase gene family in poorly differentiated gastric cancer. Carcinogenesis 30:1857-64, 2009
51. Ohta H, Aoyagi K, Fukaya M, et al: Cross talk between hedgehog and epithelial-mesenchymal transition pathways in gastric pit cells and in diffuse-type gastric cancers. Br J Cancer 100:389-98, 2009
52. O'Connell M P, Fiori J L, Xu M, et al: The orphan tyrosine kinase receptor, ROR2, mediates Wnt5A signaling in metastatic melanoma. Oncogene 29:34-44, 2010
53. Kobayashi M, Shibuya Y, Takeuchi J, et al: Ror2 expression in squamous cell carcinoma and epithelial dysplasia of the oral cavity. Oral Surg Oral Med Oral Pathol Oral Radiol Endod 107-398-406, 2009
54. Yamamoto H, Oue N, Sato A, et al: Wnt5a signaling is involved in the aggressiveness of prostate cancer and expression of metalloproteinase. Oncogene 29:2036-46, 2010
55. Enomoto M, Hayakawa S, Itsukushima S, et al: Autonomous regulation of osteosarcoma cell invasiveness by Wnt5a/Ror2 signaling. Oncogene 28:3197-208, 2009
56. Asgharzadeh S, Pique-Regi R, Sposto R, et al: Prognostic significance of gene expression profiles of metastatic neuroblastomas lacking MYCN gene amplification. J Natl Cancer Inst 98:1193-203, 2006
57. Tomimatsu K, Matsumoto S, Yamashita M, Teruya K, Katakura Y, Kabayama S & Shirahat S. Production of human monoclonal antibodies against FceRIa by a method combining in vitro immunization with phage display. Biosci Biotechnol Biochem 2009; 73 (7) 1465-1469.
58. Brischwein, K. et al. MT110: A novel bispecific single-chain antibody construct with high efficacy in eradicating established tumors. Molecular Immunology 43, 1129-1143 (2006)
59. Cheng M, Ahmed M, Xu H, Cheung N K. Structural design of disialoganglioside GD2 and CD3-bispecific antibodies to redirect T cells for tumor therapy. Int J Cancer. 2014
60 Rebagay G, Yan S, Liu C, and Cheung N K V. ROR1 and ROR2 in Human Malignancies: Potentials for Targeted Therapy. Frontiers in Oncology (Cancer Molecular Targets and Therapeutics), 2:34, 2012
61. Edris et al., J. Pathol 227:223, 2012
62. Hudecek et al, Blood 116:4532, 2010.

The disclosures, including the claims, figures and/or drawings, of each and every patent, patent application, and publication cited herein are hereby incorporated herein by reference in their entireties. To the extent that any definitions in documents incorporated by reference are inconsistent with the definitions provided herein, the definitions provided herein are controlling. Although the invention has been described with reference to the presently preferred embodiments, it should be understood that various changes and modifications, as would be obvious to one skilled in the art, can be made without departing from the spirit of the invention.

The invention claimed is:

1. A human anti-Receptor Tyrosine Kinase-Like Orphan Receptor 2 (ROR2) antibody, or a functional fragment thereof, wherein the antibody or functional fragment thereof comprises a heavy chain with heavy chain CDRs 1-3 and a light chain with light chain CDRs 1-3, wherein the heavy chain CDRs 1-3 and light chain CDRs 1-3 have the amino acid sequences of SEQ ID NOs:61, 63, 65, 67, 69, and 71, respectively.

2. The antibody or functional fragment thereof according to claim 1, wherein the antibody or functional fragment thereof comprises a light chain variable region (VL) and a heavy chain variable region (VH), the light chain variable region and heavy chain variable region comprising the amino acid sequences of SEQ ID NOs:178 and 180.

3. The antibody or functional fragment thereof according to claim 1, which further comprises one or more protecting groups, wherein the one or more protecting groups are selected from the group consisting of acetyl, amide, 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl(Xan), Trityl (Trt), 4-methyltrityl (Mtt), 4-methoxytrityl (Mmt), 4-methoxy-2,3,6-trimethylbenzenesulphonyl(Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl(MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-di-axocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Born), t-butoxycarbonyl (Boc), cyclohexyloxy (cHxO), t-butoxymethyl (Burn), t-butoxy (tBuO), t-Butyl (tBu), and Trifluoroacetyl (TFA).

4. An isolated nucleic acid encoding a human anti-Receptor Tyrosine Kinase-Like Orphan Receptor 2 (ROR2) antibody, or a functional fragment thereof, wherein the antibody or functional fragment thereof comprises a heavy chain with heavy chain CDRs 1-3 and a light chain with light chain CDRs 1-3, wherein the heavy chain CDRs 1-3 and light chain CDRs 1-3 have the amino acid sequences of SEQ ID NOs:61, 63, 65, 67, 69, and 71, respectively.

5. An isolated nucleic acid according to claim 4, wherein the nucleic acid comprises the nucleotide sequences of SEQ ID NOs:177 and 179.

6. An antibody-drug conjugate (ADC) comprising the antibody or functional fragment thereof according to claim 1 and a cytotoxic moiety.

7. A conjugate according to claim 6, wherein the cytotoxic moiety is a toxin selected from monomethyl auristatin E (MMAE), monomethyl auristatin F (MMAF) or maytansine.

8. A chimeric antigen receptor (CAR) that comprises an ectodomain comprising the antibody or functional fragment thereof according to claim 1.

9. A chimeric antigen receptor according to claim 8, wherein the receptor comprises a transmembrane domain.

10. A chimeric antigen receptor according to claim 8, wherein the receptor comprises an endodomain.

11. A pharmaceutical composition comprising an antibody or a functional fragment thereof according to claim 1 optionally derivatised; and optionally a pharmaceutically acceptable vehicle.

12. An expression vector comprising the nucleic acid according to claim 4.

13. A host cell comprising the expression vector according to claim 12.

14. A method of preparing a recombinant antibody or functional fragment thereof, the method comprising (i) culturing at least one cell defined in claim 13 capable of expressing the required antibody or functional fragment thereof; and (ii) isolating the antibody or functional fragment thereof.

* * * * *